US009687536B2

(12) United States Patent
Nagata et al.

(10) Patent No.: US 9,687,536 B2
(45) Date of Patent: Jun. 27, 2017

(54) METHODS AND COMPOSITIONS FOR INTRANASAL DELIVERY

(75) Inventors: Ryoichi Nagata, Kagoshima (JP); Shunji Haruta, Kagoshima (JP)

(73) Assignees: SHIN NIPPON BIOMEDICAL LABORATORIES, LTD., Kagoshima-Shi, Kagoshima (JP); THE CHEMO-SERO-THERAPEUTIC RESEARCH INSTITUTE, Kita-Ku, Kumamoto-Shi, Kumamoto (JP)

( * ) Notice: Subject to any disclaimer, the term of this patent is extended or adjusted under 35 U.S.C. 154(b) by 0 days.

(21) Appl. No.: 13/640,623

(22) PCT Filed: Apr. 15, 2011

(86) PCT No.: PCT/JP2011/002225
§ 371 (c)(1),
(2), (4) Date: Dec. 18, 2012

(87) PCT Pub. No.: WO2011/129120
PCT Pub. Date: Oct. 20, 2011

(65) Prior Publication Data
US 2013/0129781 A1    May 23, 2013

Related U.S. Application Data

(60) Provisional application No. 61/324,542, filed on Apr. 15, 2010.

(51) Int. Cl.

| | | |
|---|---|---|
| A61K 39/00 | (2006.01) | |
| A61K 39/12 | (2006.01) | |
| A61K 9/00 | (2006.01) | |
| A61K 39/05 | (2006.01) | |
| A61K 39/08 | (2006.01) | |
| A61K 39/145 | (2006.01) | |
| A61K 9/19 | (2006.01) | |

(52) U.S. Cl.
CPC ........ *A61K 39/0005* (2013.01); *A61K 9/0043* (2013.01); *A61K 9/19* (2013.01); *A61K 39/05* (2013.01); *A61K 39/08* (2013.01); *A61K 39/12* (2013.01); *A61K 39/145* (2013.01); *A61K 2039/5252* (2013.01); *A61K 2039/543* (2013.01); *C12N 2760/16134* (2013.01)

(58) Field of Classification Search
CPC .............. A61K 2300/00; A61K 9/0043; A61K 9/0075; A61K 38/00; A61K 39/00; A61K 39/12; A61K 39/35; A61K 39/39; A61K 9/0053; A61K 9/0056; A61K 9/20; A61K 2039/521; A61K 2039/543; A61K 2039/544; A61K 2039/545; A61K 2039/55505; A61K 2039/55511
See application file for complete search history.

(56) References Cited

U.S. PATENT DOCUMENTS

| | | | | |
|---|---|---|---|---|
| 8,337,817 | B2 * | 12/2012 | Nagata | A61K 9/0043 424/46 |
| 8,827,946 | B2 * | 9/2014 | Tsutsui | A61K 9/0043 604/212 |
| 9,101,539 | B2 * | 8/2015 | Nagata | A61K 9/0043 |
| 2003/0092145 | A1 | 5/2003 | Jira et al. | |
| 2003/0186271 | A1 | 10/2003 | Hwang et al. | |
| 2004/0042972 | A1 | 3/2004 | Truong-le et al. | |
| 2006/0292173 | A1 | 12/2006 | Macadam | |
| 2007/0275014 | A1 | 11/2007 | Yusibov et al. | |
| 2008/0206281 | A1 * | 8/2008 | Look | A61K 39/155 424/211.1 |
| 2008/0226729 | A1 | 9/2008 | Sullivan et al. | |
| 2009/0155351 | A1 | 6/2009 | Hejl et al. | |
| 2009/0232894 | A1 * | 9/2009 | Chouvenc | A61K 9/1623 424/489 |
| 2010/0068223 | A1 | 3/2010 | Scheffczik | |
| 2010/0178331 | A1 * | 7/2010 | Nagata | A61K 9/0043 514/1.1 |
| 2013/0273120 | A1 * | 10/2013 | Nagata | A61K 9/0043 424/400 |
| 2015/0017212 | A9 * | 1/2015 | Nagata | A61K 9/0043 424/400 |

FOREIGN PATENT DOCUMENTS

| | | | |
|---|---|---|---|
| AU | 2012244077 B2 | 6/2015 | |
| CN | 1370523 | 9/2002 | |
| CN | 101296705 | 10/2008 | |
| CN | 101601860 | 12/2009 | |
| EP | 2116264 A1 | 11/2009 | |
| EP | 2489348 A1 | 8/2012 | |
| JP | WO 2008078730 A1 * | 7/2008 | ........... A61K 9/0043 |
| WO | WO 2007/035455 A2 | 3/2007 | |
| WO | WO 2007/144724 A1 | 12/2007 | |

(Continued)

OTHER PUBLICATIONS

Fluvirin®. Influenza Virus Vaccine. 2008-2009 Formula. Novartis Vaccines and Diagnostics, Ltd. Jul. 2008.*
Quan FS, Kim YC, Yoo DG, Compans RW, Prausnitz MR, Kang SM. Stabilization of influenza vaccine enhances protection by microneedle delivery in the mouse skin. PLoS One. Sep. 25, 2009;4(9):e7152.*
Geeraedts F, Saluja V, ter Veer W, Amorij JP, Frijlink HW, Wilschut J, Hinrichs WL, Huckriede A. Preservation of the immunogenicity of dry-powder influenza H5N1 whole inactivated virus vaccine at elevated storage temperatures. AAPS J. Jun. 2010;12(2):215-22. doi: 10.1208/s12248-010-9179-z. Epub Mar. 2, 2010.*

(Continued)

*Primary Examiner* — Rachel B Gill
(74) *Attorney, Agent, or Firm* — Wilson, Sonsini, Goodrich & Rosati

(57) ABSTRACT

Provided herein are methods for generating dry vaccine powder formulations. Dry vaccine powder formulations can be used for intranasal delivery. Also provided are methods for stimulating local mucosal and systemic immunity by intranasal vaccine delivery.

22 Claims, 24 Drawing Sheets

(56) References Cited

FOREIGN PATENT DOCUMENTS

| WO | WO 2008/042789 A1 | 4/2008 |
|----|-------------------|--------|
| WO | WO 2008118691 A2 * | 10/2008 |
| WO | WO 2009/006299 A2 | 1/2009 |
| WO | WO 2010/012045 A1 | 2/2010 |

OTHER PUBLICATIONS

Coucke D, Schotsaert M, Libert C, Pringels E, Vervaet C, Foreman P, Saelens X, Remon JP. Spray-dried powders of starch and cross-linked poly(acrylic acid) as carriers for nasal delivery of inactivated influenza vaccine. Vaccine. Feb. 18, 2009;27(8):1279-86. Epub Dec. 27, 2008.*

Garmise RJ, Staats HF, Hickey AJ. Novel dry powder preparations of whole inactivated influenza virus for nasal vaccination. AAPS PharmSciTech. Oct. 12, 2007;8(4):E81.*

Hickey AJ, Garmise RJ. Dry powder nasal vaccines as an alternative to needle-based delivery. Crit Rev Ther Drug Carrier Syst. 2009;26(1)1 -27. Review.*

Lang R, Winter G, Vogt L, Zurcher A, Dorigo B, Schimmele B. Rational design of a stable, freeze-dried virus-like particle-based vaccine formulation. Drug Dev Ind Pharm. Jan. 2009;35(1):83-97.*

Ozsoy Y, Gungor S, Cevher E. Nasal delivery of high molecular weight drugs. Molecules. Sep. 23, 2009;14(9):3754-79.*

Purvis T, Mattucci ME, Crisp MT, Johnston KP, Williams RO 3rd. Rapidly dissolving repaglinide powders produced by the ultra-rapid freezing process. AAPS PharmSciTech. Jul. 20, 2007;8(3):E58.* de Jonge J, Amorij JP, Hinrichs WL, Wilschut J, Huckriede A, Frijlink HW. Inulin sugar glasses preserve the structural integrity and biological activity of influenza virosomes during freeze-drying and storage. Eur J Pharm Sci. Sep. 2007;32(1):33-44. Epub Jun. 2, 2007.*

Pires A, Fortuna A, Alves G, Falcão A. Intranasal drug delivery: how, why and what for? J Pharm Pharm Sci. 2009;12(3):288-311.*

Evans JC, Scherzer BD, Tocco CD. Preparation of nanostructured particles of poorly water soluble drugs via a novel ultra-rapid freezing technology. In: Svenson S, ed. Polymeric Drug Delivery vol. II—Polymeric Matrices and Drug Particle Engineering. New York, NY: American Chemical Society; 2004:2048Y2057.*

Tamura S. [Intranasal inactivated influenza vaccine]. Nihon Rinsho. Oct. 2006;64(10):1871-8. Review. Japanese. PubMed PMID: 17037362. English Translation.*

Greb, E. PharmTech.com. "Is Spray Drying a Viable Alternative to Lyophilization?" Pub. Dec. 16, 2009. http://www.pharmtech.com/spray-drying-viable-alternative-lyophilization.*

Huang J, Garmise RJ, Crowder TM, Mar K, Hwang CR, Hickey AJ, Mikszta JA, Sullivan VJ. A novel dry powder influenza vaccine and intranasal delivery technology: induction of systemic and mucosal immune responses in rats. Vaccine. Dec. 21, 2004;23(6):794-801.*

Amorij JP, Huckriede A, Wilschut J, Frijlink HW, Hinrichs WL. Development of stable influenza vaccine powder formulations: challenges and possibilities. Pharm Res. Jun. 2008;25(6):1256-73.*

Saluja V, Amorij JP, Kapteyn JC, de Boer AH, Frijlink HW, Hinrichs WL. A comparison between spray drying and spray freeze drying to produce an influenza subunit vaccine powder for inhalation. J Control Release. Jun. 1, 2010;144(2):127-33. Epub Feb. 25, 2010.*

Amorij JP, Meulenaar J, Hinrichs WL, Stegmann T, Huckriede A, Coenen F, Frijlink HW. Rational design of an influenza subunit vaccine powder with sugar glass technology: preventing conformational changes of haemagglutinin during freezing and freeze-drying. Vaccine. Aug. 29, 2007;25(35):6447-57. Epub Jul. 16, 2007.*

European search report and opinion dated Nov. 29, 2013 for EP Application No. 13189570.8.

European search report and opinion dated Jul. 30, 2013 for EP Application No. 11768642.8.

U.S. Appl. No. 13/828,337, filed Mar. 14, 2013, Nagata et al.

Chefson, et al. Sugar-mediated lyoprotection of purified human CYP3A4 and CYP2D6. J Biotechnol. Jul. 15, 2007;130(4):436-40. Epub May 23, 2007.

Amorij, et al. Development of stable influenza vaccine powder formulations: challenges and possibilities. Pharm Res. Jun. 2008;25(6):1256-73.

Flumist Influenza Vaccine Live, Intranasal 2009-2010 Formula, MedImmune, Sep. 2009.

Garmise, et al. Dry powder nasal vaccines as an alternative to needle-based delivery. Crit Rev Ther Drug Carrier Syst. 2009;26(1):1-27.

Garmise, et al. Formulation of a dry powder influenza vaccine for nasal delivery. AAPS PharmSciTech. Mar. 10, 2006;7(1):E1-7.

Hanson, et al. Introduction to formulation of protein pharmaceuticals. Plenum, New York. 1992; 209-233.

Holmgren, et al. Mucosal immunity and vaccines. Nature Medicine 11(4): S45-S53 (2005). Published online: ; | doi:10.1038/nm1213.

Huang, et al. A novel dry powder influenza vaccine and intranasal delivery technology: induction of systemic and mucosal immune responses in rats. Vaccine. Dec. 21, 2004;23(6):794-801.

International search report and written opinion dated Jul. 6, 2011 for PCT Application No. JP2011/002225.

Makino, et al. Pharmacokinetics of nasal powder formulations. Drug Deliv Syst. 2005; 20(6):656-665.

Saluja, et al. A comparison between spray drying and spray freeze drying to produce an influenza subunit vaccine powder for inhalation. J Control Release. Jun. 1, 2010;144(2):127-33. Epub Feb. 25, 2010.

Takada, et al. Intranasal immunization with formalin-inactivated virus vaccine induces a broad spectrum of heterosubtypic immunity against influenza A virus infection in mice. Vaccine. Jul. 4, 2003;21(23):3212-8.

Tamura, S. Intranasal inactivated influenza vaccine. Nippon Rinsho. Oct. 2006;64(10):1871-8. (in Japanese with English abstract).

Zhai, et al. Effect of freezing rates and excipients on the infectivity of a live viral vaccine during lyophilization. Biotechnol Prog. Jul.-Aug. 2004;20(4):1113-20.

Amorij, et al. The Development of Stable Influenza Vaccine Powder Formulations for New Needle-Free Dosage Forms. Thesis, Department of Pharmaceutical Technology and Biopharmacy, University of Groningen: 1-186 (2007).

Casiday, et al. Blood, Sweat and Buffers: pH regulation during exercise. Department of Chemistry, Washington University (2008).

Conlin, et al. The natural osmolyte trehalose is a positive regulator of the heat-induced activity of yeast heat shock transcription factor. Mol Cell Biol. Feb. 2007;27(4):1505-15. Epub Dec. 4, 2006.

Luukkonen, et al. Rheological characterization of microcrystalline cellulose and silicified microcrystalline cellulose wet masses using a mixer torque rheometer. Int J Pharm. Oct. 25, 1999;188(2):181-92.

Office action dated Sep. 4, 2014 for U.S. Appl. No. 13/828,337.

Pires, et al. Intranasal drug delivery: how, why and what for? J Pharm Pharm Sci. 2009;12(3):288-311.

Ruben. Inactivated influenza virus vaccines in children. Clin Infect Dis. Mar. 1, 2004;38(5):678-88. Epub Feb. 17, 2004.

Skopec, et al. Energetics for displacing a single chain from the surface of microcrystalline cellulose into the active site of Acidothermus cellulolyticus Ce15A. Protein Eng. Dec. 2003;16(12):1005-15.

Suzuki, et al. Mucosal drug delivery using cellulose derivatives as a functional polymer. Journal of Controlled Release. 1999; 62:101-107.

Tanimoto. Characteristic and Problem of Intranasal Vaccine. Drug Delivery System, Jan. 2010, vol. 25, No. 1, pp. 15-21. (in Japanese with partial English translation).

Ejikeme. Investigation of the physicochemical properties of microcrystalline cellulose from agricultural wastes I: orange mesocarp. Cellulose. 2008; 15:141-147.

Gardner, et al. Adhesion and Surface Issues in Cellulose and Nanocellulose. Journal of Adhesion Science and Technology. 2008; 22: 545-567.

Matsumoto, et al. Carbohydrates of influenza virus hemagglutinin: structures of the whole neutral sugar chains. Biochemistry. Jan. 4, 1983;22(1):188-96.

(56) References Cited

OTHER PUBLICATIONS

Office action dated Jul. 29, 2015 for U.S. Appl. No. 13/828,337.
Reier. Avicel PH Microcrystalline Cellulose, NF, Ph Eur., JP, BP. FMC, Section 11 (2000).
Office action dated Apr. 28, 2016 for U.S. Appl. No. 13/828,337.

* cited by examiner

Fig. 1

Conventional Freeze-Drying Process
(Slow freezing at -40 ºC for over 5 hours,
4 step freeze drying)

Flu vaccine (H1N1, whole, inactive) + Trehalose (specific amount) + Phosphate Buffer (specific concentration) → Flu vaccine powder

Properties
- Partially caked powder
- 100% HA potency
  → Stable

+ Mannitol (specific amount) + Phosphate Buffer (specific concentration) → Flu vaccine powder

Properties
- Fine particle
- 50% HA potency
  → Unstable

+ Lactose (specific amount) + Phosphate Buffer (specific concentration) → Flu vaccine powder

Properties
- Partially caked powder
- 85% HA potency
  → Stable

Fig. 3
Manufacturing Process of Vaccine Powder

A. Preparation of Vaccine Solution
   Materials a), b) and c) are mixed in a 10 mL glass bottle

| |
   |---|
   | a) Antigen Solution |
   | b) Stablizer (TREHALOSE, mannitol, or lactose) |
   | c) Phosphate buffer or ultra pure water |

B. Quick Freezing
   Vaccine Solution is frozen in liquid nitrogen for 10 minutes.

C. Drying in the frozen state
   Frozen Vaccine Solution is dried in freeze-dryer under the following conditions.

| |
   |---|
   | Step 1: -40 °C, less than 140 mtorr for 24h |
   | Step 2: -30 °C, less than 130 mtorr for 24-36h |
   | Step 3: -10 °C, less than 100 mtorr for 4h |
   | Step 4: 20 °C, less than 50 mtorr for 4h |

| |
   |---|
   | Vaccine Powder → fine particulate, antigenic |

D. Blending
   Materials a) to d) are placed in a 10 mL glass bottle and blended using a vortex mixer.

| | |
   |---|---|
   | A) | Vaccine Powder prepared |
   | B) | Ceolus® PH-F20JP, microcrystalline cellulose |
   | c) | Ceolus® PH-301, microcrystalline cellulose |
   | d) | tribasic calcium phosphate (TCP) |

| |
   |---|
   | Dry Nasal Vaccine Powder Formulation |

Fig. 4
Test Animal: Cynomolgus monkeys (similar anatomy of nasal cavity and similar immune response to humans)

| | Test Article | Administration Route | Dose (Total Protein) | Administration Schedule | Collected Samples | Sampling Schedule |
|---|---|---|---|---|---|---|
| Group 1 (n=3) | Nasal Flu Powder (H1N1 Vaccine) | Intranasal | 90µg/time | Day 0, 21, 35 and 49 | Serum (for IgG) Nasal wash (for IgA) | Day -7, 7, 14, 28, 42, 56 and 66 |
| Group 2 (n=3) | Nasal Flu vaccine solution | Intranasal | 90µg/time | Day 0, 21, 35 and 49 | Serum (for IgG) Nasal wash (for IgA) | Day -7, 7, 14, 28, 42, 56 and 66 |
| Group 3 (n=3) | Nasal Flu vaccine solution w/ adjuvant* | Intranasal | 90µg/time | Day 0, 21, 35 and 49 | Serum (for IgG) Nasal wash (for IgA) | Day -7, 7, 14, 28, 42, 56 and 66 |
| Group 4 (n=2) | SC Flu vaccine solution | SC injection | 90µg/time | Day 0, 21, 35 and 49 | Serum (for IgG) Nasal wash (for IgA) | Day -7, 7, 14, 28, 42, 56 and 66 |

*α-Galactosylceramide is a nasal adjuvant which is reported to be effective in mouse and rat studies.

Fig. 5A
HI titer in male cynomolgus monkeys, H1N1 Vaccine Test

| Group | Route | Animal Number | Serum, HI titer | | | | | | |
|---|---|---|---|---|---|---|---|---|---|
| | | | -7 | 7 | 14 | 28 | 42 | 56 | 66 |
| Group 1 | | 1 | 10 | 10 | 20 | 160 | 320 | 320 | 320 |
| nasal powder, -adj | i.n. | 2 | 10 | 10 | 20 | 40 | 40 | 80 | 80 |
| 90 µg/nostril/time | | 3 | 10 | 10 | 10 | 40 | 80 | 80 | 160 |
| | | | 10.0 | 10.0 | 15.9 | 63.5 | 100.8 | 127.0 | 160.0 |
| Group 2 | | 4 | 10 | 10 | 10 | 20 | 20 | 40 | 40 |
| nasal liquid, -adj | i.n. | 5 | 10 | 10 | 40 | 80 | 80 | 80 | 160 |
| 90 µg/nostril/time | | 6 | 10 | 10 | 20 | 40 | 40 | 40 | 40 |
| | | | 10.0 | 10.0 | 20.0 | 40.0 | 40.0 | 50.4 | 63.5 |
| Group 3 | | 7 | 10 | 10 | 20 | 20 | 20 | 40 | 40 |
| nasal liquid, +adj | i.n. | 8 | 10 | N | 10 | 10 | 20 | 20 | 20 |
| 90 µg/nostril/time | | 9 | 20 | 20 | 20 | 40 | 40 | 40 | 40 |
| | | | 12.6 | 14.1 | 15.9 | 20.0 | 25.2 | 31.7 | 31.7 |
| Group 4 | s.c. | 10 | 10 | 20 | 40 | 160 | 160 | 320 | 160 |
| SC injection, -adj | | 11 | 10 | 20 | 80 | 640 | 640 | 640 | 640 |
| 90 µg/time | | | | | | | | | |
| | | | 10.0 | 20.0 | 56.6 | 320.0> | 320.0> | 452.5> | 320.0> |

NS: No Sample

Fig. 5B
HI titer in male cynomolgus monkeys, H1N1 Vaccine Test

| Group | Route | Animal Number | Nasal wash (right), HI Titer | | | | | | |
|---|---|---|---|---|---|---|---|---|---|
| | | | -7 | 7 | 14 | 28 | 42 | 56 | 66 |
| Group 1 | i.n. | 1 | 10 | 10 | 10 | 10 | 10 | 10 | 20 |
| nasal powder, -adj | | 2 | 10 | 10 | 10 | 10 | 10 | 40 | 40 |
| 90 μg/nostril/time | | 3 | 10 | 10 | 10 | 10 | 40 | 80 | 80 |
| | | | 10.0 | 10.0 | 10.0 | 10.0 | 15.9 | 31.7 | 40.0 |
| Group 2 | i.n. | 4 | NS | 10 | 10 | 10 | 10 | 10 | 10 |
| nasal liquid, -adj | | 5 | 10 | 10 | 10 | 10 | 10 | 20 | 40 |
| 90 μg/nostril/time | | 6 | 10 | 10 | 10 | 10 | 10 | 10 | 10 |
| | | | 10.0 | 10.0 | 10.0 | 10.0 | 10.0 | 12.6 | 15.9 |
| Group 3 | i.n. | 7 | 10 | 10 | 10 | 10 | 10 | 10 | 20 |
| nasal liquid, +adj | | 8 | 10 | 10 | 10 | 10 | 10 | 10 | 10 |
| 90 μg/nostril/time | | 9 | 10 | 10 | 10 | 10 | 10 | 10 | 10 |
| | | | 10.0 | 10.0 | 10.0 | 10.0 | 10.0 | 10.0 | 12.6 |
| Group 4 | s.c. | 10 | 10 | 10 | 10 | 10 | 10 | 10 | 10 |
| SC injection, -adj | | 11 | 10 | 10 | 10 | 10 | 10 | 10 | 10 |
| 90 μg/time | | | | | | | | | |
| | | | 10.0 | 10.0 | 10.0 | 10.0 | 10.0 | 10.0 | 10.0 |

NS: No Sample

Fig. 6A
Antibody titer in male cynomolgus monkeys, H1N1 Vaccine Test

| Group | Route | Animal Number | Serum IgG | | | | | | |
|---|---|---|---|---|---|---|---|---|---|
| | | | -7 | 7 | 14 | 28 | 42 | 56 | 66 |
| Group 1 | | 1 | - | 128 | 256 | 4096 | 16384 | 16384 | 16384 |
| nasal powder, -adj | i.n. | 2 | - | 16 | 32 | 2048 | 2048 | 4096 | 4096 |
| 90 μg/nostril/time | | 3 | - | - | 32 | 1024 | 4096 | 4096 | 8192 |
| | | | - | 45.3 | 64.0 | 2048.0 | 5160.6 | 6502.0 | 8192.0 |
| Group 2 | | 4 | - | - | - | 512 | 1024 | 2048 | 2048 |
| nasal liquid, -adj | i.n. | 5 | - | - | 16 | 4096 | 4096 | 4096 | 4096 |
| 90 μg/nostril/time | | 6 | - | 32 | 256 | 1024 | 2048 | 2048 | 1024 |
| | | | - | 32.0 | 64.0 | 1290.2 | 2048.0 | 2580.3 | 2048.0 |
| Group 3 | | 7 | - | 16 | 16 | 64 | 512 | 1024 | 1024 |
| nasal liquid, +adj | i.n. | 8 | - | - | - | 256 | 256 | 512 | 512 |
| 90 μg/nostril/time | | 9 | - | - | 128 | 512 | 1024 | 1024 | 1024 |
| | | | - | 16.0 | 45.3 | 203.2 | 512.0 | 812.7 | 812.7 |
| Group 4 | s.c. | 10 | - | 16 | 1024 | 16384 | 16384 | 16384 | 16384 |
| SC injection, -adj | | 11 | - | 32 | 4096 | 65536 | 65536 | 65536 | 65536 |
| 90 μg/time | | | | | | | | | |
| | | | - | 23 | 2048 | 32768 | 32768 | 32768 | 32768 |

-: < cut off value

Fig. 6B
Antibody titer in male cynomolgus monkeys, H1N1 Vaccine Test

| Group | Route | Animal Number | Nasal wash (right), sIgA | | | | | | |
|---|---|---|---|---|---|---|---|---|---|
| | | | -7 | 7 | 14 | 28 | 42 | 56 | 66 |
| Group 1 | i.n. | 1 | - | 2 | 2 | 4 | 4 | 64 | 256 |
| nasal powder, -adj | | 2 | - | 2 | 2 | 2 | 32 | 128 | 256 |
| 90 μg/nostril/time | | 3 | - | 4 | - | 4 | 128 | 256 | 512 |
| | | | | 2.5 | 2.0 | 3.2 | 25.4 | 128.0 | 322.5 |
| Group 2 | i.n. | 4 | - | 2 | 4 | 4 | 16 | 64 | 128 |
| nasal liquid, -adj | | 5 | - | - | - | 2 | 32 | 64 | 256 |
| 90 μg/nostril/time | | 6 | 1 | 4 | 2 | 8 | 8 | 4 | 16 |
| | | | | 2.8 | 2.8 | 4.0 | 16.0 | 25.4 | 80.6 |
| Group 3 | i.n. | 7 | - | 8 | 4 | 8 | 16 | 32 | 128 |
| nasal liquid, -adj | | 8 | 1 | 4 | 4 | 8 | 16 | 16 | 16 |
| 90 μg/nostril/time | | 9 | - | 4 | 4 | 2 | 8 | 8 | 16 |
| | | | | 5.0 | 4.0 | 5.0 | 12.7 | 16.0 | 32.0 |
| Group 4 | s.c. | 10 | - | 4 | 2 | - | 4 | 2 | 8 |
| SC injection, -adj | | 11 | - | - | - | 2 | 8 | 4 | 4 |
| 90 μg/time | | | | | | | | | |
| | | | | 4.0 | 2.0 | 2.0 | 5.7 | 2.8 | 5.7 |

-: < cut off value

Each line represents the test results from one animal within the indicated test group Fig. 8
HI titer in male cynomolgus monkeys, H1N1 Vaccine Test

|  |  |  | Serum, HI | | | Nasal wash (right), HI | | |
|---|---|---|---|---|---|---|---|---|
| Group | Route | Animal Number | 80 | 101 | 115 | 80 | 101 | 115 |
| Group 1 nasal powder, -adj 90 μg /time | i.n. | 1 | 320 | 320 | 160 | 40 | 40 | 80 |
| Group 2 nasal liquid, -adj 90 μg /time | i.n. | 6 | 20 | 20 | 20 | 10 | 10 | 10 |
| Group 3 nasal liquid, +adj 90 μg /time | i.n. | 7 | 20 | 20 | 10 | 10 | 10 | 10 |
| Group 4 SC injection, -adj 90 μg/time | s.c. | 10 | 160 | 80 | 40 | 10 | 10 | 10 |
|  |  | 11 | 640 | 320 | 160 | 10 | 10 | NS |

NS: No sample

Fig. 9
Antibody titer in male cynomolgus monkeys, H1N1 Vaccine Test

|  |  |  | Serum IgG | | | Nasal wash (right), sIgA | | |
| --- | --- | --- | --- | --- | --- | --- | --- | --- |
| Group | Route | Animal Number | 80 | 101 | 115 | 80 | 101 | 115 |
| Group 1 nasal powder, -adj 90 μg/time | i.n. | 1 | 16384 | 16384 | 16384 | 256 | 512 | 512 |
| Group 2 nasal liquid, -adj 90 μg /time | i.n. | 6 | 1024 | 1024 | 1024 | 32 | 16 | 32 |
| Group 3 nasal liquid, +adj 90 μg/ time | i.n. | 7 | 512 | 512 | 256 | 64 | 64 | 64 |
| Group 4 SC injection, -adj 90 μg/time | s.c. | 10 | 8192 | 4096 | 2048 | 8 | 4 | 2 |
|  |  | 11 | 32768 | 16384 | 8192 | 4 | 2 | NS |

NS: No sample

Antibody titer (maximum dilution fold of sample showed higher absorbance than cut off value)

Fig. 10
Test Animal: Cynomolgus monkeys (similar anatomy of nasal cavity and similar immune response to humans)

| | Test Article | Administration Route | Dose (HA Protein) | Administration Schedule | Collected Samples | Sampling Schedule |
|---|---|---|---|---|---|---|
| Group 1 (n=5) | Nasal Flu Powder (H5N1) | Intranasal | 30 μg/time (15 μg/nostril) | Day 0, 14, 28 and 42 | Serum (for IgG) Nasal wash (for IgA) | Day -7, -1, 13, 20, 27, 34, 41, 48, 55, 62, and 69 |
| Group 2 (n=5) | Nasal Flu Spray (H5N1) | Intranasal | 30 μg/time (15 μg/nostril) | Day 0, 14, 28 and 42 | Serum (for IgG) Nasal wash (for IgA) | Day -7, -1, 13, 20, 27, 34, 41, 48, 55, 62, and 69 |
| Group 3 (n=3) | IM Flu vaccine Solution (H5N1) | IM injection | 30 μg/time | Day 0, 14, 28 and 42 | Serum (for IgG) Nasal wash (for IgA) | Day -7, -1, 13, 20, 27, 34, 41, 48, 55, 62, and 69 |

Fig. 11A
Antibody titer in male cynomolgus monkeys, H5N1 Vaccine Test

| Group | Route | Animal Number | Serum IgG | | | | | |
|---|---|---|---|---|---|---|---|---|
| | | | -1 | 13 | 27 | 41 | 55 | 70 |
| Group 1 | | 1 | - | - | - | 32 | 64 | 32 |
| Nasal Powder | i.n. | 2 | - | - | - | - | 16 | 32 |
| 30 μg Antigen | | 3 | - | - | - | 32 | 128 | 128 |
| (15 μg/nostril/time) | each nostril | 4 | - | - | 32 | 128 | 256 | 512 |
| | | 5 | - | - | 64 | 256 | 512 | 512 |
| | | | | | 45 | 76 | 111 | 128 |
| Group 2 | | 6 | - | - | - | 64 | 64 | 64 |
| Nasal Liquid | i.n. | 7 | - | - | - | - | - | - |
| 30 μg Antigen | | 8 | - | - | - | - | 32 | 32 |
| (15 μg/nostril/time) | each nostril | 9 | - | - | - | 16 | 32 | 32 |
| | | 10 | - | - | 16 | 32 | 64 | 64 |
| | | | | | 16 | 32 | 45 | 45 |
| Group 3 | | 11 | - | 256 | 2048 | 2048 | 8192 | 8192 |
| IM Injection | I.M. | 12 | - | 512 | 2048 | 2048 | 4096 | 4096 |
| 30 μg Antigen | | 13 | - | 512 | 2048 | 2048 | 8192 | 16384 |
| (30 μg/body/time) | | | | | | | | |
| | | | | | 2048 | 2048 | 6502 | 8192 |

-: < cut off value

Titers of serum IgG at Day 27 and 41 of IM Injection are more than 2048

Fig. 11B
Antibody titer in male cynomolgus monkeys, H5N1 Vaccine Test

| Group | Route | Animal Number | Nasal wash (right), sIgA | | | | | |
|---|---|---|---|---|---|---|---|---|
| | | | 1 | 13 | 27 | 41 | 55 | 70 |
| Group 1 | i.n. | 1 | - | - | - | 2 | 16 | 16 |
| Nasal Powder | | 2 | - | - | - | - | 2 | 2 |
| 30 μg Antigen | each nostril | 3 | - | - | 2 | 2 | 8 | 16 |
| (15 μg/nostril/time) | | 4 | - | - | - | 4 | 16 | 16 |
| | | 5 | - | 2 | 4 | 4 | 32 | 32 |
| | | | - | 2 | 3 | 3 | 11 | 12 |
| Group 2 | i.n. | 6 | - | - | - | - | - | - |
| Nasal Liquid | | 7 | - | 4 | - | - | - | - |
| 30 μg Antigen | each nostril | 8 | - | - | - | - | 2 | - |
| (15 μg/nostril/time) | | 9 | - | - | 2 | - | - | 4 |
| | | 10 | - | - | - | - | 2 | 2 |
| | | | - | 4 | 2 | - | 2 | 3 |
| Group 3 | I.M. | 11 | - | - | - | 2 | 2 | - |
| IM Injection | | 12 | - | - | - | - | - | - |
| 30 μg Antigen | | 13 | - | - | - | - | - | - |
| (30 μg/body/time) | | | | | | | | |
| | | | - | - | - | 2 | 2 | - |

-: < cut off value

Fig. 12
IgG (Serum)
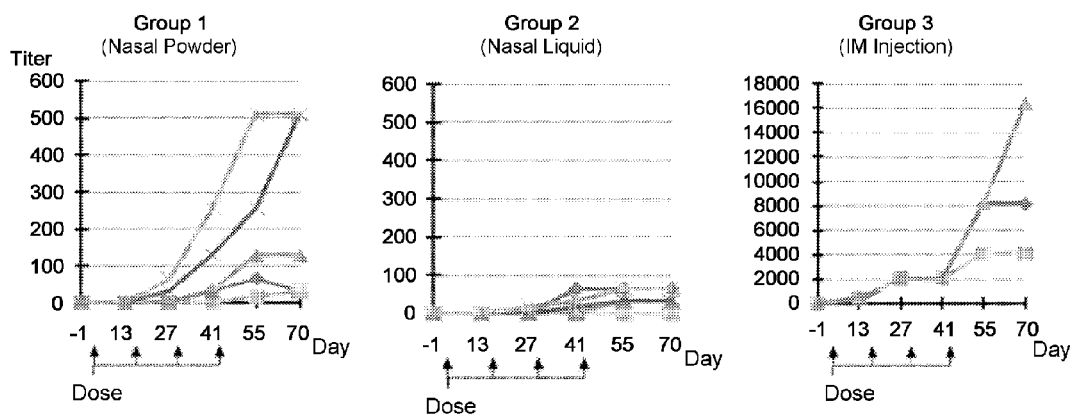
sIgA (Nasal Wash)
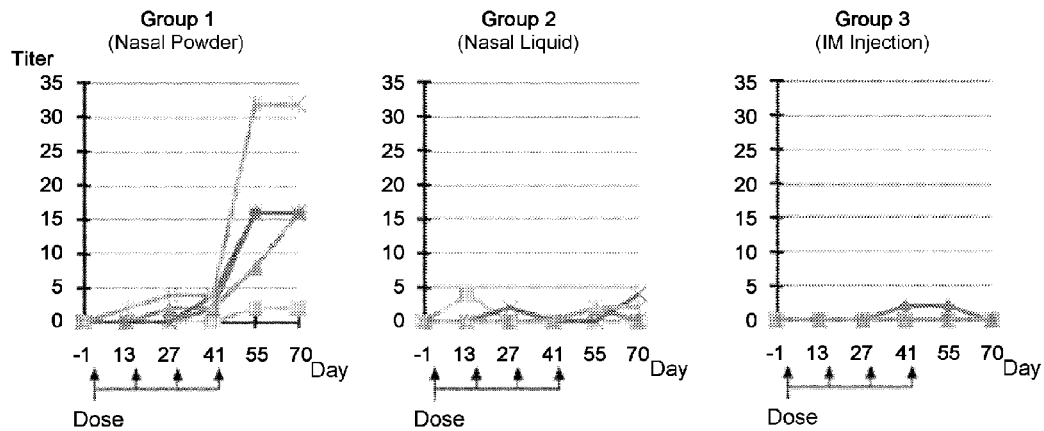
Each line represents the test results of one animal within the indicated test group Fig. 13
Test Animal: Cynomolgus monkeys (similar anatomy of nasal cavity and similar immune response to humans)

| | Test Article | Administration Route | Total Protein | Administration Schedule | Collected Samples | Sampling Schedule |
|---|---|---|---|---|---|---|
| Group 1 (n=1) | Nasal Powder (Tetanus Vaccine) | Intranasal | 5 Lf/time (2.5 Lf/nostril) | Day 0, 14, and 21 | Serum (for IgG) | Day -1, 13, 20, 27, and 34. |
| Group 2 (n=1) | Nasal Powder (Tetanus Vaccine) | Intranasal | 10 Lf/time (2.5 Lf/nostril X2) | Day 0, 14, and 21 | Serum (for IgG) | Day -1, 13, 20, 27, and 34. |
| Group 3 (n=1) | Nasal Powder (Tetanus Vaccine) | Intranasal | 20 Lf/time (2.5 Lf/nostril X4) | Day 0, 14, and 21 | Serum (for IgG) | Day -1, 13, 20, 27, and 34. |
| Group 4 (n=1) | Injected Liquid (Tetanus Vaccine) | SC injection | 10 Lf/time | Day 0, 14, and 21 | Serum (for IgG) | Day -1, 13, 20, 27, and 34. |

[Fig. 14A]
Absorbance ratio of serum IgG in male cynomolgus monkeys
Tetanus Toxoid Vaccine Test (TTx)

| | Absorbance ratio of serum IgG | | | | | | |
|---|---|---|---|---|---|---|---|
| Animal No. | | | | Day | | | |
| | Formulation | TTx | Base* | 13 | 20 | 27 | 34 |
| 1 | Nasal Powder | 5Lf | 1.00 | 0.87 | 1.07 | 1.00 | 0.94 |
| 2 | Nasal Powder | 10Lf | 1.00 | 0.99 | 0.96 | 0.96 | 0.88 |
| 3 | Nasal Powder | 20Lf | 1.00 | 1.29 | 1.08 | 4.33 | 7.88 |
| 4 | Injected Liquid | 10Lf | 1.00 | 14.12 | 56.23 | 53.58 | 59.33 |

* Base value (mean of Day -6 and -1) is adjusted to 1.00.

Fig. 14B
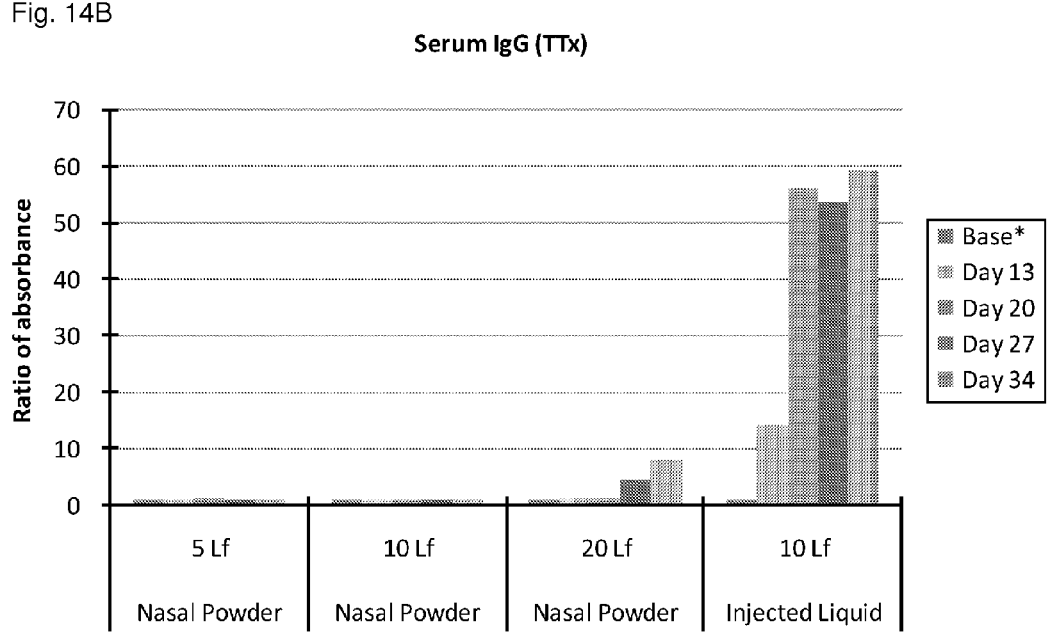
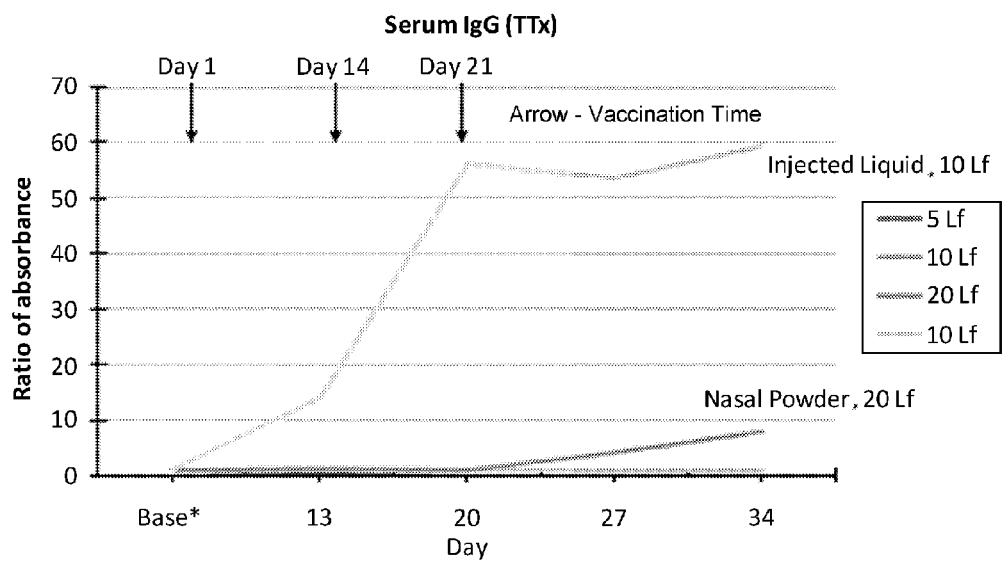

Fig. 15
The number of TTx-specific IFN gamma spot-forming cells in male cynomolgus monkeys
Tetanus Toxoid Vaccine Test (TTx)

| The number of TTx-specific IFN gamma spot-forming cells in serum ||||||||
| Animal No. | Formulation | TTx | Day ||||
| | | | 1 | 13 | 20 | 27 |
| 1 | Nasal Powder | 5 Lf | − | − | − | ⊥ |
| 2 | Nasal Powder | 10 Lf | − | − | − | ± |
| 3 | Nasal Powder | 20 Lf | − | − | ± | ++ |
| 4 | Injected Liquid | 10 Lf | − | = | + | + |

The level of positive signals was evaluated as: -, =, +, or −+.

[Fig. 16]
Test Animal: Cynomolgus monkeys (similar anatomy of nasal cavity and similar immune response to humans)

| | Test Article | Administration Route | Total Protein | Administration Schedule | Collected Samples | Sampling Schedule |
|---|---|---|---|---|---|---|
| Group 1 (n=1) |  Nasal Powder (Diphtheria Vaccine) | Intranasal | 2.5 Lf/time (1.25 Lf/nostril) | Day 0, 14, and 21 | Serum (for IgG) | Day -1, 13, 20, 27, and 34. |
| Group 2 (n=1) |  Liquid injection (Diphtheria Vaccine) | SC Injection | 5 Lf/time | Day 0, 14, and 21 | Serum (for IgG) | Day -1, 13, 20, 27, and 34. |
| Group 3 (n=1) |  Reconstituted Powder (Diphtheria Vaccine) | SC Injection | 5 Lf/time | Day 0, 14, and 21 | Serum (for IgG) | Day -1, 13, 20, 27, and 34. |

Fig. 17A
Absorbance ratio of serum IgG in male cynomolgus monkeys
Diphtheria Vaccine Test (DTx)
| Absorbance ratio of serum IgG | | | | | | | |
|---|---|---|---|---|---|---|---|
| Animal No. | Formulation | DTx | Day | | | | |
| | | | Base* | 13 | 20 | 27 | 34 |
| 1 | Nasal Powder | 2.5Lf | 1.00 | 2.72 | 3.88 | 4.54 | 4.54 |
| 2 | Injected Liquid | 5.0Lf | 1.00 | 0.96 | 1.32 | 1.89 | 2.85 |
| 3 | Reconst. Powder# | 5.0Lf | 1.00 | 1.11 | 2.24 | 5.44 | 7.45 |
* Base value (mean of Day -6 and -1) is adjusted to 1.00.
Reconstituted Powder. Condition of FreezeDry is same as nasal powder.
Fig. 17B
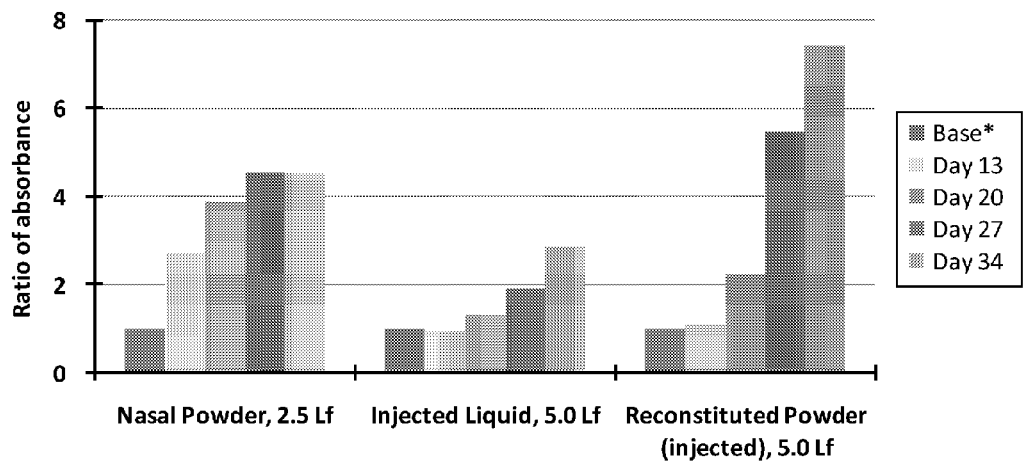
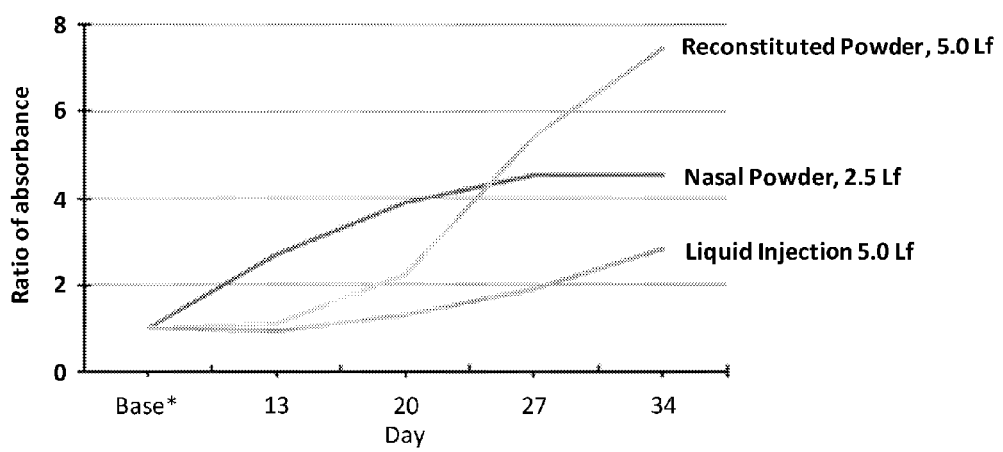

Fig. 18
Test Animal: Cynomolgus monkeys (similar anatomy of nasal cavity and similar immune response to humans

|  | Test Article | Administration Route | Total Protein | Administration Schedule | Collected Samples | Sampling Schedule |
|---|---|---|---|---|---|---|
| Group 1 (n=1) | Nasal Powder (hOVA) | Intranasal | 2 mg/time (1 mg/nostril) | Day 0, 14, 28, and 42 | Serum (for IgG) Nasal Wash (for sIgA) | Day -7, -1, 13, 27, 41, and 55. |
| Group 2 (n=1) | Nasal Powder (hOVA) | Intranasal | 10 mg/time (5 mg/nostril) | Day 0, 14, 28, and 42 | Serum (for IgG) Nasal Wash (for sIgA) | Day -7, -1, 13, 27, 41, and 55. |
| Group 3 (n=1) | Nasal Powder (hOVA) | Intranasal | 30 mg/time (15 mg/nostril) | Day 0, 14, 28, and 42 | Serum (for IgG) Nasal Wash (for sIgA) | Day -7, -1, 13, 27, 41, and 55. |
| Group 4 (n=1) | Nasal Liquid (hOVA) | Intranasal | 20 mg/time (10 mg/nostril) | Day 0, 14, 28, and 42 | Serum (for IgG) Nasal Wash (for sIgA) | Day -7, -1, 13, 27, 41, and 55. |
| Group 5 (n=1) | Nasal Liquid (hOVA) | Intranasal | 30 mg/time (15 mg/nostril) | Day 0, 14, 28, and 42 | Serum for IgG Nasal Wash (for sIgA) | Day -7, -1, 13, 27, 41, and 55. |
| Group 6 (n=1) | Injected Liquid (hOVA) | SC Injection | 20 mg/time | Day 0, 14, 28, and 42 | Serum (for IgG) Nasal Wash (for sIgA) | Day -7, -1, 13, 27, 41, and 55. |
| Group 7 (n=1) | Injected Liquid (hOVA) | SC Injection | 30 mg/time | Day 0, 14, 28, and 42 | Serum (for IgG) Nasal Wash (for sIgA) | Day -7, -1, 13, 27, 41, and 55. |

Fig. 19A
Antibody titer of serum IgG in Female cynomolgus monkeys
homogenized Ovalbumin (hOVA)

| Titer of serum IgG | | | | | | | |
|---|---|---|---|---|---|---|---|
| Animal No. | Formulation | hOVA | Day | | | | |
| | | | 0 | 14 | 28 | 42 | 56 |
| 1 | Nasal, Powder | 2 mg | – | N.D. | 80 | 320 | 320 |
| 2 | Nasal, Powder | 10 mg | – | 640 | 10240 | 10240 | 10240 |
| 3 | Nasal, Powder | 30 mg | – | 2560 | 10240 | 10240 | 10240 |
| 4 | Nasal, Liquid | 20 mg | – | N.D. | N.D. | N.D. | N.D. |
| 5 | Nasal, Liquid | 30 mg | | N.D. | N.D. | N.D. | N.D. |
| 6 | Injected, Liquid | 20 mg | – | 160 | 2560 | 10240 | 10240 |
| 7 | Injected, Liquid | 30 mg | – | 320 | 5120 | 10240 | 10240 |

Antibody titer (maximum dilution fold of sample showed higher absorbance than cut off value)

Fig. 19B
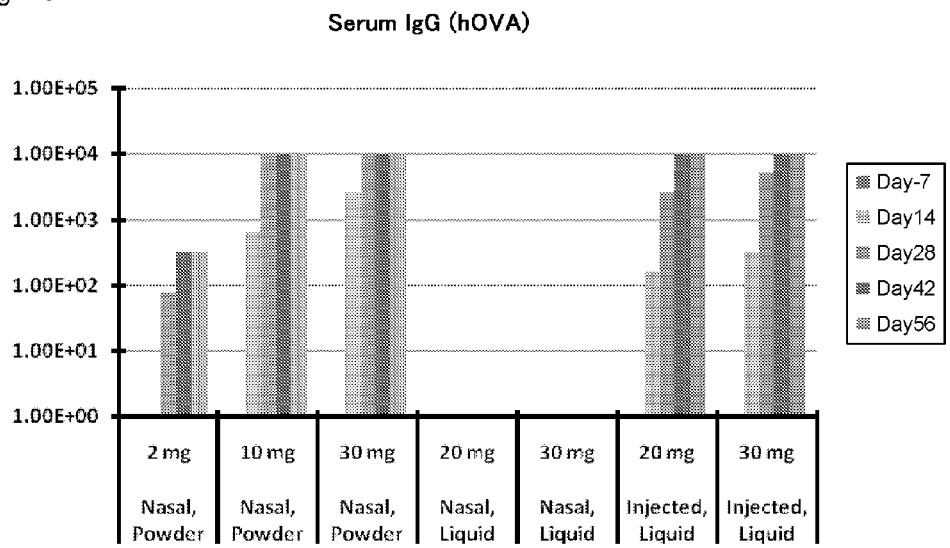
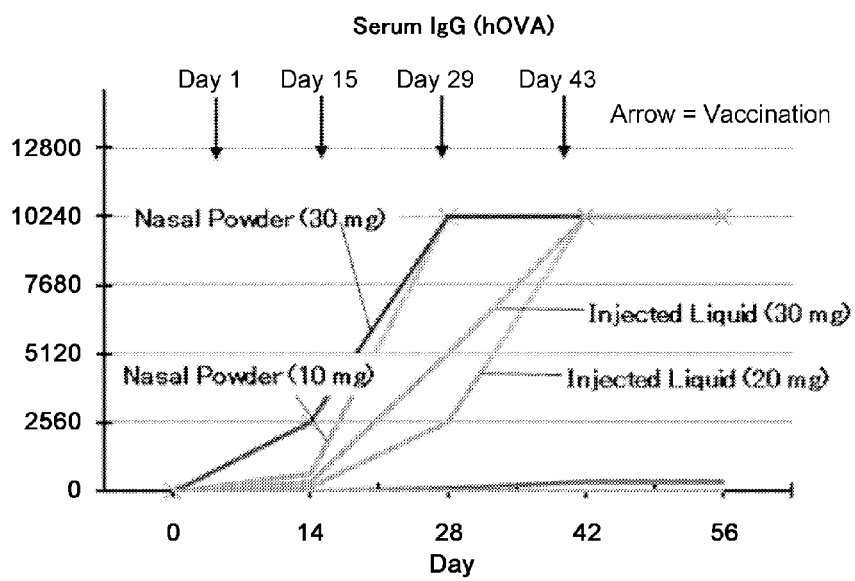

Fig. 20A
(A) Antibody titer of nasal wash sigA in female cynomolgus moneys homogenized Ovalbumin (hOVA)

| Titer of left nasal wash sIgA | | | | | | | |
|---|---|---|---|---|---|---|---|
| Animal No. | Formulation | hOVA | Day | | | | |
| | | | 0 | 14 | 28 | 42 | 56 |
| 1 | Nasal, Powder | 2 mg | – | – | – | – | 4 |
| 2 | Nasal, Powder | 10 mg | – | – | 32 | 64 | 32 |
| 3 | Nasal, Powder | 30 mg | | 8 | 16 | 16 | 16 |
| 4 | Nasal, Liquid | 20 mg | – | – | – | – | – |
| 5 | Nasal, Liquid | 30 mg | – | – | – | – | – |
| 6 | Injected, Liquid | 20 mg | – | – | – | – | – |
| 7 | Injected, Liquid | 30 mg | – | – | – | – | – |

Antibody titer (maximum dilution fold of sample showed higher absorbance than cut off value)

Fig. 20B
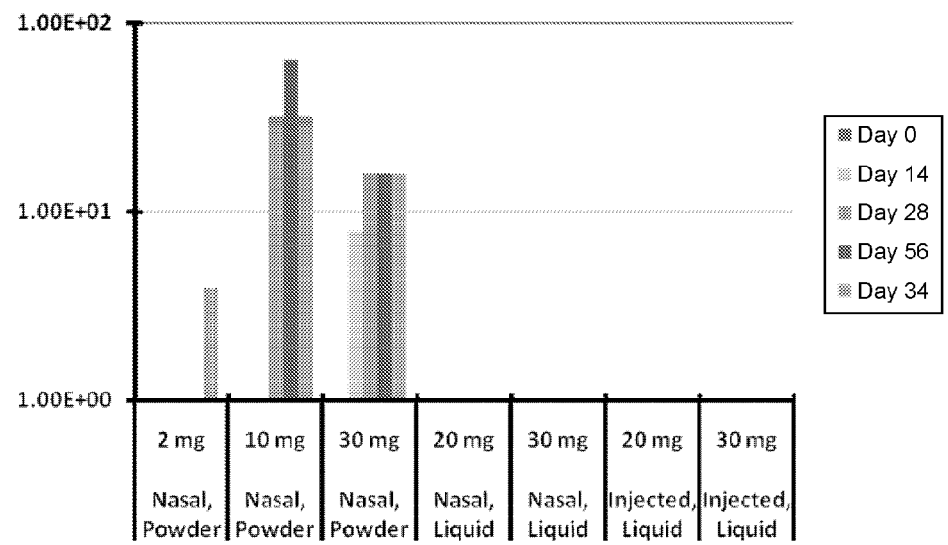
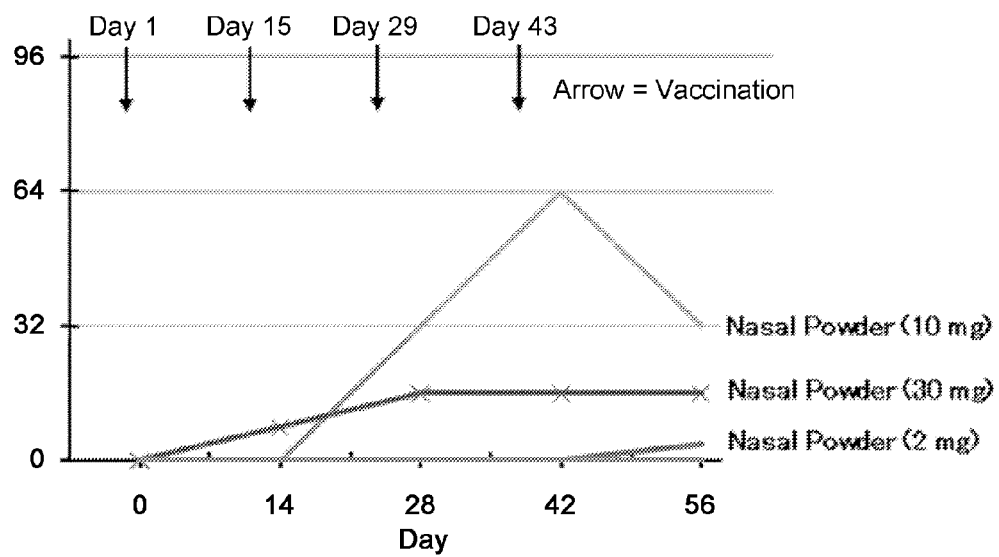

METHODS AND COMPOSITIONS FOR INTRANASAL DELIVERY

TECHNICAL FIELD

This application is the National Stage of International Application No. PCT/JP2011/002225, filed Apr 15, 2011, which claims the benefit of U.S. provisional application Ser. No. 61/324,542, filed Apr 15, 2010, which are incorporated herein by reference in their entirety.

Background Art

Influenza vaccines formulated as liquids can be subject to chemical degradation, e.g., aggregation, denaturation, hydrolysis, and oxidation that can result in their inactivation. Liquid vaccine formulations can also be sensitive to temperature: high temperatures can increase inactivation, and freezing temperatures can result in ice that can damage antigen in the vaccine. Thus, to prevent inactivation, liquid vaccines are often stored and distributed in a temperature range between 2 and 8 degrees C. Such storage can be costly, both for long-term storage and transportation of vaccines, and from loss of vaccine due to expiration. Generation of vaccines that are stable at room temperature would result in savings with respect to storage and would facilitate stockpiling. There is a need for means of generating vaccine formulations that are stable at room temperature, such as dry powder vaccines.

Several methods of freeze-drying vaccines have been described. For example, lyophilization (freeze-drying) of influenza vaccine solution can be used to generate a vaccine powder. However, the influenza vaccine powder produced by this method can be a hard cake, which does not facilitate consistent and reliable administration. Spray-freeze-drying (SFD) of an influenza vaccine solution can provide fine particles of influenza vaccine powder; however, SFD is a high-cost method. Thus, there is a need for low-cost methods of generating fine powder vaccines with relatively high flowability and relatively low hygroscopicity.

The mode of administration of a vaccine can play a role in its efficacy. One mode of administration, nonparental administration (e.g., nasal), can induce and promote mucosal and systemic humoral and cell mediated immune responses. Mucosal vaccination can result in induction of secretory IgA (sIgA) responses in the respiratory tract and oropharyngeal region. One feature of mucosal sIgA antibodies is that they can provide cross-protection against antigenically distinct viruses; thus, mucosal sIgA responses have the potential to provide protection against a viral strain that has drifted from the strain used to generate the vaccine (for example, influenza virus H1N1 can drift to H2N1 or H1N2). Furthermore, sIgA can help bind a virus or other pathogen at the mucosal surface, preventing access of the pathogen to deeper tissues and/or decreasing the likelihood of full-blown infection. Described herein are novel methods for generating an sIgA inducing vaccine, for example, a powder vaccine formulation for nonparental administration.

SUMMARY OF INVENTION

Disclosed herein is a dry vaccine powder formulation comprising: one or more antigens, one or more saccharides, one or more buffers; and microcrystalline cellulose. An antigen in a vaccine powder formulation described herein can be a viral antigen. A viral antigen can be live attenuated virus, whole inactivated virus, split-inactivated virus, subunit antigens, virosome, or cold-adapted live influenza virus. A viral antigen can be influenza virus; for example, an antigen could H1N1; or H5N1; or a mixture of H1N1, H3N2 and Influenza type B. An antigen in a vaccine powder formulation described herein can be a bacterial antigen. A bacterial antigen can be killed whole bacteria, attenuated bacteria, toxoids, purified surface protein, or purified recombinant surface protein. A bacterial antigen can be tetanus toxoid or diphtheria toxoid. An antigen in the dry vaccine powder formulation can also be a protist. An antigen could also be protein. The saccharide used can be trehalose, mannitol, or lactose. The saccharide used can be trehalose. The buffer used can be a phosphate buffer. A vaccine powder formulation described herein can be stable at room temperature and 60% relative humidity for at least 12 months.

Also provided herein is a method for generating a dry vaccine powder formulation comprising: preparing a liquid formulation comprising an antigen; quick freezing said liquid formulation, wherein the quick freezing does not comprise spray freezing; blending the freeze-dried sample with one or more excipients to generate the dry vaccine powder formulation. A viral antigen can be live attenuated virus, whole inactivated virus, split-inactivated virus, subunit antigens, virosome, or cold-adapted live influenza virus. A viral antigen can be influenza virus; for example, an antigen could H1N1; or H5N1; or a mixture of H1N1, H3N2 and Influenza type B. An antigen in a vaccine powder formulation described herein can be a bacterial antigen. A bacterial antigen can be killed whole bacteria, attenuated bacteria, toxoids, purified surface protein, or purified recombinant surface protein. A bacterial antigen can be tetanus toxoid or diphtheria toxoid. An antigen in the dry vaccine powder formulation can also be a protist. An antigen could also be protein. The preparation of a liquid formulation can comprise addition of a saccharide, for example trehalose, mannitol, or lactose. Preparation of a liquid formulation can also comprise addition of a buffer, such as a phosphate buffer. The powder can comprise fine particles. The powder can be stable at room temperature and 60% relative humidity for at least 12 months. Excipients useful in methods described herein can comprise one or more nasal carriers, such as microcrystalline cellulose and tribasic calcium phosphate. An excipient can improve flowability of the powder and/or reduce hygroscopicity of the powder. Some vaccine powders produced by a method herein do not comprise an adjuvant. Quick freezing can comprise the use of liquid nitrogen.

Another method provided herein is a method of stimulating an sIgA response in a subject to an antigen comprising administering a dry vaccine powder formulation to a subject, wherein the dry powder formulation comprises the antigen and wherein the dry powder formulation is generated by quick freezing a liquid vaccine formulation, wherein the quick freezing does not comprise spray-freezing. In some instances, an IgG response is also stimulated. sIgA production can be stimulated at the site of administration and/or at a mucosal site other than the site of administration. Administration can be intranasal. An antigen in a vaccine powder formulation described herein can be a viral antigen. A viral antigen can be live attenuated virus, whole inactivated virus, split-inactivated virus, subunit antigens, virosome, or cold-adapted live influenza virus. A viral antigen can be influenza virus; for example, an antigen could H1N1; or H5N1; or a mixture of H1N1, H3N2 and Influenza type B. An antigen in a vaccine powder formulation described herein can be a bacterial antigen. A bacterial antigen can be killed whole bacteria, attenuated bacteria, toxoids, purified surface protein, or purified recombinant surface protein. A bacterial antigen can be tetanus toxoid or diphtheria toxoid. An antigen in the dry vaccine powder formulation can also be a protist. An antigen could also be protein. The preparation of a liquid formulation can comprise addition of a saccharide, for example trehalose, mannitol or lactose. Preparation of a liquid formulation can also comprise addition of a buffer, such as a phosphate buffer. The powder can comprise fine particles. The powder can be stable at room temperature and 60% relative humidity for at least 12 months. Excipients useful in methods described herein can comprise one or more nasal carriers, such as microcrystalline cellulose and tribasic calcium phosphate. An excipient can improve flowability of the powder and/or reduce hygroscopicity of the powder.

Also provided herein is a device for administration of a vaccine powder formulation disclosed herein. Such a device can be configured for a single use.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1 illustrates properties of influenza vaccine powders generated using conventional slow freezing and freeze-drying processing with trehalose, mannitol and lactose.

FIG. 3 illustrates an embodiment of a manufacturing process of the provided invention.

FIG. 4 illustrates a study design for testing a H1N1 nasal influenza vaccine powder formulation.

FIG. 5A tabulates HI titers measured in serum samples collected during a test of a H1N1 nasal influenza vaccine powder formulation.

FIG. 5B tabulates HI titers measured in nasal wash samples collected during a test of a H1N1 nasal influenza vaccine powder formulation.

FIG. 6A tabulates serum IgG antibody titers measured in samples collected during a test of a H1N1 nasal influenza vaccine powder formulation.

FIG. 6B tabulates nasal wash sIGA antibody titers measured in samples collected during a test of a H1N1 nasal influenza vaccine powder formulation.

FIG. 8 tabulates HI titers measured in serum and nasal wash samples collected during a test of a H1N1 nasal influenza vaccine powder formulation.

FIG. 9 tabulates serum IgG and nasal wash sIgA antibody titers measured in samples collected during a test of a H1N1 nasal influenza vaccine powder formulation.

FIG. 10 illustrates a study design for testing a H5N1 nasal influenza vaccine powder formulation.

FIG. 11A tabulates serum IgG antibody titers measured in samples collected during a test of a H5N1 nasal influenza vaccine powder formulation.

FIG. 11B tabulates nasal wash sIgA antibody titers measured in samples collected during a test of a H5N1 nasal influenza vaccine powder formulation.

FIG. 12 graphically illustrates IgG and sIgA antibody titers measured during a test of a H5N1 nasal influenza vaccine powder formulation.

FIG. 13 illustrates a study design for testing a Tetanus toxoid nasal vaccine powder formulation.

FIG. 14A tabulates the absorbance ratio of serum IgG measured in samples collected during a test of a Tetanus toxoid nasal vaccine powder formulation FIG. 14B graphically illustrates the absorbance ratio of serum IgG measured in samples collected during a test of a Tetanus toxoid nasal vaccine powder formulation FIG. 15 tabulates IFN gamma levels measured in samples collected during a test of a Tetanus toxoid nasal vaccine powder formulation.

FIG. 16 illustrates a study design for testing a Diphtheria toxoid nasal vaccine powder formulation.

FIG. 17A tabulates serum IgG antibody titers measured in samples collected during a test of a Diphtheria toxoid nasal vaccine powder formulation.

FIG. 17B graphically illustrates serum IgG antibody titers measured in samples collected during a test of a Diphtheria toxoid nasal vaccine powder formulation.

FIG. 18 illustrates a study design for testing a homogenized ovalbumin nasal vaccine powder formulation.

FIG. 19A tabulates serum IgG antibody titers measured in samples collected during a test of a homogenized ovalbumin nasal vaccine powder formulation.

FIG. 19B graphically illustrates serum IgG antibody titers measured in samples collected during a test of a homogenized ovalbumin nasal vaccine powder formulation.

FIG. 20A tabulates nasal wash sIgA antibody titers measured in samples collected during a test of a homogenized ovalbumin nasal vaccine powder formulation.

FIG. 20B graphically illustrates nasal wash sIgA antibody titers measured in samples collected during a test of a homogenized ovalbumin nasal vaccine powder formulation.

DESCRIPTION OF EMBODIMENTS

Detailed Description of the Invention

I. Overview

Figure 2:
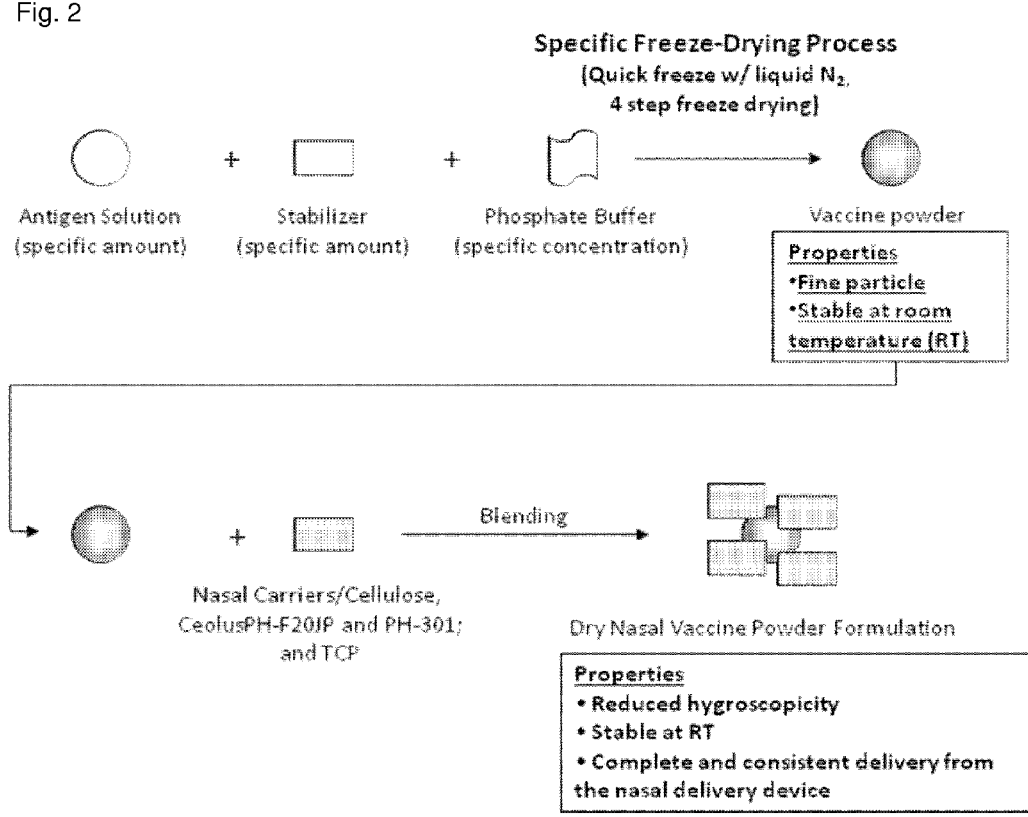
FIG. 2 illustrates a process for preparing a dry nasal vaccine powder formulation by quick freezing with liquid nitrogen. Exemplary properties of powders before and after addition of nasal carriers are also described.

Conventional freeze-drying processes for liquid influenza vaccine formulations, such as cooling from room temperature to −40 degrees C. over 24 hr, can lead to suboptimal particle properties or loss of antigenic (e.g. influenza hemagglutinin (HA)) potency (FIG. 1). For example, liquid influenza vaccine formulations with trehalose that are subjected to a conventional freeze-drying process can form a partially caked powder (FIG. 1). Liquid influenza vaccine formulations with mannitol that are subjected to a conventional freeze-drying process can have reduced HA potency (FIG. 1). Liquid influenza vaccine formulations with lactose that are subjected to a conventional freeze-drying process can form a partially caked powder and can have reduced HA potency (FIG. 1).

The present disclosure provides methods comprising a quick freezing step for generating a dry vaccine powder formulation (see e.g., FIGS. 2 and 3) which overcomes the limitations of previous freeze drying methods, resulting in high potency powdered vaccines with high flowability. The methods can comprise a step of generating a liquid formulation containing one or more antigens, such as a pathogen or a component thereof (e.g., a whole inactivated influenza virus) with one or more agents (e.g., a saccharide and/or buffer, e.g., phosphate buffer). A liquid vaccine formulation can be freeze-dried (e.g., comprising quick freezing in liquid nitrogen) to generate a powder (e.g., a vaccine powder). The powder can comprise fine particles and can be stable at room temperature. If the antigen is an influenza virus, the powder can have high HA potency (e.g., at least about 90%, 91%, 92%, 93%, 94%, 95%, 96%, 97%, 98%, 99%, or 100%). After freeze drying, the powder can be blended (e.g., by vortexing) with one or more excipients (e.g., nasal carriers and/or flowability agents) to form a dry vaccine powder formulation.

A dry vaccine powder formulation described herein can be stable at room temperature. This is an advance over liquid influenza vaccines, which are unstable at room temperature and can require expensive storage and distribution under refrigerated conditions (e.g., cold-chain distribution). In some vaccine preparations, a liquid formulation containing disaccharides, for example, trehalose or lactose, is prepared. Such additives generally allow for maintenance of HA potency of a dry influenza vaccine powder formulation. Although the use of such component saccharides is known, the methods described herein can provide a dry vaccine form which does not form hard cakes using these saccharide components. Hard caking can be avoided using the buffers and quick freezing techniques described herein. The powders produced from quick frozen and dried antigen preparations can then be combined with one or more excipients, such as a nasal carrier (e.g., microcrystalline cellulose) and/or a flowability agent (e.g., tribasic calcium phosphate). The present formulations can result in dry powder vaccines suitable for intranasal delivery which can be stable at room temperature and under accelerated conditions. A dry vaccine powder formulation provided herein can afford complete and consistent delivery from a nasal delivery device and result in stimulation of the recipient's immune response to the antigen/pathogen to which the vaccine is directed The methods provided herein can allow for reducing hygroscopicity and improving the flowability of a dry vaccine powder formulation provided herein. The methods can include addition of a physiologically acceptable agent (e.g., microcrystalline cellulose) to a powder formulation to reduce hygroscopicity and improve flowability of a dry vaccine powder formulation.

Methods provided herein can allow for improving the efficacy of a vaccine. The methods can comprise steps for generating a dry vaccine powder compositions that can stimulate a local immune response, for example, a mucosal immune response (e.g., involving mucosal sIgA). sIgA can provide cross-protection against mutated influenza viruses (e.g., a dry vaccine powder formulation can be used as a pandemic influenza vaccine) and/or viruses which have undergone genetic drift. A dry vaccine powder formulation, e.g., a dry nasal influenza powder formulation, can induce protection in distal mucosal sites. For example, introduction of a vaccine of the present disclosure at the nasal mucosa can lead to protection (e.g., sIgA production in the upper respiratory tract, the lower respiratory tract, the gastrointestinal tract, and vagina). A dry vaccine powder formulation can stimulate a systemic immune response (e.g., producing serum IgG). Dry vaccine powder compositions can comprise microcrystalline cellulose. In some embodiments, a dry vaccine powder formulation does not comprise adjuvant.

II. Liquid Formulations for Use in Generating a Powder Formulation

To generate a dry vaccine powder formulation, a liquid formulation can be first generated. The liquid formulation can comprise one or more antigens (e.g., one or more pathogens or components of pathogens), one or more saccharides, one or more buffers, and one or more other components. Typically, the liquid formulation is subjected to quick freezing (e.g., by immersion in liquid nitrogen) and freeze-drying prior to producing the dry vaccine powder formulation.

The volume of the liquid formulation can be about 0.1 mL, 1.0 mL, 10 mL, 25 mL, 50 mL, 100 mL, 250 mL, 500 mL, 1 L, 10 L, 50 L, 100 L, 250 L, 500 L, or 1000 L. The volume of the liquid formulation can be more than about 0.1 mL, 1.0 mL, 10 mL, 25 mL, 50 mL, 100 mL, 250 mL, 500 mL, 1 L, 10 L, 50 L, 100 L, 250 L, 500 L, or 1000 L. The volume of the liquid formulation can be about 0.01-1 mL, about 1-10 mL, about 10-50 mL, about 50-100 mL, about 1-1000 mL, about 100-1000 mL, about 1-10 L, about 10-50 L, about 50-100 L, about 100-500 L, about 100-1000 L, or about 1-1000 L. Following freeze drying, the amount of dry vaccine produced can be between about 0.05 mg to 500 mg, about 0.0.05 mg to 1 mg, about 1 mg to about 100 mg, or about 100 mg to about 500 mg.

A. Viral Vaccine Components

The methods of generating a dry vaccine powder formulation described herein can be used to produce a vaccine with a live attenuated virus, whole inactivated virus, split virus, subunit antigen, virosome, or cold-adapted live influenza virus.

The methods of generating a dry vaccine powder formulation described herein can be used to produce a vaccine with a live attenuated virus. Live attenuated vaccines can be derived from serial passage in cultured cells, including, for example, human diploid cells (e.g. fetal lung tissue, other fibroblasts), monkey kidney cells, and chick embryos. Adaptation of a virus to growth in the cultured cells can be accompanied by a gradual loss of virulence for the natural host. Avirulence can be conferred, e.g., by accumulation of point mutations. Genetic engineering can be used to achieve viral attenuation by, e.g., generating temperature sensitive mutants, generating deletion mutants, site-directed mutagenesis, or generating live recombinant viruses.

The methods of generating a dry vaccine powder formulation described herein can be used to produce a vaccine with a whole inactivated virus. Inactivated viruses can be generated, for example, by using ultraviolet light, low pH (e.g., acid, e.g., caprylic acid), pasteurization, solvents/detergents, sodium thiocyanate, formalin, beta-propiolactone, or ethylenimines. UV rays can damage DNA through by creating nucleic acid dimers, which can inactivate viruses by preventing the replication of genetic material. Some viruses denature upon exposure to low pH solutions. This method can be particularly effective when employed verses enveloped viruses. Pasteurization can inactivate viruses by means of temperature induced denaturation. Solvent/detergent inactivation is only effective against viruses enveloped in a lipid coat. The detergent used is typically Triton-X 100. Sodium thiocyanate can denature the protein coat of viruses, rendering the virus inactive. Formalin can chemically modify the surface proteins of the viral coat, which can prevent infection. Ethylenimines and beta-propiolactone can act on the nucleic acids of the virus while leaving the protein coat mostly unmodified. Inactivation can destroy infectivity of the virus while maintaining its immunogenicity. Multiple applications of inactivated virus can be administered to a subject.

The methods of generating a dry vaccine powder formulation described herein can be used to produce a vaccine with one or more antigenic proteins (vaccine proteins) from one or more pathogens. An antigenic protein can be from any pathogen to which a vaccine is to be produced. For example, where the vaccine is to target influenza virus, an antigenic protein can be hemagglutinin (HA) and/or neuraminidase (NA). Hemagglutinin is an antigenic glycoprotein and a major surface protein of the influenza A virus. It mediates the biding between an influenza virus and the cell to be infected by binding to sialic acid-containing receptors on the surface of the cell. Viral particles bound to the surface of the cell are engulfed into endosomes. Inside the endosome, HA mediates a fusion of the viral membrane and the endosomal membrane, releasing the viral genome into the cell. Structurally, HA consists of three identical monomers organized into a helical coil. A function blocking antibody could inhibit either the cell binding or membrane fusing functions of HA. Neuraminidase is another glycoprotein found on the surface of an influenza virus. NAs are enzymes that function by cleaving sialic acid groups from glycoproteins. This cleavage seems to serve two functions: to prevent viral clumping and to release progeny viruses from the surface of a cell.

There are at least 16 known HA subtypes. A vaccine antigen can be HA1, HA2, HA3, HA4, HA5, HA6, HA7, HA8, HA9, HA10, HA11, HA12, HA13, HA14, HA15, or HA16. There are 9 known NA subtypes. A vaccine antigen can be NA1, NA2, NA3, NA4, NA5, NA6, NA7, NA8, or NA9. A vaccine prepared from a HA and/or NA subtype can be used individually or in any combination. For example, two or more of the various HA and NA antigens can be mixed during manufacture of a dry vaccine powder formulation, or dry powder formulations of individual HA and NA antigens can be combined. An antigenic protein can be surface proteins from the pathogen. An antigenic protein can be produced recombinantly. For example, nucleic acid encoding an antigen of interest can be introduced in a prokaryotic cell (e.g. bacteria), eukaryotic cells (e.g., yeast cells and insect cells), and the protein can be expressed and purified from the cells. Where the pathogen is a virus, nonessential components of a virion can be removed (e.g., using ether and detergents).

The methods of generating a dry vaccine powder formulation described herein can be used to produce a virosomal vaccine. A virosomal vaccine comprises virus-like particles of reconstituted virus envelopes with no genetic material of the native virus. Influenza virosomes are vesicles consisting of a unilamellar phospholipid bilayer with intercalated HA and NA proteins. Because they have no genetic material, virosomes are not infectious.

The concentration of a vaccine protein (e.g., antigen or antigen containing component) in a liquid vaccine formulation can be from about 0.05 mg/mL to 10 mg/mL, about 0.1 mg/mL to 10 mg/mL, about 0.1 mg/mL to 5 mg/mL, about 0.1 mg/mL to 2.5 mg/mL, about 0.1 mg/mL to 1 mg/mL, about 0.1 mg/mL to 0.5 mg/ML, about 0.5 mg/mL to 1 mg/mL, about 0.05 mg/mL to 1 mg/mL, or about 0.05 mg/mL to 2.5 mg/mL. The concentration of a vaccine protein (e.g., antigen or antigen containing component) in a liquid vaccine formulation can be about 0.05 mg/mL, 0.1 mg/mL, 0.2 mg/mL, 0.3 mg/mL, 0.4 mg/mL, 0.5 mg/mL, 0.6 mg/mL, 0.7 mg/mL, 0.8 mg/mL, 0.9 mg/mL, 1.0 mg/mL, 1.1 mg/mL, 1.2 mg/mL, 1.3 mg/mL, 1.4 mg/mL, 1.5 mg/mL, 1.6 mg/mL, 1.7 mg/mL, 1.8 mg/mL, 1.9 mg/mL, 2.0 mg/mL, 2.5 mg/mL, 3 mg/mL, 3.5 mg/mL, 4 mg/mL, 4.5 mg/mL, 5 mg/mL, 5.5 mg/mL, 6 mg/mL, 6.5 mg/mL, 7.0 mg/mL, 8.0 mg/mL, 8.5 mg/mL, 9 mg/mL, or 10 mg/mL. The concentration of a vaccine protein (e.g. antigen or antigen-containing component) in a liquid vaccine formulation can be more than about 0.05 mg/mL, 0.1 mg/mL, 0.2 mg/mL, 0.3 mg/mL, 0.4 mg/mL, 0.5 mg/mL, 0.6 mg/mL, 0.7 mg/mL, 0.8 mg/mL, 0.9 mg/mL, 1.0 mg/mL, 1.1 mg/mL, 1.2 mg/mL, 1.3 mg/mL, 1.4 mg/mL, 1.5 mg/mL, 1.6 mg/mL, 1.7 mg/mL, 1.8 mg/mL, 1.9 mg/mL, 2.0 mg/mL, 2.5 mg/mL, 3 mg/mL, 3.5 mg/mL, 4 mg/mL, 4.5 mg/mL, 5 mg/mL, 5.5 mg/mL, 6 mg/mL, 6.5 mg/mL, 7.0 mg/mL, 8.0 mg/mL, 8.5 mg/mL, 9 mg/mL, or 10 mg/mL.

A dry vaccine powder formulation can be used to prevent and/or treat infection by one or more influenza viruses. Influenza viruses belong to the Orthomyxoviridae family of viruses, which includes five genera: Influenzavirus A, Influenzavirus B, Influenzavirus C, Isavirus, and Thogotovirus. Dhori virus is a species of the genus Thogotovirus. An influenza virus can infect humans and other species. Influenza type A viruses can infect humans, birds, pigs, horses, seals and other animals. Wild birds can be natural hosts for these viruses. Influenza type A viruses can be divided into subtypes and named on the basis of two proteins on the surface of the virus: hemagglutinin (HA) and neuraminidase (NA). For example, an "H7N2 virus" designates an influenza A subtype that has an HA7 protein and an NA2 protein. Similarly an "H5N1" virus has an HA 5 protein and an NA 1 protein. There are 16 known HA subtypes and 9 known NA subtypes. Many different combinations of HA and NA proteins are possible. Any number of the known HA subtypes (HA1, HA2, HA3, HA4, HA5, HA6, HA7, HA8, HA9, HA10, HA11, HA12, HA13, HA14, HA15, and HA16) can be combined with any number of the known NA subtypes (NA1, NA2, NA3, NA4, NA5, NA6, NA7, NA8, and NA9) to produce a vaccine to prevent or treat an infection. The HA and NA subtypes can also be used individually in a vaccine to prevent or treat infection. Different subtype vaccines can be combined at the point of use, either sequentially or simultaneously, to prevent or treat an infection. Some influenza A subtypes (e.g., H1N1, H1N2, and H3N2) are currently in general circulation among people. Other subtypes can be found in other animal species. For example, H7N7 and H3N8 viruses can cause illness in horses, and H3N8 also has recently been shown to cause illness in dogs.

Antiviral agents can be used to protect high-risk groups (e.g., individuals in a hospital unit, individuals at an institute caring for the elderly, or immuno-suppressed individuals). A potential use for an antiviral agent is to limit the spread and severity of the future pandemics whether caused by, e.g. avian H5N1 or another strains of influenza virus (e.g., H1N1). Avian influenza A viruses of the subtypes H5 and H7, including H5N1, H7N7, and H7N3 viruses, have been associated with high pathogenicity, and human infection with these viruses have ranged from mild (e.g., H7N3, H7N7) to severe and fatal disease (e.g., H7N7, H5N1). Human illness due to infection with low pathogenicity viruses has been documented, including very mild symptoms (e.g., conjunctivitis) to influenza-like illness. Examples of low pathogenicity viruses that have infected humans include H7N7, H9N2, and H7N2.

Influenza B virus can be found in humans and can also infect seals. Unlike influenza A viruses, these viruses are not classified according to subtype. Influenza B viruses can cause morbidity and morality among humans, but in general are associated with less severe epidemics, than influenza A viruses. Although influenza type B viruses can cause human epidemics, they have not caused pandemics.

Influeza type C viruses can cause mild illness in humans and do not cause epidemics or pandemics. These viruses can also infect dogs and pigs. These viruses are not classified according to subtype.

The methods and compositions described herein can be useful for the prevention and/or treatment of infection by any virus, including, for example, Abelson leukemia virus, Abelson murine leukemia virus, Abelson's virus, Acute laryngotracheobronchitis virus, Adelaide River virus, Adeno associated virus group, Adenovirus, African horse sickness virus, African swine fever virus, AIDS virus, Aleutian mink disease parvovirus, Alpharetrovirus, Alphavirus, ALV related virus, Amapari virus, Aphthovirus, Aquareovirus, Arbovirus, Arbovirus C, arbovirus group A, arbovirus group B, Arenavirus group, Argentine hemorrhagic fever virus, Argentine hemorrhagic fever virus, Arterivirus, Astrovirus, Ateline herpesvirus group, Aujezky's disease virus, Aura virus, Ausduk disease virus, Australian bat lyssavirus, Aviadenovirus, avian erythroblastosis virus, avian infectious bronchitis virus, avian leukemia virus, avian leukosis virus, avian lymphomatosis virus, avian myeloblastosis virus, avian paramyxovirus, avian pneumoencephalitis virus, avian reticuloendotheliosis virus, avian sarcoma virus, avian type C retrovirus group, Avihepadnavirus, Avipoxvirus, B virus, B19 virus, Babanki virus, baboon herpesvirus, baculovirus, Barmah Forest virus, Bebaru virus, Berrimah virus, Betaretrovirus, Birnavirus, Bittner virus, BK virus, Black Creek Canal virus, bluetongue virus, Bolivian hemorrhagic fever virus, Boma disease virus, border disease of sheep virus, borna virus, bovine alphaherpesvirus 1, bovine alphaherpesvirus 2, bovine coronavirus, bovine ephemeral fever virus, bovine immunodeficiency virus, bovine leukemia virus, bovine leukosis virus, bovine mammillitis virus, bovine papillomavirus, bovine papular stomatitis virus, bovine parvovirus, bovine syncytial virus, bovine type C oncovirus, bovine viral diarrhea virus, Buggy Creek virus, bullet shaped virus group, Bunyamwera virus supergroup, Bunyavirus, Burkitt's lymphoma virus, Bwamba Fever, CA virus, Calicivirus, California encephalitis virus, camelpox virus, canarypox virus, canid herpesvirus, canine coronavirus, canine distemper virus, canine herpesvirus, canine minute virus, canine parvovirus, Cano Delgadito virus, caprine arthritis virus, caprine encephalitis virus, Caprine Herpes Virus, Capripox virus, Cardiovirus, caviid herpesvirus 1, Cercopithecid herpesvirus 1, cercopithecine herpesvirus 1, Cercopithecine herpesvirus 2, Chandipura virus, Changuinola virus, channel catfish virus, Charleville virus, chickenpox virus, Chikungunya virus, chimpanzee herpesvirus, chub reovirus, chum salmon virus, Cocal virus, Coho salmon reovirus, coital exanthema virus, Colorado tick fever virus, Coltivirus, Columbia SK virus, common cold virus, contagious eethyma virus, contagious pustular dermatitis virus, Coronavirus, Corriparta virus, coryza virus, cowpox virus, coxsackie virus, CPV (cytoplasmic polyhedrosis virus), cricket paralysis virus, Crimean-Congo hemorrhagic fever virus, croup associated virus, Cryptovirus, Cypovirus, Cytomegalovirus, cytomegalovirus group, cytoplasmic polyhedrosis virus, deer papillomavirus, deltaretrovirus, dengue virus, Densovirus, Dependovirus, Dhori virus, diploma virus, *Drosophila* C virus, duck hepatitis B virus, duck hepatitis virus 1, duck hepatitis virus 2, duovirus, Duvenhage virus, Deformed wing virus DWV, eastern equine encephalitis virus, eastern equine encephalomyelitis virus, EB virus, Ebola virus, Ebola-like virus, echo virus, echovirus, echovirus 10, echovirus 28, echovirus 9, ectromelia virus, EEE virus, EIA virus, EIA virus, encephalitis virus, encephalomyocarditis group virus, encephalomyocarditis virus, Enterovirus, enzyme elevating virus, enzyme elevating virus (LDH), epidemic hemorrhagic fever virus, epizootic hemorrhagic disease virus, Epstein-Barr virus, equid alphaherpesvirus 1, equid alphaherpesvirus 4, equid herpesvirus 2, equine abortion virus, equine arteritis virus, equine encephalosis virus, equine infectious anemia virus, equine morbillivirus, equine rhinopneumonitis virus, equine rhinovirus, Eubenangu virus, European elk papillomavirus, European swine fever virus, Everglades virus, Eyach virus, felid herpesvirus 1, feline calicivirus, feline fibrosarcoma virus, feline herpesvirus, feline immunodeficiency virus, feline infectious peritonitis virus, feline leukemia/sarcoma virus, feline leukemia virus, feline panleukopenia virus, feline parvovirus, feline sarcoma virus, feline syncytial virus, Filovirus, Flanders virus, Flavivirus, foot and mouth disease virus, Fort Morgan virus, Four Corners hantavirus, fowl adenovirus 1, fowlpox virus, Friend virus, Gammaretrovirus, GB hepatitis virus, GB virus, German measles virus, Getah virus, gibbon ape leukemia virus, glandular fever virus, goatpox virus, golden shinner virus, Gonometa virus, goose parvovirus, granulosis virus, Gross' virus, ground squirrel hepatitis B virus, group A arbovirus, Guanarito virus, guinea pig cytomegalovirus, guinea pig type C virus, Hantaan virus, Hantavirus, hard clam reovirus, hare fibroma virus, HCMV (human cytomegalovirus), hemadsorption virus 2, hemagglutinating virus of Japan, hemorrhagic fever virus, hendra virus, Henipaviruses, Hepadnavirus, hepatitis A virus, hepatitis B virus group, hepatitis C virus, hepatitis D virus, hepatitis delta virus, hepatitis E virus, hepatitis F virus, hepatitis G virus, hepatitis nonA nonB virus, hepatitis virus, hepatitis virus (nonhuman), hepatoencephalomyelitis reovirus 3, Hepatovirus, heron hepatitis B virus, herpes B virus, herpes simplex virus, herpes simplex virus 1, herpes simplex virus 2, herpesvirus, herpesvirus 7, Herpesvirus ateles, Herpesvirus hominis, Herpesvirus infection, Herpesvirus saimiri, Herpesvirus suis, Herpesvirus varicellae, Highlands J virus, Hirame rhabdovirus, hog cholera virus, human adenovirus 2, human alphaherpesvirus 1, human alphaherpesvirus 2, human alphaherpesvirus 3, human B lymphotropic virus, human betaherpesvirus 5, human coronavirus, human cytomegalovirus group, human foamy virus, human gammaherpesvirus 4, human gammaherpesvirus 6, human hepatitis A virus, human herpesvirus 1 group, human herpesvirus 2 group, human herpesvirus 3 group, human herpesvirus 4 group, human herpesvirus 6, human herpesvirus 8, human immunodeficiency virus, human immunodeficiency virus 1, human immunodeficiency virus 2, human papillomavirus, human T cell leukemia virus, human T cell leukemia virus I, human T cell leukemia virus II, human T cell leukemia virus III, human T cell lymphoma virus I, human T cell lymphoma virus II, human T cell lymphotropic virus type 1, human T cell lymphotropic virus type 2, human T lymphotropic virus I, human T lymphotropic virus II, human T lymphotropic virus III, Ichnovirus, infantile gastroenteritis virus, infectious bovine rhinotracheitis virus, infectious haematopoietic necrosis virus, infectious pancreatic necrosis virus, influenza virus A, influenza virus B, influenza virus C, influenza virus D, influenza virus pr8, insect iridescent virus, insect virus, iridovirus, Japanese B virus, Japanese encephalitis virus, JC virus, Junin virus, Kaposi's sarcoma-associated herpesvirus, Kemerovo virus, Kilham's rat virus, Klamath virus, Kolongo virus, Korean hemorrhagic fever virus, kumba virus, Kysanur forest disease virus, Kyzylagach virus, La Crosse virus, lactic dehydrogenase elevating virus, lactic dehydrogenase virus, Lagos bat virus, Langur virus, lapine parvovirus, Lassa fever virus, Lassa virus, latent rat virus, LCM virus, Leaky virus, Lentivirus, Leporipoxvirus, leukemia virus, leukovirus, lumpy skin disease virus, lymphadenopathy associated virus, Lymphocryptovirus, lymphocytic choriomeningitis virus, lymphoproliferative virus group, Machupo virus, mad itch virus, mammalian type B oncovirus group, mammalian type B retroviruses, mammalian type C retrovirus group, mammalian type D retroviruses, mammary tumor virus, Mapuera virus, Marburg virus, Marburg-like virus, Mason Pfizer monkey virus, Mastadenovirus, Mayaro virus, ME virus, measles virus, Menangle virus, Mengo virus, Mengovirus, Middelburg virus, milkers nodule virus, mink enteritis virus, minute virus of mice, MLV related virus, MM virus, Mokola virus, Molluscipoxvirus, Molluscum contagiosum virus, monkey B virus, monkeypox virus, Mononegavirales, Morbillivirus, Mount Elgon bat virus, mouse cytomegalovirus, mouse encephalomyelitis virus, mouse hepatitis virus, mouse K virus, mouse leukemia virus, mouse mammary tumor virus, mouse minute virus, mouse pneumonia virus, mouse poliomyelitis virus, mouse polyomavirus, mouse sarcoma virus, mousepox virus, Mozambique virus, Mucambo virus, mucosal disease virus, mumps virus, murid betaherpesvirus 1, murid cytomegalovirus 2, murine cytomegalovirus group, murine encephalomyelitis virus, murine hepatitis virus, murine leukemia virus, murine nodule inducing virus, murine polyomavirus, murine sarcoma virus, Muromegalovirus, Murray Valley encephalitis virus, myxoma virus, Myxovirus, Myxovirus multiforme, Myxovirus parotitidis, Nairobi sheep disease virus, Nairovirus, Nanirnavirus, Nariva virus, Ndumo virus, Neethling virus, Nelson Bay virus, neurotropic virus, New World Arenavirus, newborn pneumonitis virus, Newcastle disease virus, Nipah virus, noncytopathogenic virus, Norwalk virus, nuclear polyhedrosis virus (NPV), nipple neck virus, O'nyong'nyong virus, Ockelbo virus, oncogenic virus, oncogenic viruslike particle, oncornavirus, Orbivirus, Orf virus, Oropouche virus, Orthohepadnavirus, Orthomyxovirus, Orthopoxvirus, Orthoreovirus, Orungo, ovine papillomavirus, ovine catarrhal fever virus, owl monkey herpesvirus, Palyam virus, Papillomavirus, Papillomavirus sylvilagi, Papovavirus, parainfluenza virus, parainfluenza virus type 1, parainfluenza virus type 2, parainfluenza virus type 3, parainfluenza virus type 4, Paramyxovirus, Parapoxvirus, paravaccinia virus, Parvovirus, Parvovirus B19, parvovirus group, Pestivirus, Phlebovirus, phocine distemper virus, Picodnavirus, Picornavirus, pig cytomegalovirus—pigeonpox virus, Piry virus, Pixuna virus, pneumonia virus of mice, Pneumovirus, poliomyelitis virus, poliovirus, Polydnavirus, polyhedral virus, polyoma virus, Polyomavirus, Polyomavirus bovis, Polyomavirus cercopi theci, Polyomavirus hominis 2, Polyomavirus maccacae 1, Polyomavirus muris 1, Polyomavirus muris 2, Polyomavirus papionis 1, Polyomavirus papionis 2, Polyomavirus sylvilagi, Pongine herpesvirus 1, porcine epidemic diarrhea virus, porcine hemagglutinating encephalomyelitis virus, porcine parvovirus, porcine transmissible gastroenteritis virus, porcine type C virus, pox virus, poxvirus, poxvirus variolae, Prospect Hill virus, Provirus, pseudocowpox virus, pseudorabies virus, psittacinepox virus, quailpox virus, rabbit fibroma virus, rabbit kidney vaculolating virus, rabbit papillomavirus, rabies virus, raccoon parvovirus, raccoonpox virus, Ranikhet virus, rat cytomegalovirus, rat parvovirus, rat virus, Rauscher's virus, recombinant vaccinia virus, recombinant virus, reovirus, reovirus 1, reovirus 2, reovirus 3, reptilian type C virus, respiratory infection virus, respiratory syncytial virus, respiratory virus, reticuloendotheliosis virus, Rhabdovirus, Rhabdovirus carpia, Rhadinovirus, Rhinovirus, Rhizidiovirus, Rift Valley fever virus, Riley's virus, rinderpest virus, RNA tumor virus, Ross River virus, Rotavirus, rougeole virus, Rous sarcoma virus, rubella virus, rubeola virus, Rubivirus, Russian autumn encephalitis virus, SA 11 simian virus, SA2 virus, Sabia virus, Sagiyama virus, Saimirine herpesvirus 1, salivary gland virus, sandfly fever virus group, Sandjimba virus, SARS virus, SDAV (sialodacryoadenitis virus), sealpox virus, Semliki Forest Virus, Seoul virus, sheeppox virus, Shope fibroma virus, Shope papilloma virus, simian foamy virus, simian hepatitis A virus, simian human immunodeficiency virus, simian immunodeficiency virus, simian parainfluenza virus, simian T cell lymphotrophic virus, simian virus, simian virus 40, Simplexvirus, Sin Nombre virus, Sindbis virus, smallpox virus, South American hemorrhagic fever viruses, sparrowpox virus, Spumavirus, squirrel fibroma virus, squirrel monkey retrovirus, SSV 1 virus group, STLV (simian T lymphotropic virus) type I, STLV (simian T lymphotropic virus) type II, STLV (simian T lymphotropic virus) type III, stomatitis papulosa virus, submaxillary virus, suid alphaherpesvirus 1, suid herpesvirus 2, Suipoxvirus, swamp fever virus, swinepox virus, Swiss mouse leukemia virus, TAC virus, Tacaribe complex virus, Tacaribe virus, Tanapox virus, Taterapox virus, Tench reovirus, Theiler's encephalomyelitis virus, Theiler's virus, Thogoto virus, Thottapalayam virus, Tick borne encephalitis virus, Tioman virus, Togavirus, Torovirus, tumor virus, Tupaia virus, turkey rhinotracheitis virus, turkeypox virus, type C retroviruses, type D oncovirus, type D retrovirus group, ulcerative disease rhabdovirus, Una virus, Uukuniemi virus group, vaccinia virus, vacuolating virus, varicella zoster virus, Varicellovirus, Varicola virus, variola major virus, variola virus, Vasin Gishu disease virus, VEE virus, Venezuelan equine encephalitis virus, Venezuelan equine encephalomyelitis virus, Venezuelan hemorrhagic fever virus, vesicular stomatitis virus, Vesiculovirus, Vilyuisk virus, viper retrovirus, viral haemorrhagic septicemia virus, Visna Maedi virus, Visna virus, volepox virus, VSV (vesicular stomatitis virus), Wallal virus, Warrego virus, wart virus, WEE virus, West Nile virus, western equine encephalitis virus, western equine encephalomyelitis virus, Whataroa virus, Winter Vomiting Virus, woodchuck hepatitis B virus, woolly monkey sarcoma virus, wound tumor virus, WRSV virus, Yaba monkey tumor virus, Yaba virus, Yatapoxvirus, yellow fever virus, and the Yug Bogdanovac virus.

B. Non-Viral Pathogen Vaccine Components

A vaccine described herein can comprise bacterial, fungal, or protist cells or components thereof. For example, a vaccine to a bacterial pathogen can comprise a killed bacterium or a purified antigenic determinant thereof. Attenuated bacteria can also be used as an antigen. In some instances, a vaccine to a toxin produced by a cellular pathogen (e.g., cholera toxin) can be produced by combining the inactivated toxin (toxoid) with one or more of the vaccine components described herein. An antigenic peptide from a target pathogen can be purified from a source pathogen and/or produced recombinantly prior to combining with the one or more of the components of the vaccine. Conjugate antigens can also be used. In a conjugate antigen, the poorly antigenic polysaccharide outer coat of a bacterial pathogen is attached to toxic protein that can stimulate an immune response. Typically, vaccines to non-viral pathogens will be designed to produce immune responses (e.g., sIgA production) to pathogens which affect mucosal surfaces, or gain access to the body via mucosal surfaces. Non-limiting examples of such pathogens include *Cryptococcus neoformans, Shigella* spp., *Salmonella typhi, Sa. paratyphi,* enterotoxigenic *Escherischia coli, Yersinia pestis, Mycobacterium tubercolosis, Ureaplasma urealyticum, Cryptosporidium* spp., *Clostridium tetani, Corynebacterium diphtheriae, Neisseria meningitidis, Bordetella pertussis, Streptococcus pneumoniae, Bacillus anthracis, Leptospira interrogans, Leptospira kirschneri, Leptospira noguchii, Leptospira alexanderi, Leptospira weilii, Leptospira borgpetersenii, Leptospira santarosai, Leptospira kmetyi, Borrelia burgdorferi, Brucella abortus, Brucella canis, Brucella melitensis, Brucella suis, Campylobacter jejuni, Chlamydia pneumoniae, Chlamydia trachomatis, Chlamydophila psittaci, Clostridium botulinum, Clostridium difficile, Clostridium perfringens, Enterococcus faecalis, Enterococcus faecium, Francisella tularensis, Haemophilus influenzae, Helicobacter pylori, Legionella pneumophila, Leptospira interrogans, Listeria monocytogenes, Mycobacterium leprae, Mycobacterium ulcerans, Mycoplasma pneumoniae, Neisseria gonorrhoeae, Neisseria meningitidis, Pseudomonas aeruginosa, Rickettsia rickettsii, Salmonella typhi, Salmonella typhimurium, Shigella sonnei, Staphylococcus aureus, Staphylococcus epidermidis, Staphylococcus saprophyticus, Streptococcus agalactiae, Streptococcus pneumoniae, Streptococcus pyogenes, Treponema pallidum, Vibrio cholerae, Candida albicans, Aspergillus fumigatus, Aspergillus flavus, Cryptococcus gattii, Histoplasma capsulatum, Pneumocystis jirovecii, Stachybotrys chartarum, Plasmodium falciparum,* etc.

C. Preparation of Antigenic Components

In order to preserve the antigenic function of the proteins or other cellular components of the pathogen, the present disclosure provides methods for preparing a vaccine which can preserve some or all of a three-dimensional configuration of the antigenic component (e.g., virus, protein). Thus, the methods provided herein can allow for the production of vaccines in which the antigenic determinants on the pathogen or component thereof are preserved in an intact state. For example, retaining three-dimensional structure of a protein in a vaccine can allow for retention of "conformational" epitopes to which an immune response can be triggered. "Conformational" epitopes are those which rely upon protein folding and generally are not comprised entirely of amino acids in linear form (e.g., a digested or linearized protein). Furthermore, the methods provided herein to produce vaccines can result in retention of antigenic potency (i.e., the ability to induce an immune response), such that the level of immune response in a reaction to a given amount of vaccine is at least about 100%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, 60%, 59%, 58%, 57%, 56%, 55%, 54%, 53%, 52%, 51%, or 50% as compared to exposure to the pathogen or other naturally-occurring antigenic source. Additionally, the methods provided herein can allow for the production of a vaccine in which a particular antigen retains high levels of antigenic capability (e.g., at least about 100%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, 60%, 59%, 58%, 57%, 56%, 55%, 54%, 53%, 52%, 51%, or 50%) of the total antigenic protein subjected to the quick freezing methods described herein.

One embodiment of this methodology is shown in FIG. 2. In this example, the antigen (shown as an open circle) is combined with a stabilizer (trehalose) and a buffer (phosphate buffer). The components are mixed and freeze-dried (e.g., by immersion in liquid nitrogen). The dried vaccine component produced comprises fine particles in which the antigen or antigens are still capable of eliciting an immune response and is stable at room temperature. The vaccine component can then be combined with a carrier suitable for nasal administration (e.g., microcrystalline cellulose). Non-limiting examples of components of vaccines disclosed herein are provided below.

Components of a liquid formulation can be chosen to perform certain functions. For example, one component can be utilized to provide stability to the antigen for which the vaccine is being developed. Primarily, such components can prevent antigenic degradation during the subsequent freezing process. These components can comprise any stabilizing molecule or compound, for example sugars, amino acids and/or polymers. One or more such antigenic stabilizing agents can be used in a formulation. Typically, an antigenic stabilizing agent will be wholly or partially water soluble. Preferred antigenic stabilizers will not produce hard cakes in the processes described herein. Exemplary sugars which can be utilized to produce a liquid vaccine formulations include, but are not limited to trehalose, mannitol, sucrose, lactose, inulin, sorbose, melezitose, raffinose, mannitol, xylitol, erythritol, threitol, stachyose, sorbitol, glycerol, fructose, mannose, maltose, arabinose, xylose, ribose, rhamnose, galactose, glucose, L-gluconate, and/or the like. Exemplary amino acids which can be utilized, include, but are not limited to isoleucine, valine, leucine, arginine, asparagine, glutamine, glycine, histidine, glutamate and lysine. An exemplary polymer is polyethylene glycol (PEG), but other polymers that can be utilized can include dextran, human serum albumin (HSA), nonhydrolyzed gelatin, methylcellulose, xanthan gum, carrageenan, collagen, chondroitin sulfate, a sialated polysaccharide, actin, myosin, microtubules, dynein, kinetin, polyvinyl pyrrolidone, hydrolyzed gelatin, and/or the like. A surfactant can be, e.g., a polyethylene glycol, sorbitan monolaurate (Tween 20), a polyoxyethylenesorbitan monooleate (Tween 80), a block copolymer of polyethylene and polypropylene glycol (Pluronic), and/or the like.

Although such antigenic stabilizers have been utilized in vaccine preparations, the use of one or more of these stabilizers in the present methods can result in a frozen vaccine formulation that does not form a hard cake upon drying. For example, the use of trehalose is known to provide protection to proteins when frozen, but leads to caking if the substance is not spray frozen (see, e.g., Chefson et al. J. Biotechnol. 2007 Jul. 15; 130(4):436-40). However, one embodiment provided herein is the combination of trehalose with a proteinaceous antigen, a phosphate buffer and a quick freeze method (e.g., exposure to liquid nitrogen). Such methods can lead to the production of fine powders in which the protein retains activity (e.g., antigenic capability) without forming a hard cake. This is an advance as the grinding of hard cakes is an extra step in the vaccine preparation process and can result in low recovery rate and degradation of the antigenic protein in the hard cake, through heat and/or mechanical forces.

The ratio of antigen to stabilizer can be, for example, about 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:38, 1:39, 1:40, 1:41, 1:42, 1:43, 1:44, 1:45, 1:46, 1:47, 1:48, 1:49, 1:50, 1:51, 1:52, 1:53, 1:54, 1:55, 1:56, 1:57, 1:58, 1:59, 1:60, 1:61, 1:62, 1:63, 1:64, 1:65, 1:66, 1:67, 1:68, 1:69, 1:70, 1:71, 1:72, 1:73, 1:74, 1:75, 1:76, 1:77, 1:78, 1:79, 1:80, 1:81, 1:82, 1:83, 1:84, 1:85, 1:86, 1:87, 1:88, 1:89, 1:90, 1:91, 1:92, 1:93, 1:94, 1:95, 1:96, 1:97, 1:98, 1:99, or 1:100. The ratio of antigen to stabilizer can be, for example, about 1:110, 1:120, 1:130, 1:140, 1:150, 1:160, 1:170, 1:180, 1:190, 1:200, 1:210, 1:220, 1:230, 1:240, 1:250, 1:260, 1:270, 1:280, 1:290, 1:300, 1:310, 1:320, 1:330, 1:340, 1:350, 1:360, 1:370, 1:380, 1:390, 1:400, 1:410, 1:420, 1:430, 1:440, 1:450, 1:460, 1:470, 1:480, 1:490, 1:500, 1:510, 1:520, 1:530, 1:540, 1:550, 1:560, 1:570, 1:580, 1:590, 1:600, 1:610, 1:620, 1:630, 1:640, 1:650, 1:660, 1:670, 1:680, 1:690, 1:700, 1:710, 1:720, 1:730, 1:740, 1:750, 1:760, 1:770, 1:780, 1:790, 1:800, 1:810, 1:820, 1:830, 1:840, 1:850, 1:860, 1:870, 1:880, 1:890, 1:900, 1:910, 1:920, 1:930, 1:940, 1:950, 1:960, 1:970, 1:980, 1:990, or 1:1000. A vaccine liquid formulation to be used in the freeze-drying step can comprise one or more pH buffers (FIGS. 2 and 3). The pH buffer can be, e.g., potassium phosphate, sodium phosphate, disodium hydrogenphosphate, potassium dihydrogenphosphate, sodium hydroxide, sodium acetate, histidine, HEPES, ACES, ADA, ADA, disodium salt, ADA monosodium salt, AMPSO, 2-aminoethanol, 2-amino-2-methyl-1,3-propanediol, 2-amino-2-methyl-1-propanol, 3-amino-1-propanesulfonic acid sodium salt, BES, bicine, Bis-Tris, Bis-Tris HCl, Bis-Tris propane, CAPS, CAPSO, CHES, DIPSO, DIPSO sodium salt, glycinamide HCl, glycine, HEPPS, HEPPSO, MES, MOPS, MOPSO, PIPES, TAPS, TAPSO, TES, tricine, triethanolamine, imidazole, sodium citrate, sodium succinate, ammonium bicarbonate, and/or a carbonate. A buffer can be phosphate buffered saline. The pH can be maintained at between about pH 3 to about pH 8, about pH 4 to 8, about pH 5 to 8, about pH 6 to 8, or about pH 6.0, 61, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, or 8.0. A liquid formulation can comprise, consist essentially of, or consist of one or more antigens and one or more buffers. A liquid formulation can comprise, consist essentially of, or consist of one or more antigens, one or more stabilizers, and one or more buffers.

A liquid formulation used to generate a powder formulation by the methods described herein can contain one or more other drugs, bulking agents, and/or sustained release polymers. Other drugs useful in the compositions of the invention, can include, e.g., aids to penetration, decongestants, bronchiole relaxers, expectorants, analgesics, and the like. Bulking agents can include, e.g., lactose, mannitol, and/or hydroxyethyl starch (HES). Sustained release semipermeable polymer matrix of the compositions can include, e.g., polylactides, copolymers of L-glutamic acid and gamma-ethyl-L-glutamate, poly(2-hydroxyethyl methacrylate, or liposomes.

A vaccine described herein can be made without including an adjuvant. Thus, the final vaccine can be produced using only the pathogen/antigen, a stabilizer, and a buffer which is then freeze-dried. Following freeze-drying, the vaccine can be combined with a carrier without the need to add an adjuvant prior to producing the final vaccine product. Alternately, the formulation can comprise adjuvant, a substance added to a vaccine to improve the immune response of the vaccine. An adjuvant can be added prior to, or after, freeze drying. Examples of adjuvant include mineral salts, e.g., aluminum hydroxide and aluminum or calcium phosphate gels, oil emulsions and surfactant based formulations, e.g., MF59 (microfluidised detergent stabilized oil-in-water emulsion), QS21 (purified saponin), AS02 ([SBAS2] (oil-in-water+MPL+WS-21)), Montanide ISA-51 and ISA-720 (stabilised water-in-oil emulsion); particulate adjuvants, (e.g., virsomes (unilamellar liposomal vehicles incorporating influenza hemagglutinin), AS04 ([SBAS4] Al salt with MPL), ISCOMS (structured complex of saponins and lipids), polylactide co-glycolide (PLG); microbial derivatives (natural and synthetic), e.g., monophosphoryl lipid A (MPL), Detox (MPL+*M. Phlei* cell wall skeleton), AGP [RC-529] (synthetic acylated monosaccharide), DC_Chol (lipoidal immunostimulators able to self organise into liposomes), OM-174 (lipid A derivative), CpG motifs (synthetic oligonucleotides containing immunostimulatory CpG motifs), modified LT and CT (genetically modified bacterial toxins to provide non-toxic adjuvant effects); endogenous human immunomodulators, e.g., hGM-CSF or hIL-12 (cytokines that can be administered either as protein or plasmid encoded), Immudaptin (C3d tandem array); inert vehicles, such as gold particles; and squalene. The liquid formulation and the final dry vaccine powder formulation can have no adjuvant.

III. Freeze Drying

A liquid formulation can be converted to a powder by freeze drying. Freeze drying is a process by which material is frozen and subsequently dried by removal of water by sublimation. Quick freezing can be accomplished, e.g., by immediate immersion of spray droplets (spray-freeze drying) in liquid nitrogen or a stream of cold gas. Quick freezing can also be accomplished by a process that does not comprise a spray-freezing step. Quick freezing can be accomplished by contacting a liquid vaccine formulation with liquid nitrogen (−196 degrees C.). Quick freezing can be accomplished by contacting a liquid vaccine formulation with liquid nitrogen combined with another chemical, e.g., hexane/liquid nitrogen (−94 degrees C.), methanol/liquid nitrogen (−98 degrees C.), and pentane/liquid nitrogen (−131 degrees C.) (Gordon A J and Ford R A "The Chemist's Companion. Wiley. New York 1972). Quick freezing can be accomplished by contacting a liquid vaccine formulation with a dry ice/organic solvent (e.g., ethanol, methanol, ethylene glycol, carbon tetrachloride, acetonitrile, isopropyl alcohol, or acetone) bath, e.g., carbon tetrachloride/dry ice (−23 degrees C.), acetonitrile/dry ice (−42 degrees C.), or acetone or isopropyl alcohol/dry ice bath (−78 degrees C.). (Gordon, supra). Quick freezing can be accomplished by immersing a liquid vaccine formulation in a slurry of ice and inorganic salt (e.g., NaCl or CaCl$_2$), which can reach −40 degrees C. The temperature at which a liquid vaccine formulation can be frozen can be less than about 0 degrees C., −5 degrees C., −10 degrees C., −15 degrees C., −20 degrees C., −25 degrees C., −30 degrees C., −35 degrees C., −40 degrees C., −45 degrees C., −50 degrees C., −55 degrees C., −60 degrees C., −65 degrees C., −70 degrees C., −75 degrees C., −80 degrees C., −85 degrees C., −90 degrees C., −95 degrees C., −100 degrees C., −105 degrees C., −110 degrees C., −115 degrees C., −120 degrees C., −125 degrees C., −130 degrees C., −135 degrees C., −140 degrees C., −145 degrees C., −150 degrees C., −155 degrees C., −160 degrees C., −165 degrees C., −170 degrees C., −175 degrees C., −180 degrees C., −185 degrees C., −90 degrees C., −195 degrees C., −200 degrees C., −205 degrees C., or −210 degrees C. The temperature at which a liquid vaccine formulation can be frozen can be about 0 degrees C. to −210 degrees C., 50 degrees C. to about −210 degrees C., −100 degrees C. to about −210 degrees C., or −150 degrees C. to about −200 degrees C. The temperature at which a liquid vaccine formulation can be frozen can be about 0 degrees C., −5 degrees C., −10 degrees C., −15 degrees C., −20 degrees C., −25 degrees C., −30 degrees C., −35 degrees C., −40 degrees C., −45 degrees C., −50 degrees C., −55 degrees C., −60 degrees C., −65 degrees C., −70 degrees C., −75 degrees C., −80 degrees C., −85 degrees C., −90 degrees C., −95 degrees C., −100 degrees C., −105 degrees C., −110 degrees C., −115 degrees C., −120 degrees C., −125 degrees C., −130 degrees C., −135 degrees C., −140 degrees C., −145 degrees C., −150 degrees C., −155 degrees C., −160 degrees C., −165 degrees C., −170 degrees C., −175 degrees C., −180 degrees C., −185 degrees C., −190 degrees C., −195 degrees C., −200 degrees C., −205 degrees C., or −210 degrees C. The method of freezing can prevent loss of the three-dimensional shape of an antigen in the liquid vaccine formulation.

Some antigen-containing solutions disclosed herein can contain carbohydrates. For example an antigen-containing solution can contain a sugar, including, but not limited to trehalose, mannitol, sucrose, lactose or inulin. Such sugars are utilized for various purposes, for example to protect proteinaceous components of a solution from losing or decreasing antigenic capability upon freezing. For example, the addition of trehalose to a solution can prevent loss of antigenicity of proteins, such as hemagglutinin (HA) of influenza, in liquid formulations containing proteins (e.g., liquid vaccine liquid formulations). However, the addition of trehalose and other sugars can result in the formation of a hard cake in vaccine preparations, unless spray freezing is utilized. The novel methods disclosed herein allow for the use of such sugars in a quick freezing method which does not require spray freezing, and does not result in the formation of a hard cake. This is an advance over prior approaches which require milling of hard cakes, as such treatments can result in the loss of antigenicity of component biological molecules. The combinations of buffers and sugars disclosed herein in the antigen-containing solutions allows for such results. Quick freezing of a sugar-containing solution disclosed herein can result in the generation of a powder.

A liquid vaccine formulation can be exposed to a cold liquid, e.g., liquid nitrogen, for about 30 seconds to 5 min, 1 min to 60 min, 1 min to 50 min, 1 to 40 min, 1 to 30 min, 1 to 20 min, 1 to 10 min, or 1 to 5 min. A liquid vaccine formulation can be exposed to the cold liquid, e.g., liquid nitrogen, for about 30 seconds, 1 min, 2 min, 3 min, 4 min, 5 min, 6 min, 7 min, 8 min, 9 min, 10 min, 11 min, 12 min, 13 min, 14 min, 15 min, 16 min, 17 min, 18 min, 19 min, 20 min, 25 min, 30 min, 35 min, 40 min, 45 min, 50 min, 55 min, or 60 min. A liquid vaccine formulation can be exposed to the cold liquid, e.g., liquid nitrogen for more than about 30 seconds, 1 min, 2 min, 3 min, 4 min, 5 min, 6 min, 7 min, 8 min, 9 min, 10 min, 11 min, 12 min, 13 min, 14 min, 15 min, 16 min, 17 min, 18 min, 19 min, 20 min, 25 min, 30 min, 35 min, 40 min, 45 min, 50 min, 55 min, or 60 min. A liquid vaccine formulation can be exposed to the cold liquid by putting the liquid vaccine formulation in a container and immersing the containing in the cold liquid (e.g., liquid nitrogen). A liquid vaccine formulation can be exposed to the cold liquid by directly introducing a liquid vaccine formulation into the cold liquid (e.g., liquid nitrogen). A liquid vaccine formulation can be exposed to the cold liquid by pouring the cold liquid (e.g., liquid nitrogen) over the liquid vaccine formulation.

Drying

After quick freezing, e.g., in liquid nitrogen, the frozen formulation can be freeze dried in a freeze-dryer. Freeze drying can occur in one or more steps (e.g., different temperatures at the same pressure). The freeze drying can occur at, for example, at about −210 degrees C., −205 degrees C., −200 degrees C., −195 degrees C., −190 degrees C., −185 degrees C., −180 degrees C., −175 degrees C., −170 degrees C., −165 degrees C., −160 degrees C., −155 degrees C., −150 degrees C., −145 degrees C., −140 degrees C., −135 degrees C., −130 degrees C., −125 degrees C., −120 degrees C., −115 degrees C., −110 degrees C., −105 degrees C., −100 degrees C., −95 degrees C., −90 degrees C., −85 degrees C., −80 degrees C., −75 degrees C., −70 degrees C., −65 degrees C., −60 degrees C., −55 degrees C., −50 degrees C., −45 degrees C., −40 degrees C., −35 degrees C., −30 degrees C., −25 degrees C., −20 degrees C., −15 degrees C., −10 degrees C., −5 degrees C., 0 degrees C., 5 degrees C., 10 degrees C., 15 degrees C., 20 degrees C., 25 degrees C., or 30 degrees C. Freeze drying can occur at, for example, at more than about −210 degrees C., −205 degrees C., −200 degrees C., −195 degrees C., −190 degrees C., −185 degrees C., −180 degrees C., −175 degrees C., −170 degrees C., −165 degrees C., −160 degrees C., −155 degrees C., −150 degrees C., −145 degrees C., −140 degrees C., −135 degrees C., −130 degrees C., −125 degrees C., −120 degrees C., −115 degrees C., −110 degrees C., −105 degrees C., −100 degrees C., −95 degrees C., −90 degrees C., −85 degrees C., −80 degrees C., −75 degrees C., −70 degrees C., −65 degrees C., −60 degrees C., −55 degrees C., −50 degrees C., −45 degrees C., −40 degrees C., −35 degrees C., −30 degrees C., −25 degrees C., −20 degrees C., −15 degrees C., −10 degrees C., −5 degrees C., 0 degrees C., 5 degrees C., 10 degrees C., 15 degrees C., 20 degrees C., 25 degrees C., or 30 degrees C. Freeze drying can occur at, e.g., at about −80 degrees C. to 30 degrees C., about −50 degrees C. to 25 degrees C., or about −40 degrees C. to 20 degrees C. Freeze-drying can occur at one temperature, two different temperatures, three different temperatures, four different temperatures, five different temperatures, six different temperatures, seven different temperatures, eight different temperatures, nine different temperatures, or ten different temperatures.

The freeze-drying can occur at one or more different pressures. The pressure can be, for example, about 10 mtorr to 300 mtorr, about 25 mtorr to 300 mtorr, about 50 mtorr to 250 mtorr, or about 50 mtorr to 200 mtorr. The freeze-drying can occur at about 10 mtorr, 20 mtorr, 30 mtorr, 40 mtorr, 50 mtorr, 60 mtorr, 70 mtorr, 80 mtorr, 90 mtorr, 100, mtorr, 110 mtorr, 120 mtorr, 130 mtorr, 140 mtorr, 150 mtorr, 160 mtorr, 170 mtorr, 180 mtorr, 190 mtorr, 200 mtorr, 210 mtorr, 220 mtorr, 230 mtorr, 240 mtorr, 250 mtorr, 260 mtorr, 270 mtorr, 280 mtorr, 290 mtorr, or 300 mtorr. Freeze-drying can occur at more than about 10 mtorr, 20 mtorr, 30 mtorr, 40 mtorr, 50 mtorr, 60 mtorr, 70 mtorr, 80 mtorr, 90 mtorr, 100, mtorr, 110 mtorr, 120 mtorr, 130 mtorr, 140 mtorr, 150 mtorr, 160 mtorr, 170 mtorr, 180 mtorr, 190 mtorr, 200 mtorr, 210 mtorr, 220 mtorr, 230 mtorr, 240 mtorr, 250 mtorr, 260 mtorr, 270 mtorr, 280 mtorr, 290 mtorr, or 300 mtorr.

The duration of each freeze-drying step can be from about 1 hr to 48 hr, about 1 hr to 36 hr, about 1 hr to 24 hr, about 4 hr to 24 hr, about 6 hr to 24 hr, or about 8 hr to 24 hr. The duration of each freeze-drying step can be about 1 hr, 2 hr, 3 hr, 4 hr, 5 hr, 6 hr, 7 hr, 8 hr, 9 hr, 10 hr, 11 hr, 12 hr, 13 hr, 14 hr, 15 hr, 16 hr, 17 hr, 18 hr, 19 hr, 20 hr, 21 hr, 22 hr, 23 hr, 24 hr, 25 hr, 26 hr, 27 hr, 28 hr, 29 hr, 30 hr, 31 hr, 32 hr, 33 hr, 34 hr, 35 hr, 36 hr, 37 hr, 38 hr, 39 hr, 40 hr, 41 hr, 42 hr, 43 hr, 44 hr, 45 hr, 46 hr, 47 hr, or 48 hr. The duration of each freeze-drying step can be more than about 1 hr, 2 hr, 3 hr, 4 hr, 5 hr, 6 hr, 7 hr, 8 hr, 9 hr, 10 hr, 11 hr, 12 hr, 13 hr, 14 hr, 15 hr, 16 hr, 17 hr, 18 hr, 19 hr, 20 hr, 21 hr, 22 hr, 23 hr, 24 hr, 25 hr, 26 hr, 27 hr, 28 hr, 29 hr, 30 hr, 31 hr, 32 hr, 33 hr, 34 hr, 35 hr, 36 hr, 37 hr, 38 hr, 39 hr, 40 hr, 41 hr, 42 hr, 43 hr, 44 hr, 45 hr, 46 hr, 47 hr, or 48 hr.

One or more drying steps can be utilized in the methods disclosed herein. Primary drying of a frozen sample can be performed by any relevant methodology, e.g., by lyophilization. Secondary drying can be performed by, e.g., continued freeze drying at a higher temperature in a vacuum chamber, contact exposure to temperature controlled surfaces, or by suspension of particles in a vortex or fluidized bed of temperature/humidity controlled gas. A dried powder particle product can be recovered, e.g., from process containers, or by sizing and settling of particles from process gas streams.

Other drying processes include, for example, air drying, desiccation under nitrogen purge (including grinding and sieving), freeze-drying (including milling and sieving), and supercritical fluid drying (SCF). The drying process can preserve the three-dimensional structure of an antigen. For example, the process can preserve the structure of an influenza HA antigen, providing a high HA potency.

After freeze drying, the powder can be stored (preserved) at a temperature of about 4 to 25 degrees C. The relative humidity of the preservation condition can be about 0% to 70%, about 0% to 60%, about 0% to 50%, about 0% to 40%, about 0% to 30%, about 0% to 20%, about 0% to 10%, or about 0% to 5%. The relative humidity of the preservation can be less than about 80%, 75%, 70%, 65%, 60%, 55%, 50%, 45%, 40%, 35%, 30%, 25%, 24%, 23%, 22%, 21%, 60%, 19%, 18%, 17%, 16%, 15%, 14%, 13%, 12%, 11%, 10%, 9%, 8%, 7%, 6%, 5%, 4%, 3%, 2%, or 1%.

The water content of the powder after freeze drying can be about 12%, 11%, 10%, 9%, 8%, 7%, 6%, 5%, 4%, 3%, 2%, 1%, 0.5%, or 0.1%. The water content of the powder after freeze drying can be less than 12%, 11%, 10%, 9%, 8%, 7%, 6%, 5%, 4%, 3%, 2%, 1%, 0.5%, 0.1%, or 0.01%.

Average particle diameter size of the powder generated after freeze drying can be about 5 to 100 micro m, about 5 to 60 micro m, or about 5 to 30 micro m. Average particle diameter size of the powder generated after freeze drying can be less than about 10, 15, 20, 25, 30, 35, 40, 45, 50, 55, 60, 65, 70, 75, 80, 85, 90, or 95 micro m.

IV. Carriers

A powder produced by the freeze drying methods described herein can be blended with one or more additional components to generate a dry vaccine powder formulation. Such components include pharmaceutically acceptable carriers, for example, carriers appropriate for mucosal administration. Carriers suitable for mucosal administration can be physiologically acceptable substances such as microcrystalline cellulose. Microcrystalline cellulose can be a specific microcrystalline cellulose that has a larger specific surface area. Although any microcrystalline cellulose can be utilized, in some embodiments, the microcrystalline cellulose used to produce the vaccines of the present application can be Ceolus (registered trademark) PH-F20JP or Avicel (registered trademark) PH-105.

One way of defining powdered particles of a carrier, or the complete vaccine is based on average particle size. The average particle size of the microcrystalline cellulose and/or vaccine particles can be measured by any means known in the art, for example, sifting, sieving or laser diffraction. The average particle size of the carrier (e.g., microcrystalline cellulose) and/or vaccine can be, e.g., about 10 micro m, 11 micro m, 12 micro m, 13 micro m, 14 micro m, 15 micro m, 16 micro m, 17 micro m, 18 micro m, 19 micro m, 20 micro m, 21 micro m, 22 micro m, 23 micro m, 24 micro m, 25 micro m, 26 micro m, 27 micro m, 28 micro m, 29 micro m, 30 micro m, 31 micro m, 32 micro m, 33 micro m, 34 micro m, 35 micro m, 36 micro m, 37 micro m, 38 micro m, 39 micro m, 40 micro m, 41 micro m, 42 micro m, 43 micro m, 44 micro m, 45 micro m, 46 micro m, 47 micro m, 48 micro m, 49 micro m, 50 micro m, 51 micro m, 52 micro m, 53 micro m, 54 micro m, 55 micro m, 56 micro m, 57 micro m, 58 micro m, 59 micro m, 60 micro m, 61 micro m, 62 micro m, 63 micro m, 64 micro m, 65 micro m, 66 micro m, 67 micro m, 68 micro m, 69 micro m, 70 micro m, 71 micro m, 72 micro m, 73 micro m, 74 micro m, 75 micro m, 76 micro m, 77 micro m, 78 micro m, 79 micro m, 80 micro m, 81 micro m, 82 micro m, 83 micro m, 84 micro m, 85 micro m, 86 micro m, 87 micro m, 88 micro m, 89 micro m, 90 micro m, 91 micro m, 92 micro m, 93 micro m, 94 micro m, 95 micro m, 96 micro m, 97 micro m, 98 micro m, 99 micro m, 100 micro m, 110 micro m, 120 micro m, 130 micro m, 140 micro m, 150 micro m, 160 micro m, 170 micro m, 180 micro m, 190 micro m, or 200 micro m. In some embodiments, microcrystalline cellulose used as a carrier for the vaccine compositions described herein can have an average particle size of 25 micro m, 39 micro m, or 57 micro m, measured by, for example, laser diffraction, sieving or sifting.

A carrier (e.g., microcrystalline cellulose) and/or vaccine powder can be prepared to be of useful particle size distribution. Preparations of carrier and/or vaccine can have a particle size distribution of, for example 10-200 micro m, 20-200 micro m, 30-200 micro m, 40-200 micro m, 50-200 micro m, 60-200 micro m, 70-200 micro m, 80-200 micro m, 90-200 micro m, 100-200 micro m, 110-200 micro m, 120-200 micro m, 130-200 micro m, 140-200 micro m, 150-200 micro m, 160-200 micro m, 170-200 micro m, 180-200 micro m, 190-200 micro m, or any included sub-ranges of particle size distribution. Powders described herein can have a particle size additional particle size distributions, for example 10-100 micro m, 20-100 micro m, 30-100 micro m, 40-100 micro m, 50-100 micro m, 60-100 micro m, 70-100 micro m, 80-100 micro m, 90-100 micro m, 10-50 micro m, 10-60 micro M, 20-60 micro m, 30-70 micro m, 40-80 micro m, 50-90 micro m, 60-100 micro m, 70-110 micro m, 80-120 micro m, 90-130 micro m, 100-140 micro m, 110-150 micro m, 120-160 micro m, 130-170 micro m, 140-180 micro m, 150-190 micro m, 160-200 micro m, or any included sub-range of particle sizes. The carrier and/or vaccine can have a particle size distribution of, for example, 10-50 micro m, 11-50 micro m, 12-50 micro m, 13-50 micro m, 14-50 micro m, 15-50 micro m, 16-50 micro m, 17-50 micro m, 18-50 micro m, 19-50 micro m, 20-50 micro m., 21-50 micro m, 22-50 micro m, 23-50 micro m, 24-50 micro m, 25-50 micro m, 26-50 micro m, 27-50 micro m, 28-50 micro m, 29-50 micro m, 30-50 micro m, or any included sub-range of particle sizes. In a particular embodiment, the carrier and/or vaccine can have a particle size distribution of 19-60 micro m, or a particle size distribution of 19-50 micro m.

A microcrystalline cellulose powder, or other carrier compound, useful for the preparation of vaccines described herein can be specified or unspecified, with regards to a particular physical aspect. For example microcrystalline cellulose powder can be specified to have larger particles, which can protect the lungs. A microcrystalline cellulose powder can be specified to have smaller particles, which can enhance the immune response. Physical characteristics of powders can be specified by sieving or otherwise processed to minimize the presence of particles that are, for example less than about 10 micro m, less than about 20 micro m, less than about 30 micro m, less than about 40 micro m, less than about 50 micro m, less than about 60 micro m, less than about 70 micro m, less than about 80 micro m, less than about 90 micro m, less than about 100 micro m and/or minimize particles that are greater than about 20 micro m, greater than about 30 micro m, greater than about 40 micro m, greater than about 50 micro m, greater than about 60 micro m, greater than about 70 micro m, greater than about 80 micro m, greater than about 90 micro m, greater than about 100 micro m, greater than about 110 micro m, greater than about 120 micro m, greater than about 130 micro m, greater than about 140 micro m, greater than about 150 micro m, greater than about 160 micro m, greater than about 170 micro m, greater than about 180 micro m, greater than about 190 micro m, or greater than about 200 micro m.

An additional parameter of the powder compositions that can be varied to achieve desired results (e.g., enhanced immunogenicity) described herein is the specific surface area of the powder. For example, powder compositions can be prepared such that the specific surface area of the carrier (e.g., microcrystalline cellulose) and/or vaccine is, 1.0 $m^2/g$, 1.1 $m^2/g$, 1.2 $m^2/g$, 1.3 $m^2/g$, 1.4 $m^2/g$, 1.5 $m^2/g$, 1.6 $m^2/g$, 1.7 $m^2/g$, 1.8 $m^2/g$, 1.9 $m^2/g$, 2.0 $m^2/g$, 2.1 $m^2/g$, 2.2 $m^2/g$, 2.3 $m^2/g$, 2.4 $m^2/g$, 2.5 $m^2/g$, 2.6 $m^2/g$, 2.7 $m^2/g$, 2.8 $m^2/g$, 2.9 $m^2/g$, 3.0 $m^2/g$, 3.1 $m^2/g$, 3.2 $m^2/g$, 3.3 $m^2/g$, 3.4 $m^2/g$, 3.5 $m^2/g$, 3.6 $m^2/g$, 3.7 $m^2/g$, 3.8 $m^2/g$, 3.9 $m^2/g$, 4.0 $m^2/g$, 4.1 $m^2/g$, 4.2 $m^2/g$, 4.3 $m^2/g$, 4.4 $m^2/g$, 4.5 $m^2/g$, 4.6 $m^2/g$, 4.7 $m^2/g$, 4.8 $m^2/g$, 4.9 $m^2/g$, 5.0 $m^2/g$, 5.1 $m^2/g$, 5.2 $m^2/g$, 5.3 $m^2/g$, 5.4 $m^2/g$, 5.5 $m^2/g$, 5.6 $m^2/g$, 5.7 $m^2/g$, 5.8 $m^2/g$, 5.9 $m^2/g$, 6.0 $m^2/g$, 6.1 $m^2/g$, 6.2 $m^2/g$, 6.3 $m^2/g$, 6.4 $m^2/g$, 6.5 $m^2/g$, 6.6 $m^2/g$, 6.7 $m^2/g$, 6.8 $m^2/g$, 6.9 $m^2/g$, 7.0 $m^2/g$, 7.1 $m^2/g$, 7.2 $m^2/g$, 7.3 $m^2/g$, 7.4 $m^2/g$, 7.5 $m^2/g$, 7.6 $m^2/g$, 7.7 $m^2/g$, 7.8 $m^2/g$, 7.9 $m^2/g$, 8.0 $m^2/g$, 8.1 $m^2/g$, 8.2 $m^2/g$, 8.3 $m^2/g$, 8.4 $m^2/g$, 8.5 $m^2/g$, 8.6 $m^2/g$, 8.7 $m^2/g$, 8.8 $m^2/g$, 8.9 $m^2/g$, 9.0 $m^2/g$, 9.1 $m^2/g$, 9.2 $m^2/g$, 9.3 $m^2/g$, 9.4 $m^2/g$, 9.5 $m^2/g$, 9.6 $m^2/g$, 9.7 $m^2/g$, 9.8 $m^2/g$, 9.9 $m^2/g$, 10.0 $m^2/g$, 10.1 $m^2/g$, 10.2 $m^2/g$, 10.3 $m^2/g$, 10.4 $m^2/g$, 10.5 $m^2/g$, 10.6 $m^2/g$, 10.7 $m^2/g$, 10.8 $m^2/g$, 10.9 $m^2/g$, 11.0 $m^2/g$, 11.1 $m^2/g$, 11.2 $m^2/g$, 11.3 $m^2/g$, 11.4 $m^2/g$, 11.5 $m^2/g$, 11.6 $m^2/g$, 11.7 $m^2/g$, 11.8 $m^2/g$, 11.9 $m^2/g$, 12.0 $m^2/g$, 12.1 $m^2/g$, 12.2 $m^2/g$, 12.3 $m^2/g$, 12.4 $m^2/g$, 12.5 $m^2/g$, 12.6 $m^2/g$, 12.7 $m^2/g$, 12.8 $m^2/g$, 12.9 $m^2/g$, 13.0 $m^2/g$, 13.1 $m^2/g$, 13.2 $m^2/g$, 13.3 $m^2/g$, 13.4 $m^2/g$, 13.5 $m^2/g$, 13.6 $m^2/g$, 13.7 $m^2/g$, 13.8 $m^2/g$, 13.9 $m^2/g$, 14.0 $m^2/g$, 14.1 $m^2/g$, 14.2 $m^2/g$, 14.3 $m^2/g$, 14.4 $m^2/g$, 14.5 $m^2/g$, 14.6 $m^2/g$, 14.7 $m^2/g$, 14.8 $m^2/g$, 14.9 $m^2/g$, 15.0 $m^2/g$, 15.1 $m^2/g$, 15.2 $m^2/g$, 15.3 $m^2/g$, 15.4 $m^2/g$, 15.5 $m^2/g$, 15.6 $m^2/g$, 15.7 $m^2/g$, 15.8 $m^2/g$, 15.9 $m^2/g$, 16.0 $m^2/g$, 16.1 $m^2/g$, 16.2 $m^2/g$, 16.3 $m^2/g$, 16.4 $m^2/g$, 16.5 $m^2/g$, 16.6 $m^2/g$, 16.7 $m^2/g$, 16.8 $m^2/g$, 16.9 $m^2/g$, 17.0 $m^2/g$, 17.1 $m^2/g$, 17.2 $m^2/g$, 17.3 $m^2/g$, 17.4 $m^2/g$, 17.5 $m^2/g$, 17.6 $m^2/g$, 17.7 $m^2/g$, 17.8 $m^2/g$, 17.9 $m^2/g$, 18.0 $m^2/g$, 18.1 $m^2/g$, 18.2 $m^2/g$, 18.3 $m^2/g$, 18.4 $m^2/g$, 18.5 $m^2/g$, 18.6 $m^2/g$, 18.7 $m^2/g$, 18.8 $m^2/g$, 18.9 $m^2/g$, 19.0 $m^2/g$, 19.1 $m^2/g$, 19.2 $m^2/g$, 19.3 $m^2/g$, 19.4 $m^2/g$, 19.5 $m^2/g$, 19.6 $m^2/g$, 19.7 $m^2/g$, 19.8 $m^2/g$, 19.9 $m^2/g$, or 20.0 $m^2/g$. The specific surface are of the powder can be, for example, about 21 $m^2/g$, 22 $m^2/g$, 23 $m^2/g$, 24 $m^2/g$, 25 $m^2/g$, 26 $m^2/g$, 27 $m^2/g$, 28 $m^2/g$, 29 $m^2/g$, 30 $m^2/g$, 31 $m^2/g$, 32 $m^2/g$, 33 $m^2/g$, 34 $m^2/g$, 35 $m^2/g$, 36 $m^2/g$, 37 $m^2/g$, 38 $m^2/g$, 39 $m^2/g$, 40 $m^2/g$, 41 $m^2/g$, 42 $m^2/g$, 43 $m^2/g$, 44 $m^2/g$, 45 $m^2/g$, 46 $m^2/g$, 47 $m^2/g$, 48 $m^2/g$, 49 $m^2/g$, or 50 $m^2/g$. In particular embodiments, the specific surface area of a carrier (e.g., microcrystalline cellulose) and/or vaccine powder can be equal to or less than 1.3 $m^2/g$, equal to or greater than 1.3 $m^2/g$ or can be about 2.3 $m^2/g$.

Still another parameter which can describe a powdered composition (carrier and/or vaccine) is by bulk density. In some embodiments, a powder used can have a bulk density range. A powder of the present invention can have a bulk density of, for example, 0.10-1.00 $g/cm^3$, 0.10-0.90 $g/cm^3$, 0.10-0.80 $g/cm^3$, 0.10-0.70 $g/cm^3$, 0.10-0.60 $g/cm^3$, 0.10-0.50 $g/cm^3$, 0.10-0.40 $g/cm^3$, 0.10-0.30 $g/cm^3$, 0.20-1.00 $g/cm^3$, 0.20-0.90 $g/cm^3$, 0.20-0.80 $g/cm^3$, 0.20-0.70 $g/cm^3$, 0.20-0.60 $g/cm^3$, 0.20-0.50 $g/cm^3$, 0.20-0.40 $g/cm^3$, 0.20-0.30 $g/cm^3$, 0.30-1.00 $g/cm^3$, 0.30-0.90 $g/cm^3$, 0.30-0.80 $g/cm^3$, 0.30-0.70 $g/cm^3$, 0.30-0.60 $g/cm^3$, 0.30-0.50 $g/cm^3$, 0.30-0.40 $g/cm^3$, 0.40-1.00 $g/cm^3$, 0.40-0.90 $g/cm^3$, 0.40-0.80 $g/cm^3$, 0.40-0.70 $g/cm^3$, 0.40-0.60 $g/cm^3$, 0.40-0.50 $g/cm^3$, 0.50-1.00 $g/cm^3$, 0.50-0.90 $g/cm^3$, 0.50-0.80 $g/cm^3$, 0.50-0.70 $g/cm^3$, 0.50-0.60 $g/cm^3$, 0.60-1.00 $g/cm^3$, 0.60-0.90 $g/cm^3$, 0.60-0.80 $g/cm^3$, 0.60-0.70 $g/cm^3$, 0.70-1.00 $g/cm^3$, 0.70-0.90 $g/cm^3$, 0.70-0.80 $g/cm^3$, 0.80-1.00 $g/cm^3$, 0.80-0.90 $g/cm^3$, 0.9-1.0 $g/cm3$, or any included sub range. In particular embodiments, a carrier (e.g., microcrystalline cellulose) and/or vaccine powder with a bulk density of 0.13-2.9 $g/cm^3$ or 0.26-0.48 $g/cm^3$ can be used. In other embodiments, a powder can have a particular bulk density of, for example 0.10 $g/cm^3$, 0.11 $g/cm^3$, 0.12 $g/cm^3$, 0.13 $g/cm^3$, 0.14 $g/cm^3$, 0.15 $g/cm^3$, 0.16 $g/cm^3$, 0.17 $g/cm^3$, 0.18 $g/cm^3$, 0.19 $g/cm^3$, 0.20 $g/cm^3$, 0.21 $g/cm^3$, 0.22 $g/cm^3$, 0.23 $g/cm^3$, 0.24 $g/cm^3$, 0.25 $g/cm^3$, 0.26 $g/cm^3$, 0.27 $g/cm^3$, 0.28 $g/cm^3$, 0.29 $g/cm^3$, 0.30 $g/cm^3$, 0.31 $g/cm^3$, 0.32 $g/cm^3$, 0.33 $g/cm^3$, 0.34 $g/cm^3$, 0.35 $g/cm^3$, 0.36 $g/cm^3$, 0.37 $g/cm^3$, 0.38 $g/cm^3$, 0.39 $g/cm^3$, 0.40 $g/cm^3$, 0.41 $g/cm^3$, 0.42 $g/cm^3$, 0.43 $g/cm^3$, 0.44 $g/cm^3$, 0.45 $g/cm^3$, 0.46 $g/cm^3$, 0.47 $g/cm^3$, 0.48 $g/cm^3$, 0.49 $g/cm^3$, 0.50 $g/cm^3$, 0.51 $g/cm^3$, 0.52 $g/cm^3$, 0.53 $g/cm^3$, 0.54 $g/cm^3$, 0.55 $g/cm^3$, 0.56 $g/cm^3$, 0.57 $g/cm^3$, 0.58 $g/cm^3$, 0.59 $g/cm^3$, 0.60 $g/cm^3$, 0.61 $g/cm^3$, 0.62 $g/cm^3$, 0.63 $g/cm^3$, 0.64 $g/cm^3$, 0.65 $g/cm^3$, 0.66 $g/cm^3$, 0.67 $g/cm^3$, 0.68 $g/cm^3$, 0.69 $g/cm^3$, 0.70 $g/cm^3$, 0.71 $g/cm^3$, 0.72 $g/cm^3$, 0.73 $g/cm^3$, 0.74 $g/cm^3$, 0.75 $g/cm^3$, 0.76 $g/cm^3$, 0.77 $g/cm^3$, 0.78 $g/cm^3$, 0.79 $g/cm^3$, 0.80 $g/cm^3$, 0.81 $g/cm^3$, 0.82 $g/cm^3$, 0.83 $g/cm^3$, 0.84 $g/cm^3$, 0.85 $g/cm^3$, 0.86 $g/cm^3$, 0.87 $g/cm^3$, 0.88 $g/cm^3$, 0.89 $g/cm^3$, 0.90 $g/cm^3$, 0.91 $g/cm^3$, 0.92 $g/cm^3$, 0.93 $g/cm^3$, 0.94 $g/cm^3$, 0.95 $g/cm^3$, 0.96 $g/cm^3$, 0.97 $g/cm^3$, 0.98 $g/cm^3$, 0.99 $g/cm^3$, or 1.00 $g/cm^3$. In some embodiments, a carrier (e.g., microcrystalline cellulose) and/or vaccine powder can have a bulk density of 0.23 $g/cm^3$ or 0.41 $g/cm^3$.

A carrier, such as microcrystalline cellulose, can comprise about 25% to about 98% of the mass of the dry vaccine powder formulation. In some embodiments, the carrier can comprise no more than about 98%, 95%, 90%, 85%, 80%, 75%, 70%, 65%, 60%, 55%, 50%, 45%, 40%, 35%, 30%, or 25% of a dry vaccine powder formulation.

Another carrier useful in the vaccines of the present invention can be tribasic calcium phosphate (TCP). TCP can comprise about 0.5% to about 5% of the dry vaccine powder formulation. TCP can comprise no more than about 0.5%, 0.8%, 0.9%, 1%, 1.2%, 1.4%, 1.6%, 1.8%, 2%, 2.2%, 2.4%, 2.6%, 2.8%, 3%, 4%, or 5% of the dry vaccine powder formulation.

A carrier can be added by blending, e.g., by vortexing. The duration of the blending, e.g., vortexing, can be about 30 secs to 120 min, about 30 secs to 2 min, about 30 secs to 7.5 min, about 20 secs to 15 min, about 30 secs to 30 min, about 30 secs to 45 min, about 30 secs to 60 min, about 30 secs to 75 min, about 30 secs to 90 min. about 30 secs to 120 min. The duration of the blending, e.g., vortexing, can be more than about 30 secs, 1 min, 2 min, 4 min, 8 min, 10 min, 15 min, 20 min, 30 min, 45 min, 60 min, 90 min, or 120 min. The duration of the blending, e.g., vortexing, can be about 30 secs, 1 min, 5 min, 10 min, 15 min, 30 min, 45 min, 60 min, 75 min, 90 min, or 120 min.

Upon blending the particle size of a dry vaccine formulation comprising freeze dried antigen-containing powder and a carrier can be any appropriate size for delivery of the dry powder vaccine to an anatomical site of interest. Additionally, size of the particles can be adjusted for different delivery devices. Thus, average particle diameter size of a dry powder vaccine formulation containing freeze dried antigen (e.g., influenza) and a carrier (e.g., microcrystalline cellulose) generated by the methods herein can be less than about 10 micro m, 11 micro m, 12 micro m, 13 micro m, 14 micro m, 15 micro m, 16 micro m, 17 micro m, 18 micro m, 19 micro m, 20 micro m, 21 micro m, 22 micro m, 23 micro m, 24 micro m, 25 micro m, 26 micro m, 27 micro m, 28 micro m, 29 micro m, 30 micro m, 31 micro m, 32 micro m, 33 micro m, 34 micro m, 35 micro m, 36 micro m, 37 micro m, 38 micro m, 39 micro m, 40 micro m, 41 micro m, 42 micro m, 43 micro m, 44 micro m, 45 micro m, 46 micro m, 47 micro m, 48 micro m, 49 micro m, 50 micro m, 51 micro m, 52 micro m, 53 micro m, 54 micro m, 55 micro m, 56 micro m, 57 micro m, 58 micro m, 59 micro m, 60 micro m, 61 micro m, 62 micro m, 63 micro m, 64 micro m, 65 micro m, 66 micro m, 67 micro m, 68 micro m, 69 micro m, 70 micro m, 71 micro m, 72 micro m, 73 micro m, 74 micro m, 75 micro m, 76 micro m, 77 micro m, 78 micro m, 79 micro m, 80 micro m, 81 micro m, 82 micro m, 83 micro m, 84 micro m, 85 micro m, 86 micro m, 87 micro m, 88 micro m, 89 micro m, 90 micro m, 91 micro m, 92 micro m, 93 micro m, 94 micro m, 95 micro m, 96 micro m, 97 micro m, 98 micro m, 99 micro m, 100 micro m, 110 micro m, 120 micro m, 130 micro m, 140 micro m, 150 micro m, 160 micro m, 170 micro m, 180 micro m, 190 micro m, or 200 micro m.

The dry vaccine formulation comprising freeze dried antigen-containing powder and a carrier can have a range of particle sizes, for example 10-200 micro m, 20-200 micro m, 30-200 micro m, 40-200 micro m, 50-200 micro m, 60-200 micro m, 70-200 micro m, 80-200 micro m, 90-200 micro m, 100-200 micro m, 110-200 micro m, 120-200 micro m, 130-200 micro m, 140-200 micro m, 150-200 micro m, 160-200 micro m, 170-200 micro m, 180-200 micro m, 190-200 micro m, or any included sub-ranges of particle size. The dry vaccine formulation comprising freeze dried antigen-containing powder and a carrier can have a range of particle sizes, for example 10-100 micro m, 20-100 micro m, 30-100 micro m, 40-100 micro m, 50-100 micro m, 60-100 micro m, 70-100 micro m, 80-100 micro m, 90-100 micro m, 10-50 micro m, 20-60 micro m, 30-70 micro m, 40-80 micro m, 50-90 micro m, 60-100 micro m, 70-110 micro m, 80-120 micro m, 90-130 micro m, 100-140 micro m, 110-150 micro m, 120-160 micro m, 130-170 micro m, 140-180 micro m, 150-190 micro m, 160-200 micro m, or any included sub-range of particle sizes.

Dry vaccine formulation comprising freeze dried antigen-containing powder and a carrier can be specified by sieving or otherwise processed to minimize particles that are, for example less than about 10 micro m, less than about 20 micro m, less than about 30 micro m, less than about 40 micro m, less than about 50 micro m, less than about 60 micro m, less than about 70 micro m, less than about 80 micro m, less than about 90 micro m, less than about 100 micro m. and/or minimize particles that are greater than about 20 micro m, greater than about 30 micro m, greater than about 40 micro m, greater than about 50 micro m, greater than about 60 micro m, greater than about 70 micro m, greater than about 80 micro m, greater than about 90 micro m, greater than about 100 micro m, greater than about 110 micro m, greater than about 120 micro m, greater than about 130 micro m, greater than about 140 micro m, greater than about 150 micro m, greater than about 160 micro m, greater than about 170 micro m, greater than about 180 micro m, greater than about 190 micro m, or greater than about 200 micro m.

V. Stability and Hygroscopicity

A dry vaccine powder formulation prepared as described herein can be stable at room temperature (25 degrees C. and 60% relative humidity) for at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or 36 months. The stability of the dry vaccine powder formulation can also be stable under accelerated conditions (45 degrees C. and 75% relative humidity) for extended time periods. Under accelerated conditions, a dry vaccine powder formulation can be stable for at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or 36 months. A dry vaccine powder formulation prepared as described herein can be stable at other temperatures (e.g., −20 degrees C. to 55 degrees C.) and relative humidities (0% to 100%).

Stability, as used herein, can refer to several aspects of the dry vaccine powder under storage conditions. One such aspect is vaccine potency, i.e., retention of antigenicity of the antigenic component of the vaccine. This aspect of stability, for example, of a dry influenza vaccine powder formulation comprising HA, can be determined by measuring HA antigenicity. A vaccine powder is considered stable if it retains greater the 50% antigenicity (compared to initial potency) after a particular time under particular conditions (e.g., 18 months under accelerated conditions).

Alternately, stability can refer to the ability of the dry powder to resist uptake of environmental water under storage conditions. Such uptake of water can lead to increased clumping, which, in turn can lead to undesirable properties such as decreased flowability and decreased bioavailability.

A dry vaccine powder formulation described herein can have low hygroscopicity. Hygroscopicity of a dry vaccine powder formulation can be measured over time by weighing the dry vaccine powder formulation. An increase in weight indicates acquisition of water. Hygroscopicity can be determined by the amount of water absorbed by the dry vaccine powders of the present invention when the powder is stored in an air-tight container, a non-air tight container or in an open system.

VI. Routes and Means of Administration

In some embodiments, a device can be configured to deliver a substantial fraction of a single dose of a dry vaccine powder therapeutic formulation into the nostril of a subject. In some cases, a device may be configured to deliver a substantial fraction of an amount of a dry vaccine powder therapeutic formulation residing within the device into the nostril of a subject. In some cases, a dry vaccine powder therapeutic formulation or a substantial fraction thereof may be delivered after a single engagement of the device. In some cases, a powdered therapeutic formulation or a substantial fraction thereof can be delivered after multiple engagements of the device, such as for example 1, 2, 3, 4, 5, 6, 7, 8, 9, or 10 engagements. In some cases, multiple engagements of a device may constitute a single use of a device. According to the methods, devices, and compositions described herein a substantial fraction of the dry vaccine powder therapeutic formulation delivered by the device encompasses at least 50%, 55%, 60%, 65%, 70%, 75%, 80%, 85%, 90%, 91%, 92%, 93%, 94%, 95%, 96%, 97%, 97.5%, 98%, 98.5%, 99%, 99.5%, 99.9%, 99.95%, or 100% of the amount of dry powdered medicine therapeutic such as the amount in a single dose or the amount residing in the device.

Nasal applicators appropriate for use with dry vaccine powder formulations generated by the methods of the provided invention are described in pending U.S. Application Ser. No. 61/260,367, which is herein incorporated by reference in its entirety.

VII. Effects of Dry Powder Formulation on Immunity

The methods and compositions of the provided invention can be used to stimulate a local immune response. A local immune response can be in peripheral lymphoid tissue. For example, a vaccine dry powder formulation can be administered intranasally to stimulate mucosa-associated lymphoid tissue (MALT), which can play a role in mucosal immunity. Examples of mucosa include buccal mucosa, esophageal mucosa, gastric mucosa, intestinal mucosa, nasal mucosa, olfactory mucosa, oral mucosa, bronchial mucosa, uterine mucosa, endometrium (mucosa of the uterus), and penile mucosa. In particular, nasopharynx-associated lymphoid tissue (NALT) can be targeted. NALT can play a role in the generation of T helper 1 and T helper 2 cells, and IgA-committed B cells. Intranasal immunization can lead to the induction of antigen-specific protective immunity in both the mucosal and systemic immune compartments.

The methods and compositions of the provided invention can be used to stimulate production of the principal antibody of the mucosal immune system, secretory IgA (sIgA) (FIGS. 6, 7, 9, 11, 12 and 20). sIgA is a dimer or tetramer composed of two or four monomers, a J-chain polypeptide, and a polypeptide chain called secretory component. The J-chain polypeptide can facilitate the polymerization of both serum and secretory IgA. The secretory component is a 70 kDa polypeptide produced by epithelial cells of mucous membranes and can protect sIgA by making it less susceptible to proteolytic enzymes in mucous secretions. sIgA can be produced locally by mucosal plasma cells that are descended from precursors initially stimulated in organized, mucosal lymphoid organs designed for antigen sampling. After an initial trigger, the precursor cells can pass via regional lymph nodes, lymph, and blood to disseminate widely among mucosal sites, thus leading to protection at mucosal sites other than the site of administration (e.g., nasal administration). After secretion from a local plasma cell, sIgA can bind to an epithelial cell surface receptor, and the complex can pass through the epithelial cell into the secretions where it can serve as a nonphlogistic immunologic barrier to inhibit uptake of antigens.

In addition to stimulating a mucosal (i.e., sIgA) response, the dry powder formulations disclosed herein can also stimulate an IgG response (FIGS. 6, 7, 9, 11, 12, 14, 17 and 19). Such stimulation can lead to an additional layer of protection, for example by priming the humoral response to react to a pathogen which eludes or evades the protection provided by the sIgA induced by a vaccine disclosed herein. Thus, in one embodiment, the vaccines disclosed herein can induce both mucosal and humoral antibody responses.

EXAMPLES

Example 1

Preparation and Testing of Whole Inactive H1N1 Dry Vaccine Powder Formulation

In this example, various dry powder formulations of the seasonal flu vaccine (H1N1) are generated and tested. A preferred embodiment of the invention is also tested verses traditional liquid nasal and injection formulations of the seasonal flu vaccine.

Example 1A

Preparation of Influenza Vaccine (H1N1) Powders Using Non-Quick Freezing Techniques In this experiment, various antigen stabilizers are used in a conventional freeze-drying process to generate vaccine powders, which are then examined for consistency and stability. In a 10 mL bottle, 0.4 mL of a 1.6 mg/mL solution of whole inactive influenza (H1N1, strain A/Brisbane/59/2007, The Chemo-Sero-Therapeutic Research Institute) is combined with a stabilizer (13.6 mg) in 0.4 mL of Phosphate Buffered Saline (PBS or phosphate buffer), pH 7.4, to give a final antigen to stabilizer ratio of 1:21. The mixture is slowly frozen at −40 degrees C. for over 5 hours. The frozen composition is then freeze dried in four steps: −40 degrees C., less than 140 mTorr for 24 hr; 30 degrees C., less than 130 mtorr for 24 hr; −10 degrees C., less than 100 mtorr for 4 hr; and 20 C, less than 50 mtorr for 4 hr. The resulting lyophilized powder contains 29 micro g of influenza vaccine protein per 1 mg of influenza vaccine powder. The influenza vaccine powder is combined (blended) with nasal carriers (e.g., microcrystalline cellulose) with specific surface area of greater than 1.3 square meter per gram and tribasic calcium phosphate (TCP) $(Ca_3(PO_4)_2)$. Influenza vaccine powder (49.3 mg, including 1.44 mg of influenza vaccine protein, is combined with 309.1 mg of Ceolus (registered trademark) PH-F20JP microcrystalline cellulose (mean particle size: 57 micro m; bulk density: 0.23 g/cm3; specific surface area: 2.3 m2/g), 40.0 mg of Ceolus (registered trademark) PH-301 microcrystalline cellulose (mean particle size: 39 micro m; bulk density: 0.41 $g/cm^3$), and 1.6 mg of TCP in a 10 mL glass bottle, and the components are blended using a vortex mixer for one minute. The resulting dry influenza vaccine powder formulation contains 90 micro g of influenza vaccine protein per 25 mg of dry influenza vaccine powder formulation. In one case, trehalose is used as the stabilizer to generate an influenza vaccine powder that is partially caked and stable HA potency. In another case, mannitol is used as the stabilizer to generate an influenza vaccine powder that comprises fine particles and has unstable HA potency. In yet another case, lactose is used as the stabilizer to generate an influenza vaccine powder that is a partially caked and has stable HA potency (FIG. 1). In this example, stability is defined as retaining greater than 50% HA potency after freeze drying; unstable is equal to, or less than, 50% HA potency after freeze drying; results are summarized in Table 1. Because the formulations lack both full HA potency and good flowability, such approaches require improvements to produce effective and fully deliverable intranasal vaccines.

TABLE 1

| | Influenza (H1N1) vaccine powder generated by non-quick freezing technique | | |
|---|---|---|---|
| Antigen stabilizer | Total protein of antigen/stabilizer ratio (by weight) | Powder Property | HA potency Stable, >50%; Unstable, ≤50% |
| Trehalose | 1:21 | Cake | Stable |
| Mannitol | 1:21 | Fine | Unstable |
| Lactose | 1:21 | Cake | Stable |

Example 1B

Preparation of a Nasal Influenza (H1N1) Vaccine Powder Using a Quick Freezing Process In this experiment, various stabilizers are used in a quick freezing and drying process to generate vaccine powders, which are then examined for consistency and stability. The general manufacturing process is outlined in FIGS. 2 and 3; specific details relating to the generation of a H1N1 nasal vaccine formulation are provided infra. In a 10 mL bottle, 0.4 mL of a 1.6 mg/mL solution of whole inactive influenza (H1N1, strain A/Brisbane/59/2007) is combined with a stabilizer (13.6 mg) in 0.4 mL of Phosphate Buffered Saline (PBS or phosphate buffer), pH 7.4, to give a final antigen to stabilizer ratio of 1:21. The mixture is quickly frozen in liquid nitrogen for 10 minutes and an influenza powder is generated by a four step freeze-drying process: −40 degrees C., less than 140 mtorr for 24 hr; −30 degrees C., less than 130 mtorr for 24 hr; −10 degrees C., less than 100 mtorr for 4 hr; and 20 C, less than 50 mtorr for 4 hr. The powder, which contains 29 micro g of influenza vaccine protein per 1 mg of influenza vaccine powder, is comprised of fine particles and is stable at room temperature, stability being defined as retaining greater than 50% HA potency (Table 2). The influenza vaccine powder is combined (blended) with nasal carriers (e.g., microcrystalline cellulose) with specific surface area of greater than 1.3 square meter per gram and tribasic calcium phosphate (TCP) ($Ca_3(PO_4)_2$). Influenza vaccine powder (49.3 mg, including 1.44 mg of influenza vaccine protein and 30.60 mg of trehalose), is combined with 309.1 mg of Ceolus (registered trademark) PH-F20JP microcrystalline cellulose (mean particle size: 57 micro m; bulk density: 0.23 g/cm$^3$; specific surface area: 2.3 m$^2$/g), 40.0 mg of Ceolus (registered trademark) PH-301 microcrystalline cellulose (mean particle size: 39 micro m; bulk density: 0.41 g/cm3), and 1.6 mg of TCP in a 10 mL glass bottle, and the components are blended using a vortex mixer for one minute. The resulting dry influenza vaccine powder formulation contains 90 micro g of influenza vaccine protein per 25 mg of dry influenza vaccine powder formulation. In one case, trehalose was used as the antigen stabilizer resulting in a formulation with stable HA potency and fine particle size. In another case, lactose was used as the antigen stabilizer, which also produced a stable formulation consisting of fine particle size. Mannitol was not tested as an antigen stabilizer for H1N1 vaccine powders.

TABLE 2

Influenza (H1N1) vaccine powder generated by quick freezing technique

| Antigen stabilizer | Total protein of antigen/stabilizer ratio (by weight) | Powder Property | HA potency Stable, >50%; Unstable, ≤50% |
| --- | --- | --- | --- |
| Trehalose | 1:21 | Fine | Stable |
| Mannitol | not tested | not tested | not tested |
| Lactose | 1:21 | Fine | Stable |

Example 1C

Study Design and Results of Nasal Influenza Vaccine Powder Formulation

In this experiment, the ability of a dry powder H1N1 vaccine to elicit an immune response is tested and compared to conventional nasal and injected liquid formulations. The vaccine is prepared using a quick freezing process and blended with microcrystalline cellulose carriers, as explained supra. In each condition, 0.09 mg of influenza vaccine protein (H1N1, strain A/Brisbane/59/2007, inactive whole influenza vaccine) was administered to 4 groups of cynomolgus monkeys. Cynomolgus monkeys have similar anatomy of nasal cavity and similar immune response as humans. Group 1 was administered 25 mg of nasal influenza (H1N1) vaccine powder formulation, prepared by the quick freezing process outlined supra, containing 0.09 mg influenza vaccine protein, 1.91 mg trehalose, 19.28 mg Ceolus (registered trademark) PH-F20JP, 2.50 mg Ceolus (registered trademark) PH-301, and 0.10 mg TCP; Group 2 was administered 0.1 ml of nasal influenza vaccine solution containing 0.09 mg influenza vaccine protein; Group 3 was administered 0.1 ml of nasal influenza vaccine solution containing 0.09 mg influenza vaccine protein, 0.5 microL Tween 80 with 0.02 mg adjuvant alpha-galactosylceramide; and Group 4 was administered 0.5 mL of SC influenza vaccine solution containing 0.09 mg influenza vaccine protein. Vaccines were administered and samples were collected as described in FIG. 4. Antibody levels were determined by hemagglutination inhibition (HI) and enzyme-linked immunosorbent assay (ELISA).

Hemagglutination Inhibition (HI) antibody titers in serum and nasal wash samples were determined as follows. Samples were treated with Receptor Destroying Enzyme (RDE, Denka Seiken Co Ltd., Tokyo, Japan) for 15 to 18 hours at 37 degrees C. and then heat inactivated for 1 hour at 56 degrees C. Two-fold serial dilution series of the samples were prepared, mixed with H1N1 (strain A/Brisbane/59/2007) HA antigen (Denka Seiken) at a concentration of 4 hemagglutination units per well, and incubated for 1 hour at room temperature. To each well, 50 micro L of a 0.5% suspension of chicken red blood cells was added and hemagglutination was assessed an hour later. The highest dilution of sample that inhibits hemagglutination is the HI title of the sample.

The results of HI testing of samples collected in this study are shown in FIGS. 5A and B, which contain tables of the HI titers produced by monkeys exposed to the different formulations of the whole inactive H1N1 virus (strain A/Brisbane/59/2007) vaccine. The HI titers measured in serum samples are found in 5A; the HI titers measured in nasal wash samples are found in 5B. The SC injection vaccine (Group 4) produced the highest HI titers in the serum samples; however, no increase in HI titer was detected in nasal wash samples. Of the nasal preparations, the whole inactive nasal influenza (H1N1, strain A/Brisbane/59/2007) vaccine powder formulation produced the highest titers in both the serum and nasal wash samples, demonstrating a clear improvement over the liquid formulations. Taken together, these results demonstrate that both serum and nasal wash HI titers were elevated in test group 1.

Enzyme-linked immunosorbent assay (ELISA) antibody titers in serum and nasal wash samples were determined as follows. ELISA plates were coated with an antigen for 17 hours at 4 degrees C., washed, and blocked in 100 micro L of blocking solution (0.5% bovine serum albumin in phosphate buffer) for 1 hour at room temperature. After washing, 2-fold serial dilutions of the test samples were made in 0.5% BSA and PBS and the dilutions were added to the wells of the ELISA plate. After an incubation at 37 degrees C. for 1 hour, the plates were washed and incubated with a horseradish peroxidase (HRP)-conjugated goat anti-monkey IgG or HRP-conjugated sheep anti-monkey secretory component detection antiserum for 1 hour at 37 degrees C. The plates were then washed, incubated with o-Phenylenediamine (OPD) for 15 minutes at 37 degrees C., and the color reaction stopped by the addition of 100 micro L of 1M sulfuric acid ($H_2SO_4$). The samples were measured by OD492 on an ELISA reader.

Figure 7:
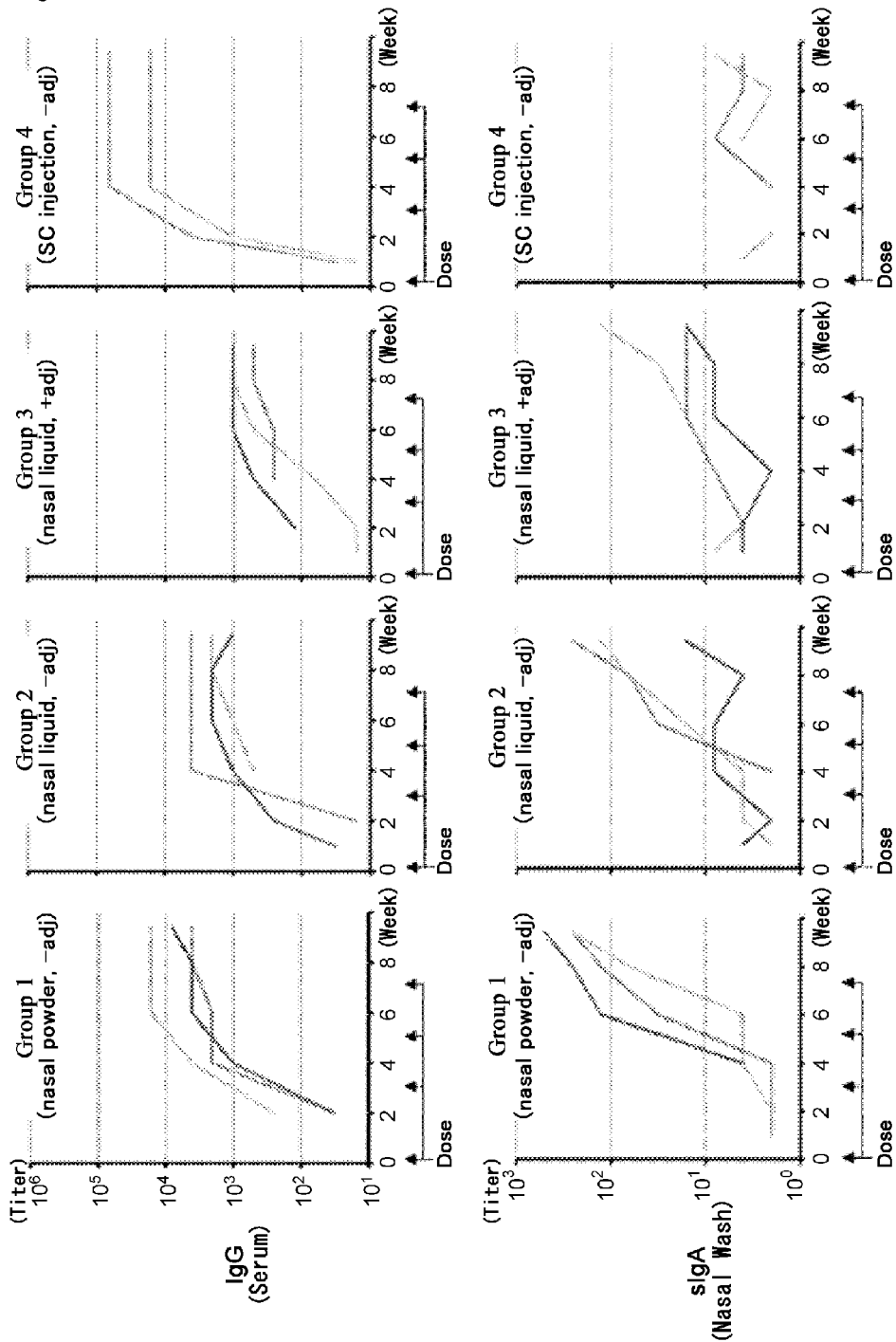
FIG. 7 graphically illustrates IgG and sIgA antibody titers measured during a test of a H1N1 nasal influenza vaccine powder formulation.

The results of the ELISA antibody titers measured in the samples collected in this study are shown in FIGS. 6 and 7. FIGS. 6A and B are table of sIgA (5B) and IgG (5A) antibody titers produced by monkeys exposed to the different flu vaccine formulations. FIG. 7 provides a graphical representation of the data and indicating similar results from each animal tested (different animals indicated by different lines). SC Flu vaccine solution produced the most IgG among all test articles. Nasal influenza (H1N1, strain A/Brisbane/59/2007) vaccine powder formulation produced the most IgG among all nasal preparations. Nasal influenza vaccine powder formulation produced the most sIgA among all test articles. SC injected influenza vaccine produced the least sIgA among all test articles. Nasal influenza vaccine solution with adjuvant produced the least sIgA among all nasal preparations even though added the adjuvant.

Example 1D

HI, IgG and sIgA Titers During the Recovery Period

A subset of the animals from Example 1C was monitored following the end of the experiment to determine whether the elevated antibody titers were held. Serum and nasal wash samples were taken on day 80 (31 days after the last vaccination), day 101 (52 days post-vaccination) and day 115 (66 days post-vaccination). The results are found in FIGS. 8 and 9. FIG. 8 contains a table of HI titers; FIG. 9 contains a table of IgG and sIgA titers. Antibody titer levels were held at high levels in the animal treated with the nasal powder formulation (FIGS. 8 and 9, Group 1). Antibody titer levels were held at a lower level in animals treaded with the nasal liquid formulation, without (Group 2) or with (Group 3) the addition of an adjuvant. IgG and HI titer levels in animals injected with a liquid formulation (Group 4) decreased remarkably throughout the recovery period; the levels of sIgA antibodies were not significantly raised in animals treated with the injected vaccine formulation.

Example 1E

Survivability/Challenge Studies

In this example, the ability of the influenza vaccine to protect animals from subsequent challenge will be determined. Nasal challenge of the monkeys vaccinated in the previous experiment is performed 3 weeks after the final immunization. The animals are challenged with an embryonated-chicken-egg grown canine influenza (A/Brisbane/59/2007 IVR-148) virus. Each animal receives a total of approximately $10^7$ $TCID_{50}$ of virus in a 2 ml volume. For mock challenge, the monkeys are challenged with 2 ml of virus-free allantoic fluid. As further controls, three unvaccinated monkeys are exposed to $10^7$ $TCID_{50}$ of virus or challenged with 2 ml of virus-free allantoic fluid.

Animals from each group are monitored daily for body mass, hypothermia, general appearance and clinical symptoms. The monkeys are observed for flu-related clinical signs for 28 days post-challenge. All monkeys are fed with a standard diet and water is available ad libitum. For each group studied, nasal swabs and blood samples are taken at −7 days, 3 days, 7 days, 14 days and 28 days following the initial challenge. Antibody titers (sIgA and IgG) are determined for each animal.

Example 1F

Determining Stability and Hygroscopicity of a Dry Vaccine Powder Formulation

In this example, the stability and hygroscopicity of a dry vaccine powder formulation will be examined. A dry, whole inactive H1N1 influenza vaccine powder formulation is generated by the methods of the provided invention. The stability of the vaccine powder formulation is tested at 45 degrees C. and at 20 degrees C. to 25 degrees C. The dry vaccine powder formulation to be tested is stored both in sealed bottles and in unsealed containers. Stability is measured by determining HA antigenicity.

The hygroscopicity of a dry vaccine powder formulation is measured by determining the mass of a sample over time. To determine the effects of different environmental conditions on the hygroscopic stability of dry vaccine powders, 50 mg of vaccine powder is stored under various conditions. Samples of dry vaccine powder are stored under air-tight conditions, in a sealed container and an open container. The samples are weighed at monthly intervals for 6 months and weighed. An increase in weight indicates acquisition of water.

Vaccine powder formulation stored for longer than 6 months are tested in a nasal delivery device. The percent of vaccine powder formulation delivered from the device is determined and compared to the percent of vaccine powder formulation freshly made.

Example 2

Preparation and Testing of Whole Inactive H5N1 Dry Vaccine Powder Formulation

In this example, various dry powder formulations of the avian flu vaccine (H5N1) are generated and tested. A preferred embodiment of the invention is also tested verses traditional liquid nasal and injection formulations of the avian flu vaccine.

Example 2A

Preparation of a Nasal Influenza (H5N1) Vaccine Powder Using a Quick Freezing Process This example was performed to determine the optimal antigen stabilizer, and antigen to stabilizer ratio, for use in a quick freezing and drying process to generate a H5N1 nasal vaccine powder. The general manufacturing process is outlined in FIGS. 2 and 3; specific details relating to the generation of a H5N1 nasal vaccine formulation are provided infra. Four ratios of antigen to stabilizer were tested (1:11, 1:21, 1:49, and 1:101); the numbers cited infra correspond to the 1:49 ratio formulation. In a 10 mL bottle, 0.4 mL of a 0.526 mg/mL antigen solution containing whole inactive H5N1 virus (strain A/Vietnam/1194/2004, Sinovac Biotech Ltd) is combined with 10.4 mg of a stabilizer (trehalose, mannitol, or lactose) in 0.4 mL phosphate buffer pH 7.2, to yield a final ratio of antigen to stabilizer of 1:49. The mixture is quickly frozen in liquid nitrogen for 10 minutes and an influenza powder is generated by a four step freeze-drying process: −40 degrees C., less than 140 mtorr for 24 hr; −30 degrees C., less than 130 mtorr for 36 hr; −10 degrees C., less than 100 mtorr for 4 hr; and 20 degrees C., less than 50 mtorr for 4 hr. The resulting powder contains 11.2 micro g of antigen per 1 mg of powder. The influenza vaccine powder is combined (blended) with nasal carriers (e.g., microcrystalline cellulose) with specific surface area of greater than 1.3 square meter per gram and tribasic calcium phosphate (TCP) $(Ca_3(PO_4)_2)$. Influenza vaccine powder (104 mg, including 1.2 mg of influenza vaccine protein, is combined with 254.4 mg of Ceolus (registered trademark) PH-F20JP microcrystalline cellulose (mean particle size: 57 micro m; bulk density: 0.23 g/cm3; specific surface area: 2.3 m2/g), 40.0 mg of Ceolus (registered trademark) PH-301 microcrystalline cellulose (mean particle size: 39 micro m; bulk density: 0.41 g/cm3), and 1.6 mg of TCP in a 10 mL glass bottle, and the components are blended using a vortex mixer for one minute. The resulting dry influenza vaccine powder formulation contains 58.9 micro g of influenza vaccine protein per 20 mg of dry influenza vaccine powder formulation. Use of trehalose, mannitol, and lactose as a stabilizer produce stable powders consisting of fine particles at the 1:21 and 1:49 antigen to stabilizer ratios. At the 1:101 antigen to stabilizer ratio, both trehalose and lactose containing formulations produced caked but stable powders; mannitol produced a stable powder consisting of fine particles at the 1:101 antigen to stabilizer ratio. Use of trehalose, mannitol, and lactose produced unstable formulations at antigen to stabilizer ratios of 1:11. The results are summarized in Table 3.

vaccine powder in each nostril (30 micro g total antigen); Group 2 was administered 0.15 mL nasal flu spray in each nostril (30 micro g total antigen); and Group 3 was administered 0.3 mL of liquid vaccine by intramuscular injection (IM). Vaccines were administered and samples were collected according to the schedule in FIG. 10. Samples were tested by enzyme-linked immunosorbent assay (ELISA) according to the methods outlined in Example 1.

The results of the ELISA antibody titers measured in the samples collected in this study are shown in FIGS. 11 and 12. FIG. 11 provides titers of sIgA (11B) and IgG (11A) produced by monkeys exposed to the different flu vaccine formulations. FIG. 12 provides a graphical representation of the data with different animals indicated by different lines. Animals vaccinated by injection with a liquid formulation (group 3) produced the highest IgG titers in the study; however, this same group produced levels of sIgA antibodies that were nearly undetectable. Animals vaccinated using a nasal liquid formulation (group 2) produced the lowest levels if IgG antibodies in this experiment; this group also produced low levels of sIgA antibodies. Animals vaccinated with the nasal powder formulation (group 1) produced the highest levels of IgG antibodies of the nasal vaccines; the nasal powder formulation also elicited the highest level of immune response as measured by sIgA antibody levels. These results indicate that both sIgA and IgG antibody titers were successfully elevated in animals treated with the H5N1 nasal powder vaccine formulation.

TABLE 3

Influenza (H5N1) vaccine powder generated by quick freezing technique.

| Total protein of antigen/ stabilizer ratio (by weight) | Trehalose | | Mannitol | | Lactose | |
| --- | --- | --- | --- | --- | --- | --- |
| | Powder Property | HA potency Stable: >50% Unstable: ≤50% | Powder Property | HA potency Stable: >50% Unstable ≤50% | Powder Property | HA potency Stable: >50% Unstable: ≤50% |
| 1:11 | Fine | Unstable | Fine | Unstable | Fine | Unstable |
| 1:21 | Fine | Stable | Fine | Stable | Fine | Stable |
| 1:49 | Fine | Stable | Fine | Stable | Fine | Stable |
| 1:101 | Cake | Stable | Fine | Stable | Cake | Stable |

Example 2B

Study Design and Results of Nasal Influenza Vaccine Powder Formulation

In this experiment, the ability of a dry powder vaccine to elicit an immune response in cynomolgus monkeys, was tested and compared to conventional nasal and injected liquid formulations. Cynomolgus monkeys have similar anatomy of nasal cavity and similar immune response as humans. The dry powder vaccine was prepared from whole inactivated H5N1 (strain A/Vietnam/1194/2004) antigen, using a quick freezing then freeze drying process, and blended with microcrystalline cellulose carriers as described supra. For every 20 mg of nasal influenza (H5N1) vaccine powder formulation, 58.9 micro g whole inactive H5N1 virus is delivered along with 2.9 mg trehalose, 12.7 mg Ceolus (registered trademark) PH-F20JP, 2.0 mg Ceolus (registered trademark) PH-301, and 0.08 mg tribasic calcium phosphate. In each condition, 30 micro g of H5N1 antigen was administered. Group 1 was administered 20 mg of nasal Example 2C Test Method and Results of Stability Test Under Stress Conditions In this experiment, the stability of the dry powder H5N1 vaccine formulation, prepared as described in Example 2A, is subjected to stress conditions and compared to a H5N1 nasal flu spray formulation. H5N1 influenza vaccine powder in encapsulated form was stored at 60 degrees C. and 0% relative humidity and examined at two and three week time points. At two weeks, the powder consisted of fine particles; however, at three weeks, partial aggregation of the powder was observed. In another test, H5N1 influenza vaccine powder was loaded in a single use delivery device (Shin Nippon Biomedical Laboratory, LTD) and stored with an oxygen and moisture absorbing desiccant (PharmaKeep KC-20, Mitsubishi Gas Chemical Company, Inc.) in an aluminum canister at 60 degrees C. and 75% relative humidity for two weeks, after which the powder still consisted of fine particles. In yet another test, H5N1 influenza vaccine powder was put in bottles and stored at 60 degrees C. and 0% relative humidity and examined for HA potency at two and three week time points. At both times, the HA potency of the H5N1 nasal vaccine powder was stable. In another test of HA potency, H5N1 influenza vaccine powder was put in bottles and stored with an oxygen and moisture absorbing desiccant (PharmaKeep KC-20, Mitsubishi Gas Chemical Company, Inc.) at 60 degrees C. and 75% relative humidity for two weeks, after which time the HA potency was determined to be stable. These results are summarized in Table 4. In contrast to the H5N1 nasal powder vaccine, H5N1 nasal spray vaccine, which was stored in a polypropylene microtube, lost all HA potency after two weeks at 60 degrees C. This demonstrates that increased stability at elevated temperature is achieved in the nasal powder formulation.

TABLE 4

H5N1 influenza vaccine powder stress test results

| | Powder Property | | HA Potency (Stable: >50%, | |
|---|---|---|---|---|
| Time | Encapsulated | Loaded in Delivery Device | Bottled | Unstable ≤50%) Packaged |
| Initial | Fine Particles | Fine Particles | Stable | Stable |
| 2 Weeks | Fine Particles | Fine Particles | Stable | Stable |
| 3 Weeks | Partially Aggregated | | Stable | |

Example 3

Preparation and Testing of a Mixture of 3 HA Split Inactivated Strain Dry Vaccine Powder Formulation In this example, various dry powder formulations of a nasal powder vaccine, containing a mixture of 3 split-inactivated strains (H1N1 A/California/7/2009, H3N2 A/Victoria/210/2009, and B/Brisbane/60/2008—collectively: "Trivalent HA influenza"), are generated and tested.

Example 3A

Preparation of a Trivalent HA Influenza Vaccine Powder Using a Quick Freezing Process This experiment was performed to determine the optimal antigen stabilizer, and antigen to stabilizer ratio, for use in a quick freezing and drying process to generate a Trivalent HA influenza nasal vaccine powder. The general manufacturing process is outlined in FIGS. 2 and 3; specific details relating to the generation of a Trivalent HA influenza nasal vaccine formulation are provided infra. Four ratios of antigen to stabilizer were tested (1:26, 1:56, 1:111, and 1:222); the numbers cited infra correspond to the 1:111 ratio formulation. In a 10 mL bottle, 0.6 mL of a >0.09 mg/mL antigen solution containing Trivalent HA influenza (H1N1 A/California/7/2009, H3N2 A/Victoria/210/2009, and B/Brisbane/60/2008, Denka Seiken Co Ltd) is combined with 6 mg of a stabilizer (trehalose, mannitol, or lactose) in 0.2 mL ultra pure water, to yield a final ratio of antigen to stabilizer of 1:111. The mixture is quickly frozen in liquid nitrogen for 10 minutes and an influenza powder is generated by a four step freeze-drying process: −40 degrees C., less than 140 mtorr for 24 hr; −30 degrees C., less than 130 mtorr for 36 hr; −10 degrees C., less than 100 mtorr for 4 hr; and 20 degrees C., less than 50 mtorr for 4 hr. The resulting powder contains >4.6 micro g of antigen per 1 mg of powder. The influenza vaccine powder is combined (blended) with nasal carriers (e.g., microcrystalline cellulose) with specific surface area of greater than 1.3 square meter per gram and tribasic calcium phosphate (TCP) ($Ca_3(PO_4)_2$). Influenza vaccine powder (97.75 mg, including 0.45 mg of influenza vaccine protein, is combined with 350.2 mg of Ceolus (registered trademark) PH-F20JP microcrystalline cellulose (mean particle size: 57 micro m; bulk density: 0.23 g/cm3; specific surface area: 2.3 m2/g), 50.0 mg of Ceolus (registered trademark) PH-301 microcrystalline cellulose (mean particle size: 39 micro m; bulk density: 0.41 g/cm3), and 2.0 mg of TCP in a 10 mL glass bottle, and the components are blended using a vortex mixer for one minute. The resulting dry influenza vaccine powder formulation contains >45 micro g of influenza vaccine protein per 25 mg of dry influenza vaccine powder formulation. Preparations using trehalose, mannitol, and lactose at an antigen to stabilizer ratio of 1:26 produced unstable powders consisting of fine particles. Both trehalose and lactose containing formulations produced stable powders with fine particle size at antigen to stabilizer ratios of 1:56 and 1:111; at these ratios, use of mannitol as the stabilizer yielded unstable HA potency with fine particle size. At an antigen to stabilizer ratio of 1:222, both trehalose and lactose containing formulations produced caked powders with stable HA potency; at the same ratio, the mannitol containing formulation produced a stable powder consisting of fine particles. The results are summarized in Table 5.

TABLE 5

Trivalent HA influenza vaccine powder generated by quick freezing technique.

| Conventional | Trehalose | | Mannitol | | Lactose | |
|---|---|---|---|---|---|---|
| Freezing, and Drying Weight ratio/ Using excipients | Particle size | HA potency Stable: >50% Unstable: ≤50% | Particle size | HA potency Stable: >50% Unstable: ≤50% | Particle size | HA potency Stable: >50% Unstable: ≤50% |
| 1:26 | Fine | Unstable | Fine | Unstable | Fine | Unstable |
| 1:56 | Fine | Stable | Fine | Unstable | Fine | Stable |
| 1:111 | Fine | Stable | Fine | Unstable | Fine | Stable |
| 1:222 | Cake | Stable | Fine | Stable | Cake | Stable |

Example 3B

Test Method and Results of Stability Test Under Stress Conditions

In this experiment, the stability of the dry powder Trivalent HA influenza vaccine formulation, prepared using a quick freezing process and blended with microcrystalline cellulose carriers, is tested under stress conditions and compared to a nasal spray Trivalent HA influenza vaccine formulation. Trivalent HA influenza vaccine powder in encapsulated form was stored at 60 degrees C. and 0% relative humidity and examined at two and three week time points. At two weeks, the powder consisted of fine particles; however, at three weeks, partial aggregation of the powder was observed. In yet another test, Trivalent HA influenza vaccine powder was put in bottles and stored at 60 degrees C. and 0% relative humidity and examined for HA potency at two and three week time points. At both times, the HA potency of the Trivalent HA nasal vaccine powder was stable. These results are summarized in Table 6. In contrast to the Trivalent HA nasal powder vaccine, nasal spray Trivalent HA nasal spray vaccine, which was stored in a polypropylene microtube, lost all HA potency after two weeks at 60 degrees C. This demonstrates that increased stability at elevated temperature is achieved in the nasal powder formulation.

TABLE 6

Bottled Trivalent HA influenza nasal powder vaccine stress test results

| time | Powder Consistency | HA potency Stable: >50% Unstable: ≤50% |
|---|---|---|
| Initial | Fine Particles | Stable |
| 2 Weeks | Fine Particles | Stable |
| 3 Weeks | Partially Aggregated | Stable |

Example 4

Preparation and Testing of Tetanus Toxoid (TTx) Dry Vaccine Powder Formulation In this example, various dry powder formulations of a tetanus toxoid (TTx) vaccine, are generated and tested. A preferred embodiment of the invention is also tested verses a traditional liquid injection formulation of the TTx vaccine.

Example 4A

Preparation of a Tetanus Toxoid Vaccine Powder Using a Quick Freezing Process This experiment was performed to determine the optimal antigen stabilizer, and antigen to stabilizer ratio, for use in a quick freezing and drying process to generate a tetanus toxoid nasal vaccine powder. The general manufacturing process is outlined in FIGS. 2 and 3; specific details relating to the generation of a tetanus toxoid nasal vaccine formulation are provided infra. Five ratios of antigen to stabilizer were tested (1:26, 1:53, 1:111, 1:231, and 1: greater than 420); the numbers cited infra correspond to the 1:53 ratio formulation. In a 10 mL bottle, 0.5 mL of a less than 0.08 mg/mL adsorbed tetanus toxoid antigen solution (Denka Seiken Co LTD) is combined with 2.1 mg of a stabilizer (trehalose, mannitol, or lactose) in 0.3 mL ultra pure water, to yield a final ratio of antigen to stabilizer of 1:53. The mixture is quickly frozen in liquid nitrogen for 10 minutes and an antigen powder is generated by a four step freeze-drying process: −40 degrees C., less than 140 mtorr for 24 hr; −30 degrees C., less than 130 mtorr for 36 hr; −10 degrees C., less than 100 mtorr for 4 hr; and 20 degrees C., less than 50 mtorr for 4 hr. The resulting powder contains less than 4.7 micro g of antigen per 1 mg of powder. The tetanus toxoid vaccine powder is combined (blended) with nasal carriers (e.g., microcrystalline cellulose) with specific surface area of greater than 1.3 square meter per gram and tribasic calcium phosphate (TCP) ($Ca_3(PO_4)_2$). Tetanus toxoid vaccine powder (less than 8.54 mg, including less than 0.04 mg of antigen protein, is combined with 35.46 mg of Ceolus (registered trademark) PH-F20JP microcrystalline cellulose (mean particle size: 57 micro m; bulk density: 0.23 g/cm3; specific surface area: 2.3 m2/g), 5 mg of Ceolus (registered trademark) PH-301 microcrystalline cellulose (mean particle size: 39 micro m; bulk density: 0.41 g/cm3), and 0.2 mg of TCP in a 10 mL glass bottle, and the components are blended using a vortex mixer for one minute. The resulting dry tetanus toxoid vaccine powder formulation contains less than 20 micro g of antigen protein per 25 mg of total powder. The use of trehalose, mannitol, and lactose produced antigen powders consisting of fine particles at antigen to stabilizer ratios of 1:26, 1:53, 1:105, and 1:210. At an antigen to stabilizer ratio of 1:420, all three stabilizers (trehalose, mannitol, and lactose) produced caked powders. The results are summarized in Table 7.

TABLE 7

Tetanus toxoid vaccine powder generated by quick freezing technique.

| Total protein of antigen/ stabilizer ratio (by weight) | Trehalose Powder Property | Mannitol Powder Property | Lactose Powder Property |
|---|---|---|---|
| 1:26 | Fine | Fine | Fine |
| 1:53 | Fine | Fine | Fine |
| 1:105 | Fine | Fine | Fine |
| 1:210 | Fine | Fine | Fine |
| 1:420 | Cake | Cake | Cake |

Example 4B

Study Design and Results of Nasal Tetanus Toxoid Vaccine Powder Formulation

In this experiment, the ability of a tetanus toxoid nasal powder vaccine to elicit an immune response in cynomolgus monkeys, is tested and compared to a conventional injected liquid formulation. Cynomolgus monkeys have similar anatomy of nasal cavity and similar immune response as humans. The dry powder vaccine is prepared from adsorbed tetanus toxoid antigen, using a quick freezing then freeze drying process, and blended with microcrystalline cellulose carriers as described in Example 4A. For every 25 mg of nasal tetanus toxoid vaccine powder formulation, 2.5 Lf of adsorbed tetanus toxoid antigen is delivered along with 1.1 mg trehalose, 17.9 mg Ceolus (registered trademark) PH-F20JP, 2.6 mg Ceolus (registered trademark) PH-301, and 0.1 mg tribasic calcium phosphate. Multiple dosing levels are compared. Group 1 is administered 25 mg of nasal vaccine powder in each nostril (5 Lf dose); Group 2 is administered 25 mg of nasal vaccine powder two times in each nostril (10 Lf dose); Group 3 is administered 25 mg of nasal vaccine powder four times in each nostril (20 Lf dose); and, Group 4 is administered 2.0 mL liquid vaccine by subcutaneous injection (10 Lf dose). Vaccines are administered and samples are collected according to the schedule in FIG. 13. Samples are tested by enzyme-linked immunosorbent assay (ELISA), according to the methods outlined in Example 1, and enzyme-linked immunosorbent spot (ELISpot).

The ELISpot assay was performed as follows. Mouse anti-human/monkey interferon-gamma (IFN gamma), monoclonal antibody, unconjugated, clone GZ-4 (15 micro g/mL, MabTech, Sweden) was added to multiscreen plates (Millipore, USA) and incubated overnight at 4 degrees C. The next day, the plates were blocked with AIM-V (Life Technologies, USA) complete medium. $4 \times 10^5$ cells of peripheral blood mononuclear cells (PBMCs) separated from monkey whole blood and 25 mLf of Absorbed Tetanus Toxoid were added, and the plates incubated for 24 hour at 37 degrees C. The wells were then washed with PBS and 1 micro g/mL mouse anti-human IFN gamma, monoclonal antibody, biotinylated, clone 7-B6-1 (MabTech) was added. After 2 hour incubation at room temperature, the wells were washed with PBS. Streptavidine-alkaline phosphatase diluted 1:1000 (MabTech) was added. After 1 hour incubation at room temperature, the wells were washed with PBS. Staining was performed using 5-bromo-4-chloro-3-indolyl phosphate/nitroblue tetrazolium (BCIP/NBT-plus substrate) (Moss, USA). The plates were dried and numbers of spot in each well were evaluated on a scale of − to ++.

The antibody titers measured in the samples collected in this study are shown in FIGS. 14 and 15. FIG. 14A provides the absorbance ratio of serum IgG produced by monkeys exposed to the different flu vaccine formulations; FIG. 14B displays those same results in graphical form. FIG. 15 tabulates the results of ELISpot testing of the serum samples collected. The scoring in FIG. 15 is as follows: (−) indicates negative control levels, (+/−) indicates low levels, (+) indicates medium levels, and (++) indicates high levels. In both the ELISA and ELISpot tests, the injected liquid formulation of the TTx vaccine produced the greatest immune response. The 20 Lf dose of the nasal powder induced a detectable increase in IgG antibody titer during the study as measured by ELISA. The ELISpot measurements showed that all three doses of TTx Nasal powder vaccine were able to produce a dose-dependent immune response.

Example 5

Preparation and Testing of Diphtheria Toxoid (DTx) Dry Vaccine Powder Formulation In this example, various dry powder formulations of a diphtheria toxoid vaccine, are generated and tested. A preferred embodiment of the invention is also tested verses a traditional liquid injection formulation of the diphtheria toxoid vaccine. To test the stability of the diphtheria toxoid antigen during processing, the antigen powder produced by the quick freezing and freeze drying process detailed supra was rehydrated into a liquid formulation. This formulation will be referred to as reconstituted powder infra.

Example 5A

Preparation of a Diphtheria Toxoid Vaccine Powder Using a Quick Freezing Process This experiment was performed to determine the optimal antigen stabilizer, and antigen to stabilizer ratio, for use in a quick freezing and drying process to generate a diphtheria toxoid nasal vaccine powder. The general manufacturing process is outlined in FIGS. 2 and 3; specific details relating to the generation of a diphtheria toxoid nasal vaccine formulation are provided infra. Five ratios of antigen to stabilizer were tested (2.5 Lf:1.1 mg, 2.5 Lf:2.1 mg, 2.5 Lf:4.2 mg, 2.5 Lf: 8.4 mg and 2.5 Lf: 16.8 mg); the numbers cited infra correspond to the 2.5 Lf:2.1 mg ratio formulation. In a 10 mL bottle, 0.5 mL of a less than 5 Lf/mL adsorbed diphtheria toxoid antigen solution (DTx, Research Institute for Microbial Disease, Osaka University) is combined with 2.1 mg of a stabilizer (trehalose, mannitol, or lactose) in 0.3 mL ultra pure water, to yield a final ratio of antigen to stabilizer of 2.5 Lf:2.1 mg. The mixture is quickly frozen in liquid nitrogen for 10 minutes and an antigen powder is generated by a four step freeze-drying process: −40 degrees C., less than 140 mtorr for 24 hr; −30 degrees C., less than 130 mtorr for 36 hr; −10 degrees C., less than 100 mtorr for 4 hr; and 20 degrees C., less than 50 mtorr for 4 hr. The resulting powder contains less than 0.28 Lf of antigen per 1 mg of powder. The diphtheria toxoid vaccine powder is combined (blended) with nasal carriers (e.g., microcrystalline cellulose) with specific surface area of greater than 1.3 square meter per gram and tribasic calcium phosphate (TCP) ($Ca_3(PO_4)_2$). Diphtheria toxoid vaccine powder (1 mg, including less than 0.28 Lf of antigen protein), is combined with 35.96 mg of Ceolus (registered trademark) PH-F20JP microcrystalline cellulose (mean particle size: 57 micro m; bulk density: 0.23 g/cm3; specific surface area: 2.3 m2/g), 5 mg of Ceolus (registered trademark) PH-301 microcrystalline cellulose (mean particle size: 39 micro m; bulk density: 0.41 g/cm3), and 0.2 mg of TCP in a 10 mL glass bottle, and the components are blended using a vortex mixer for one minute. The resulting dry diphtheria toxoid vaccine powder formulation contains less than 1.25 Lf of antigen protein per 25 mg of total powder. The results are summarized in Table 8. Use of trehalose, mannitol, or lactose generated powders consisting of fine particles at antigen to stabilizer ratios of 2.5 Lf:1.1 mg, 2.5 Lf:2.1 mg, 2.5 Lf:4.2 mg and 2.5 Lf:8.4 mg. At an antigen to stabilizer ratio of 2.5 Lf:16.8 mg, all three stabilizers used generated caked powders using this process.

TABLE 8

Diphtheria toxoid vaccine powder generated by quick freezing technique.

| Lf/Stabilizer | Trehalose Powder Property | Mannitol Powder Property | Lactose Powder Property |
| --- | --- | --- | --- |
| 2.5 LF/1.1 mg | Fine | Fine | Fine |
| 2.5 LF/2.1 mg | Fine | Fine | Fine |
| 2.5 LF/4.2 mg | Fine | Fine | Fine |
| 2.5 LF/8.4 mg | Fine | Fine | Fine |
| 2.5 LF/16.8 mg | Cake | Cake | Cake |

Example 5B

Study Design and Results of Nasal Diphtheria Toxoid Vaccine Powder Formulation

In this experiment, the ability of a diphtheria toxoid nasal powder vaccine to elicit an immune response in cynomolgus monkeys, is tested and compared to a conventional injected liquid formulation and a reconstituted powder formulation. Cynomolgus monkeys have similar anatomy of nasal cavity and similar immune response as humans. The dry powder vaccine was prepared from adsorbed diphtheria toxoid antigen, using a quick freezing then freeze drying process, and blended with microcrystalline cellulose carriers as described supra. For every 25 mg of nasal diphtheria toxoid vaccine powder formulation, 1.25 Lf of diphtheria toxoid antigen is delivered along with 1.1 mg trehalose, 21.3 mg Ceolus (registered trademark) PH-F20JP, 3.0 mg Ceolus (registered trademark) PH-301, and 0.12 mg tribasic calcium phosphate. Group 1 was administered 25 mg of nasal vaccine powder in each nostril (2.5 Lf dose); Group 2 was administered 1.0 mL of liquid vaccine by subcutaneous injection (5 Lf dose); and, Group 3 was administered 1.0 mL of reconstituted powder vaccine by subcutaneous injection (5 Lf dose). Vaccines were administered and samples were collected according to the schedule in FIG. 16. Samples were tested by enzyme-linked immunosorbent assay (ELISA), according to the methods outlined in Example 1.

The antibody titers measured in this experiment are shown in FIG. 17. FIG. 17A is a table of the absorbance ratio of serum IgG; 17B is a bar graph (top) and line graph (bottom) of the data in 17A. The reconstituted powder formulation and the conventional injected liquid formulations successfully induced an increase in serum IgG levels. The nasal powder formulation was also successful in increasing the IgG antibody titer, despite being administered at half the dose of the injected formulations. Taken together, these results indicate that the quick freeze drying methodology disclosed herein preserves diphtheria toxoid vaccine potency in animals.

Example 6

Preparation and Testing of Ovalbumin Dry Vaccine Powder Formulation

In this example, a dry powder formulation of ovalbumin (OVA, SIGMA A5503-IG) is generated and tested for the ability to elicit an immune response in cynomolgus monkeys. The nasally administered dry vaccine powder formulation is compared to traditional nasal and injected liquid formulations. The results demonstrate that nasal administration of an exemplary protein antigen using a formulation describe herein is capable of eliciting an immune response in animals.

Example 6A

Preparation of an Ovalbumin Dry Vaccine Powder

Three formulations of homogenized ovalbumin (hOVA) nasal powder are generated by blending different amounts of hOVA powder with nasal carriers (e.g., microcrystalline cellulose) with specific surface area of greater than 1.3 square meter per gram and tribasic calcium phosphate (TCP) ($Ca_3(PO_4)_2$). As hOVA is provided in powdered form, a quick freeze then freeze dry step was not needed. In formulation 1, 13.3 mg of hOVA powder is combined with 354.1 mg of Ceolus PH-F20JP, 40 mg Ceolus PH-301, and 1.6 mg of tribasic calcium phosphate (TCP), in a 10 mL bottle, and blended using a vortex mixer for one minute. The resulting mixture contains 1 mg antigen per 30 mg powder formulation. In formulation 2, 66.7 mg of hOVA powder is combined with 291.7 mg of Ceolus PH-F20JP, 40 mg Ceolus PH-301, and 1.6 mg of tribasic calcium phosphate (TCP), in a 10 mL bottle, and blended using a vortex mixer for one minute. The resulting mixture contains 5 mg antigen per 30 mg powder formulation. In formulation 3, 200 mg of hOVA powder is combined with 158.4 mg of Ceolus PH-F20JP, 40 mg Ceolus PH-301, and 1.6 mg of tribasic calcium phosphate (TCP), in a 10 mL bottle, and blended using a vortex mixer for one minute. The resulting mixture contains 15 mg antigen per 30 mg powder formulation.

Example 6B

Study Design and Results of Nasal Ovalbumin Vaccine Powder Formulation

In this experiment, the ability of an ovalbumin nasal powder vaccine to elicit an immune response in cynomolgus monkeys, is tested and compared to conventional injected and nasal liquid formulations wherein hOVA was dissolved in phosphate buffer. Cynomolgus monkeys have similar anatomy of nasal cavity and similar immune response as humans. The dry powder vaccine was prepared from homogenized ovalbumin powder and blended with excipients as describe supra. Group 1 was administered 30 mg of nasal vaccine powder formulation 1 in each nostril (2 mg dose); Group 2 was administered 30 mg of nasal vaccine powder formulation 2 in each nostril (10 mg dose); Group 3 was administered 30 mg of nasal vaccine powder formulation 3 in each nostril (30 mg dose); Group 4 was administered 0.1 mL of liquid vaccine in each nostril (20 mg dose); Group 5 was administered 0.1 mL of liquid vaccine in each nostril (30 mg dose); Group 6 was administered 1.0 mL of liquid vaccine by subcutaneous injection (20 mg dose); and, Group 7 was administered 1.0 mL of liquid vaccine by subcutaneous injection (30 mg dose). Vaccines were administered and samples were collected according to the schedule in FIG. 18. Samples were tested by enzyme-linked immunosorbent assay (ELISA), according to the methods outlined in Example 1.

The IgG antibody titers measured in the serum samples collected during this experiment are shown in FIG. 19. FIG. 19A is a table of IgG antibody titers; 19B is a bar graph (top) and line graph (bottom) representation of the data in 19A. The nasal powder formulation and the injected liquid formulation were both capable of eliciting an immune response to similarly high levels; however, the highest titers were detected at an earlier time point in the animals treated with the nasal powder formulation. The nasal liquid formulation failed to elicit a detectable immune response as measured by IgG antibody titer. The sIgA antibody titers measured in this serum samples collected during this experiment are shown in FIG. 20. FIG. 20A is a table of sIgA antibody titers; 20B is a bar graph (top) and line graph (bottom) representation of the data in 20A. Only the nasal powder formulation was capable of eliciting a detectable immune response as measured by sIgA antibody titer. No increase in sIgA titer was detected in animals vaccinated with either the nasal liquid or injected liquid formulations. Together, these results suggest that a nasal powder formulation described herein is capable of eliciting both mucosal and systemic immunogenicity in animals using an exemplary protein antigen.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for generating an intranasal dry vaccine powder formulation, comprising:
   (a) preparing a liquid formulation comprising one or more antigens and one or more saccharides;
   (b) quick freezing the liquid formulation to form a freeze-dried sample having an average particle diameter size of 10 to 100 microns without using a mill, wherein the quick freezing does not comprise spray freezing, and wherein the freeze-dried sample does not comprise an adjuvant; and
   (c) blending the freeze-dried sample with one or more excipients to generate the intranasal dry vaccine powder formulation.

2. The method of claim 1, wherein at least one of the one or more antigens is a viral antigen.

3. The method of claim 1, wherein at least one of the one or more antigens is influenza virus.

4. The method of claim 1, wherein at least one of the one or more antigens is H1N1 influenza virus.

5. The method of claim 1, wherein at least one of the one or more antigens is H5N1 influenza virus.

6. The method of claim 1, wherein the one or more antigens comprises H1N1 influenza virus, H3N2 influenza virus, and Influenza B virus.

7. The method of claim 1, wherein at least one of the one or more antigens is live attenuated virus, whole inactivated virus, split virus, subunit antigen, virosome, or cold-adapted live influenza virus.

8. The method of claim 1, wherein at least one of the one or more antigens is a bacterial antigen.

9. The method of claim 1, wherein at least one of the one or more antigens is killed whole bacteria, attenuated bacteria, toxoids, purified surface protein, or purified recombinant surface protein.

10. The method of claim 1, wherein at least one of the one or more antigens is tetanus toxoid.

11. The method of claim 1, wherein at least one of the one or more antigens is diphtheria toxoid.

12. The method of claim 1, wherein at least one of the one or more antigens is a protist antigen.

13. The method of claim 1, wherein at least one of the one or more antigens is a protein.

14. The method of claim 1, wherein at least one of the one or more saccharides is lactose.

15. The method of claim 1, wherein at least one of the one or more saccharides is trehalose.

16. The method of claim 1, wherein at least one of the one or more saccharides is mannitol.

17. The method of claim 1, wherein the liquid formulation further comprises one or more buffers.

18. The method of claim 17, wherein at least one of the one or more buffers is a phosphate buffer.

19. The method of claim 1, wherein the quick freezing comprises exposing the liquid formulation to a cold liquid for 1 minute to 60 minutes.

20. The method of claim 19, wherein the cold liquid is liquid nitrogen.

21. The method of claim 1, wherein the one or more excipients comprise tribasic calcium phosphate (TCP).

22. The method of claim 1, wherein the intranasal dry vaccine powder formulation does not comprise an adjuvant.

* * * * *